US012582706B2

(12) United States Patent
Pool et al.

(10) Patent No.: US 12,582,706 B2
(45) Date of Patent: Mar. 24, 2026

(54) TOLEROGENIC ANTIGEN PRESENTING CELLS

(71) Applicant: Cell4Cure AB, Solna (SE)

(72) Inventors: Lieneke Pool, Lund (SE); Pavlos Englezou, Lund (SE); Maria Wigren, Lund (SE); Hanne Romedahl, Lund (SE)

(73) Assignee: Cell4Cure AB, Solna (SE)

( * ) Notice: Subject to any disclaimer, the term of this patent is extended or adjusted under 35 U.S.C. 154(b) by 817 days.

(21) Appl. No.: 17/785,036

(22) PCT Filed: Dec. 11, 2020

(86) PCT No.: PCT/EP2020/085857
§ 371 (c)(1),
(2) Date: Jun. 13, 2022

(87) PCT Pub. No.: WO2021/116464
PCT Pub. Date: Jun. 17, 2021

(65) Prior Publication Data
US 2023/0118721 A1    Apr. 20, 2023

(30) Foreign Application Priority Data

Dec. 13, 2019    (GB) ..................................... 1918364

(51) Int. Cl.
| | |
|---|---|
| *A61P 37/06* | (2006.01) |
| *A61K 35/15* | (2025.01) |
| *A61K 39/00* | (2006.01) |
| *A61K 40/19* | (2025.01) |
| *A61K 40/22* | (2025.01) |
| *A61K 40/24* | (2025.01) |
| *A61K 40/41* | (2025.01) |
| *C12N 5/0784* | (2010.01) |

(52) U.S. Cl.
CPC .......... *A61K 39/0008* (2013.01); *A61K 35/15* (2013.01); *A61K 40/19* (2025.01); *A61K 40/22* (2025.01); *A61K 40/24* (2025.01); *A61K 40/416* (2025.01); *A61P 37/06* (2018.01); *C12N 5/064* (2013.01); *A61K 2039/577* (2013.01); *A61K 2239/31* (2023.05); *A61K 2239/38* (2023.05); *C12N 2501/15* (2013.01); *C12N 2501/22* (2013.01); *C12N 2501/2304* (2013.01); *C12N 2501/385* (2013.01); *C12N 2501/727* (2013.01); *C12N 2501/998* (2013.01); *C12N 2506/115* (2013.01)

(58) Field of Classification Search
None
See application file for complete search history.

(56) References Cited

U.S. PATENT DOCUMENTS

| | | | | |
|---|---|---|---|---|
| 6,458,585 B1 * | 10/2002 | Vachula | ............... | C12N 5/0639 |
| | | | | 435/405 |
| 2009/0136470 A1 * | 5/2009 | Cheroutre | ............... | A61P 37/08 |
| | | | | 514/432 |
| 2012/0251513 A1 * | 10/2012 | Hansson | ............ | A61K 39/4615 |
| | | | | 435/375 |

FOREIGN PATENT DOCUMENTS

| | | |
|---|---|---|
| WO | WO2008/157394 | 12/2008 |
| WO | WO2017/072251 | 5/2017 |
| WO | WO2018/037106 | 3/2018 |

OTHER PUBLICATIONS

Sun et al., J Exp Med, 2007, vol. 204, p. 1775-1785 (Year: 2007).*
Coombes et al., J Exp Med, 2007, vol. 204 , p. 1757-1764 (Year: 2007).*
Ragni et al., Exp Hematol. Jun. 2009;37(6):744-754 (Year: 2009).*
Mahiout et al., Toxicology in Vitro, vol. 52,2018 , p. 178 to 188 (Year: 2018).*
International Search Report and Written Opinion dated Feb. 24, 2021 for International Application PCT/EP2020/085857 filed Dec. 11, 2020 (13 pages).
Jurado-Manzano et al., FICZ generates human tDCs that induce CD4+ CD25high Foxp3+ Treg-like cell differentiation, Immunology Letters, vol. 190, Oct. 2017, pp. 84-92.
Mucida et al., Retinoic Acid Can Directly Promote TGF-beta-Mediated Foxp3+ Treg Cell Conversion of Naive T Cells, Immunity, vol. 30, No. 4, Apr. 17, 2009, pp. 471-472.
Salazar et al., The role of indoleamine 2,3-dioxygenase-aryl hydrocarbon receptor pathway in the TLR4-induced tolerogenic phenotype in human DCs, Scientific Reports, vol. 7, No. 1, Mar. 3, 2017 (11 pages).
Takenaka et al., Tolerogenic dendritic cells, Seminars In Immunopathology, vol. 39, No. 2, Sep. 19, 2016, pp. 113-120.

* cited by examiner

*Primary Examiner* — Daniel C Gamett
(74) *Attorney, Agent, or Firm* — Dentons US LLP

(57) ABSTRACT

There is provided inter alia according to the invention an ex vivo method of obtaining tolerogenic antigen presenting cells (APCs) that have the capability to induce tolerance in the immune system to an antigen, the method comprising (a) isolating monocytes from a sample obtained from a mammal; and (b) culturing the isolated monocytes in a cell culture to induce differentiation of the monocytes into antigen presenting cells having a tolerogenic phenotype, wherein the cell culture comprises (i) retinoic acid and TGFbeta, (ii) retinoic acid, TGFbeta and an AhR agonist or (iii) retinoic acid and an AhR agonist.

23 Claims, 38 Drawing Sheets

(A)

(A)

(A)

(A)

(A)

(A)

(B)
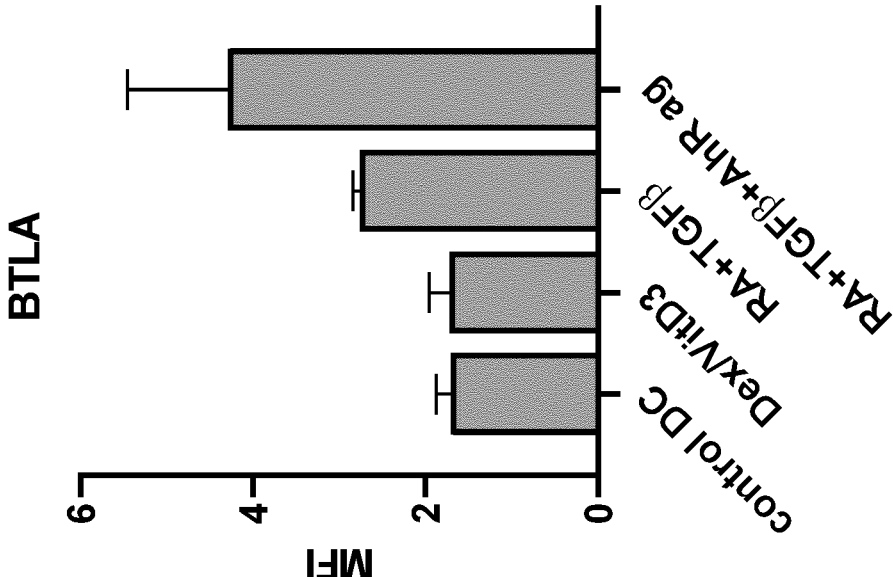
(B)
Figure 9
(A)
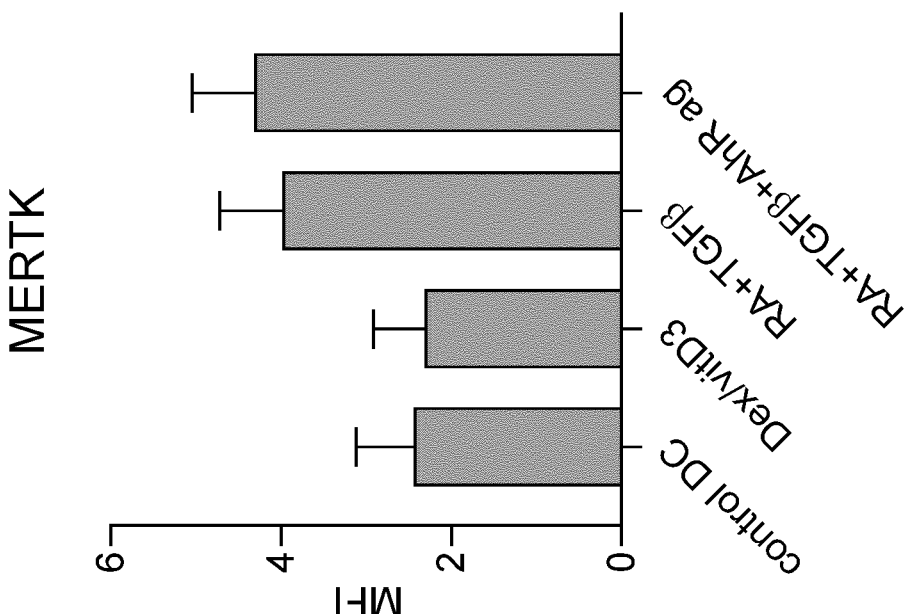

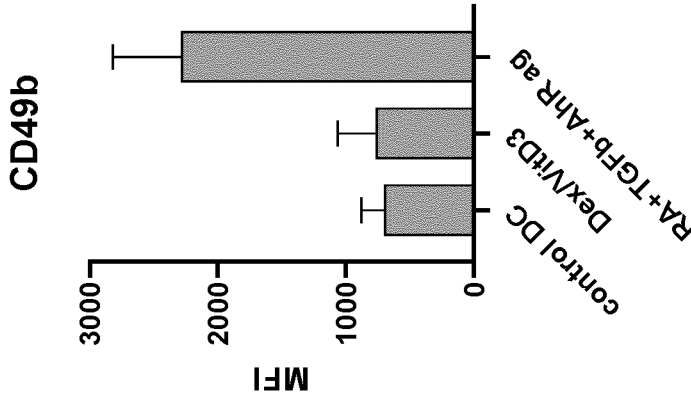
(E)
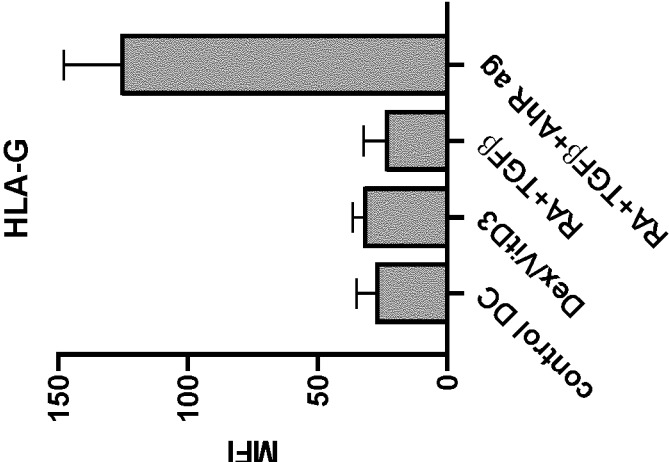
(D)
Figure 9 cont.
(C)
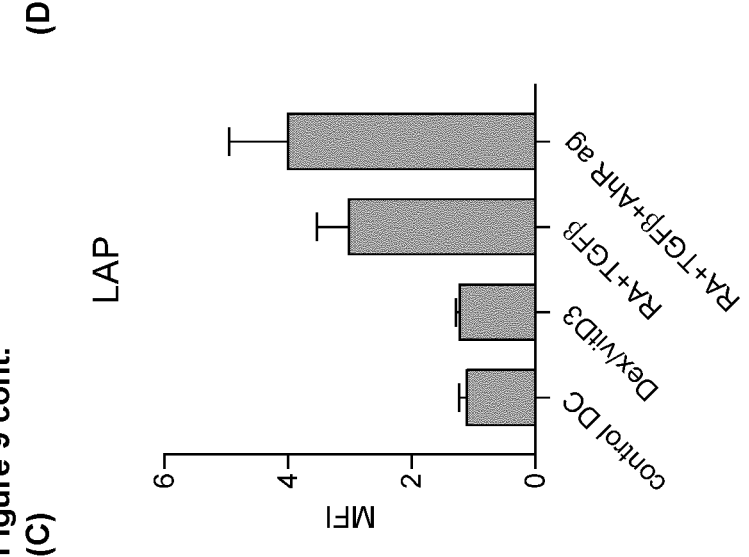

(A)

Figure 11
(A)
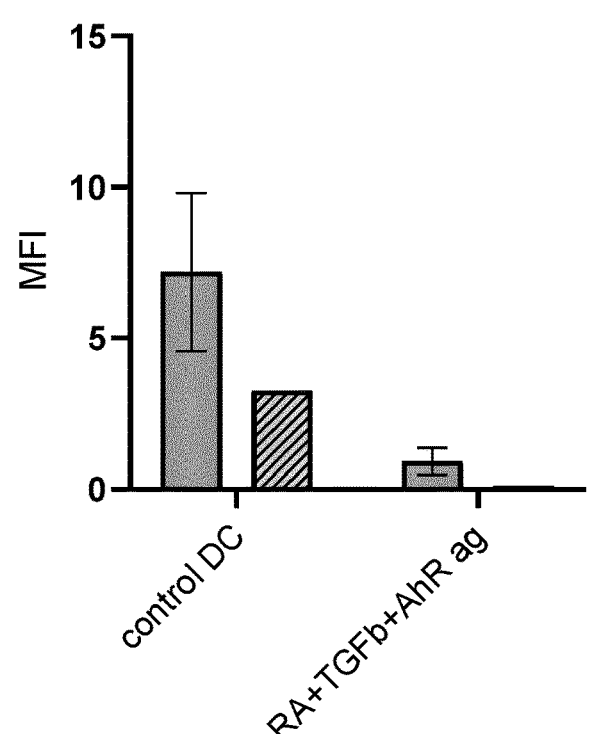
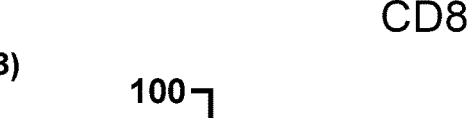
(B)
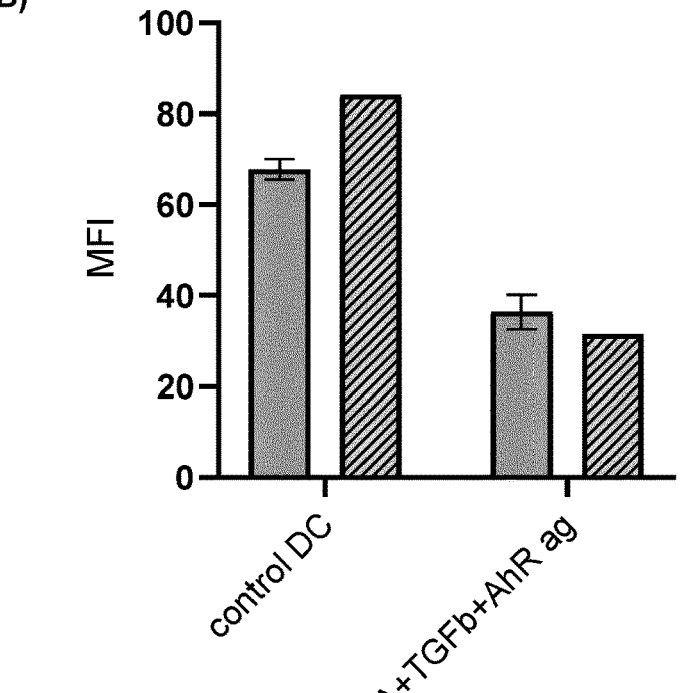

(C)

(D)

(E)

(F)

(G)

(H)

(I)

(J)

(A)

(B)

(C)

(D)

(E)

(F)

(G)

(A)

(B)

Figure 13 cont.
(C)
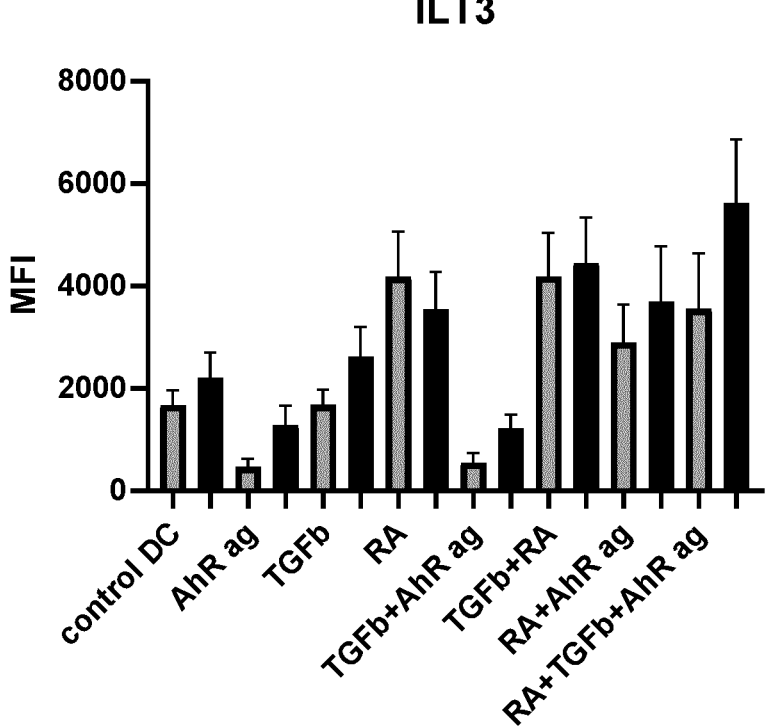
(D)
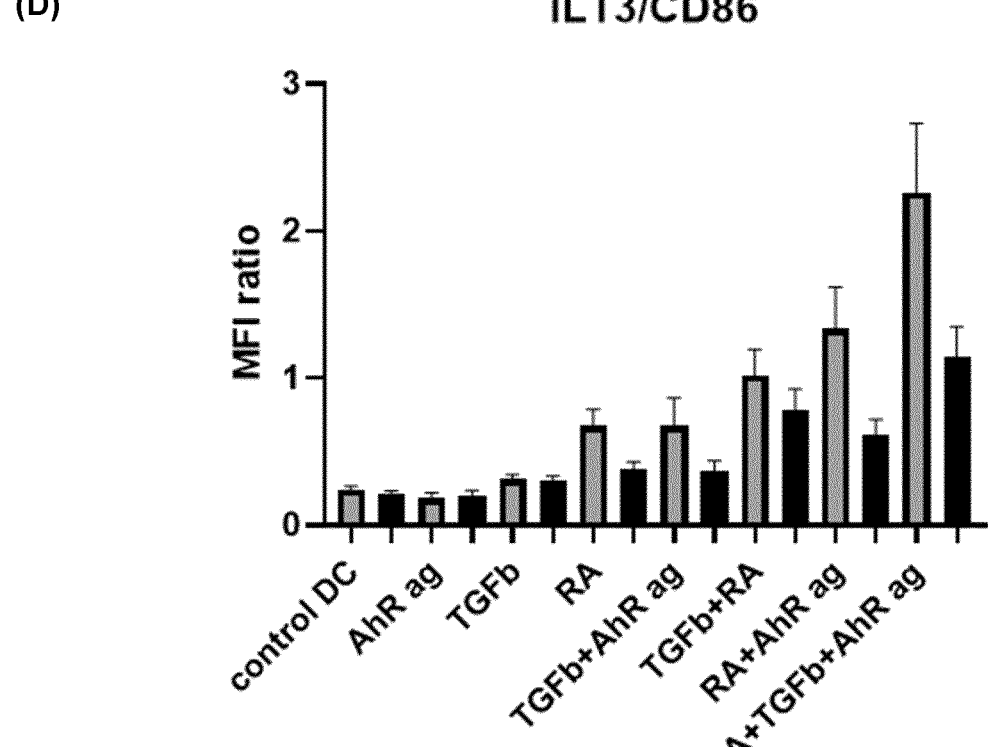

(E)

(F)

(G)

(H)

(A)

(B)

(C)

(D)

(E)

(F)

(G)

(A)

Antigen loading - Day 3 to 7

(B)

Antigen loading - Day 3 to 7

(C)

(D)

(E)

(F)

(G)

CD103

(H)

GARP

(I)

(A)

(B)

(C)

T cell activation

(A)

(B)

TOLEROGENIC ANTIGEN PRESENTING CELLS

This patent application claims a benefit of priority to PCT International Application PCT/EP2020/085857 filed 11 Dec. 2020; which claims a benefit of priority to GB Patent Application 1918364.9 filed 13 Dec. 2019; each of which is herein incorporated by reference in its entirety for all purposes.

FIELD OF THE INVENTION

The invention relates inter alia to an ex vivo method of obtaining tolerogenic antigen presenting cells (APCs) that have the capability to tolerise to an antigen, tolerogenic APCs obtained by the methods of the invention, tolerogenic APCs per se, and their use and methods of treating unwanted immune reactions to antigens and preventing immune rejection of an allograft.

BACKGROUND OF THE INVENTION

Tolerogenic antigen presenting cell (APC)-based immune therapies that exploit mechanisms of antigen presentation in a tolerogenic manner represent a promising non-toxic method for treating immune disorders or preventing graft, e.g. allograft, rejection. They may be used as a sole treatment or as an addition to other types of therapies such as in combination with immunosuppressive drugs or other immune modulating therapies. The strategy is based on ex vivo manipulation and introduction of cellular therapeutic products to circumvent immune disorders for the purpose of inducing antigen-specific tolerance. Thus, the ultimate goal of such APC based immune therapies is the induction of tolerance in the form of delivering an inhibitory signal to effector cells and induction and expansion of regulatory T cells (Tregs) in vivo. For example, patients with autoimmune diseases such as Type 1 diabetes, rheumatoid arthritis and multiple sclerosis, may benefit from treatment based on such tolerogenic APC-based therapies.

Induction of antigen-specific immune responses requires the engagement of professional APCs expressing major histocompatibility complex (MHC) molecules as well as membrane-bound co-stimulatory and secreted pro-inflammatory molecules. Furthermore, such APCs must be able to take up, process and present antigens in association with MHC molecules.

Similarly, induction of antigen-specific immune tolerance also requires the presentation of antigen in the context of MHC. However, unlike in the case of initiating an immune response, induction of tolerance requires low expression of membrane-bound co-stimulatory and secreted pro-inflammatory molecules in combination with high cell surface expression of tolerogenic molecules and secreted anti-inflammatory mediators.

The main types of professional APCs of the immune system are dendritic cells (DCs), macrophages, certain B cells and certain activated epithelial cells. At their immature stage, APCs take up extracellular antigens by means of phagocytosis or pinocytosis and process the antigens to peptides in the endocytic compartments such as endosomes and phagosomes, where peptides are bound to MHC class II molecules. They also have the unique ability of loading the peptides from exogenous proteins to the MHC class I pathway of presentation, a process called "cross-presentation". Given the appropriate differentiation signals, APCs may develop into tolerogenic or non-tolerogenic APCs.

Tolerogenic APC are able to mediate downregulation or prevention of an immune response and are thought to play a crucial role in the maintenance of peripheral tolerance.

Haemophilia A (HA) is an X-chromosome linked bleeding disorder caused by a variety of mutations in the F8 gene encoding Factor VIII (FVIII) that interfere with the expression or pro-coagulant function of the translated protein. FVIII is expressed primarily in liver and endothelial vascular beds. Lacking sufficient pro-coagulant activity, HA patients are prone to bleeding episodes and their sequelae, including increased morbidity and mortality. The FVIII database currently identifies 2,015 unique FVIII variants based on 5,472 individual case reports. This vast array of point mutations (66.5%), deletions (23.2%) and others (duplication, polymorphism, insertions, indel and complex) leads to a variety of clinical outcomes. Patients can be treated acutely (on-demand) or prophylactically with either plasma-derived or recombinant FVIII.

A significant number of patients develop neutralizing antibodies to FVIII, termed "inhibitors" or anti-drug antibodies (ADA), which block the activity of the administered FVIII, since their immune systems have not been rendered fully tolerant to certain sequences of normal FVIII. Inhibitor development is currently a severe and the most significant treatment complication seen in patients with HA.

At present, once inhibitors form, the only proven method for eradication is immune tolerance induction (ITI) through frequent high dose FVIII infusions, but this treatment strategy fails in 20-40% of patients.

The problem of ADAs is not limited to haemophiliacs with a defective FVIII expression. ADAs can develop in subjects treated with other biological drugs. ADA development is a T cell dependent process resulting from lack of central T cell tolerance. Tolerance to self-proteins is a vital part of immune system development, and proteins encountered later in life are usually recognized as foreign depending on the context in which they are presented culminating in the development of an antibody response.

It is believed that the first step of an immune response against FVIII is uptake of FVIII by APCs. Following endocytosis of FVIII by the APCs, FVIII is processed into small peptides which are loaded on MHC class II molecules and then the MHC class II-peptide complexes are transported to the cell surface for presentation to FVIII-specific CD4$^+$ T cells. The activation of these T cells requires additional activating signals provided by the APC. These activating signals are membrane-associated interactions between co-stimulatory molecules such as CD40, CD80 and CD86 on the plasma membrane of the APC and e.g. CD28, CD154 and CTLA-4 on the T cell. In addition to these receptor/ligand interactions, the APC signals to T cells via secreted cytokines such as IL-12 or IL-10. The combination of signals determines the direction into which the activated T cell differentiates. T helper 1 (Th1) cells generally induce a cytotoxic immune response, Th2 cells induce a B-cell mediated antibody response, while Tregs are able to induce immunosuppression/tolerance by suppressing activated B and T cells as well as through other mechanisms. Ultimately, the activated FVIII-specific T cells are able to activate FVIII-specific B cells and induce affinity maturation and class-switching of immunoglobulin genes in B cells. As a result, anti-FVIII antibody-secreting plasma cells and circulating FVIII-specific memory B-cells are generated, which produce antibodies upon re-exposure to FVIII.

Autoimmune disease occurs when a specific adaptive immune response erroneously is mounted against self-antigens. The consequence is that the effector pathways of immunity cause chronic inflammatory injury to tissues, which may prove lethal. Autoimmunity may be initiated by the activation of self-antigen-specific T cells and by production of autoantibodies. Specific genes found within the MHC, as well as at other immunoregulatory loci, play key roles in determining the susceptibility of individuals to develop autoimmune diseases, likely because of their ability to modulate adaptive T and B cell immune responses. T cell responses to self-antigens can inflict tissue damage through cytotoxic T cell responses, inappropriate activation of other effector cells, and inappropriate T cell help to B cells. Further, the immune system ceasing to recognise one or more of the body's normal constituents as "self" may lead to the production of pathological autoantibodies. Autoantibodies that recognise self-antigens as foreign mount a further immune response which leads to increased T cell infiltration, production of pro-inflammatory cytokines and extensive tissue damage. Diseases in which these actions of T cells and B cells are likely to be important include rheumatoid arthritis, type 1 diabetes mellitus and multiple sclerosis.

Transplants that are from a genetically unrelated donor of the same species are termed allografts. Allogeneic transplantation is deemed the last resort for the treatment of chronic organ failure. Even with the aid of organ preservation and the advances in immunosuppression, the major complication post-transplantation is rejection. Rejection occurs despite pre-transplant tissue typing/blood analysis and is seen in almost all transplant recipients, to varying degrees. Outside hyperacute rejection, which occurs due to the presence of pre-existing antibodies (resulting from pregnancy, blood transfusions and/or previous transplants), transplant rejection can be split broadly into two types; acute and chronic. Acute rejection is thought to be solely an immunological response, whereas chronic rejection involves both immunologic and non-immunologic mechanisms.

Allorecognition is the presentation of graft antigen (alloantigen) and is divided into two main subtypes: direct and indirect. DCs and other professional APCs migrating from the graft initiate direct allorecognition, where recipient T cells are activated by allogeneic MHC associated peptides directly. Later, recipient APCs pick up alloantigen, shed by the graft or dying cells of donor origin, and present processed allogeneic peptides to recipient T cells in association with self-MHC (indirect allorecognition). A third subtype, semidirect allorecognition, involving the recipient APCs passively acquiring donor MHC to their cell surface through a process called trogocytosis while patrolling the graft, has also been proposed. Naïve CD4$^+$ T helper cells are one of the first immune cells to be activated post-transplantation, playing a key role in rejection. Activated naïve CD4$^+$ T helper cells develop into either Th1 (pro-inflammatory) or Th2 (anti-inflammatory) subtypes. Each subtype orchestrates a characteristic immune response profile (each being mutually suppressive). In the presence of transforming growth factor beta (TGFbeta) and IL-6, naïve CD4$^+$ T helper cells can differentiate into Th17 cells, a subset of Th cells that secretes IL-17, which is further stimulated by IL-23.

Ex vivo generated APCs with appropriate tolerogenic functions could be implemented as a therapeutic treatment of anti-drug reactions, autoimmune diseases and for induction of transplant tolerance. Efficient suppression of harmful immune responses involves tolerance induction in both CD4$^+$ and CD8$^+$ T cells. Therefore, one can expect that ex vivo generated tolerogenic APCs should have the same characteristics for treating anti-drug reactions, autoimmune diseases and for prevention of graft rejection in vivo.

The vitamin A metabolite retinoic acid plays an important role in cell growth, differentiation, organogenesis, and reproduction and a key role in mucosal immune responses. Retinoic acid has been reported to enhance the differentiation of Foxp3$^+$ inducible as well as IL-10 producing Treg cells, and to induce gut-homing specificity in T cells (Bakdash et al, 2015). In addition, due to its regulatory activity, retinoic acid has been reported to play an important role in the control of inflammatory diseases not only in the intestine but also in other tissues (Oliveira et al, 2018).

Transforming growth factor beta (TGFbeta) is a pleiotropic cytokine present in vertebrate and invertebrate organisms that functions in numerous physiological and pathological processes. TGFbeta impacts all the cells of the immune system, and of the three known TGFbeta isoforms, TGFbeta1 is the predominant isoform expressed in immune cells. TGFbeta1 is known to play a pivotal role in the function of all immune cells especially in the regulation of T cell development and in the induction of immunological tolerance in DCs. DCs regulate immune functions, including immune suppression, by secreting TGFbeta (Esebanmen et al, 2017).

The aryl hydrocarbon receptor (AhR) is a transcription factor activated by several exogenous and endogenous ligands. Among several physiologic effects, AhR contributes to immune homeostasis, by promoting immunoregulatory effects. Activation of the AhR through agonistic ligands such as 6-formylindolo(3,2b)carbazole (FICZ) during DC differentiation and maturation processes has been shown to lead to increased expression of the enzyme IDO and a reduced production of pro-inflammatory cytokines such as IL-6 and TNF-alpha. A study has shown that FICZ-treated DCs were able to induce the differentiation of naïve T cells into CD4$^+$CD25$^{high}$ Foxp3$^+$ Treg cells demonstrating that the activation of the AhR in human DCs promotes a tolerogenic phenotype (Jurado-Manzano et al, 2017).

There is a need to provide alternative methods for the generation of tolerogenic APCs having distinct tolerogenic phenotypes that are useful in the treatment of unwanted immune reactions to biological drugs such as Factor VIII to autoantigens in autoimmune diseases and to alloantigens in transplanted grafts.

SUMMARY OF THE INVENTION

The inventors of the present application have surprisingly identified a specific cell culture method involving use of specific combinations of retinoic acid, TGFbeta and AhR agonists which advantageously allows for the generation of tolerogenic APCs with a unique profile derived from a starting cell population of monocytes.

The inventors have discovered that tolerogenic APCs can be generated by a method comprising culturing monocytes in a cell culture comprising a specific combination of components.

Advantageously, it is expected that the tolerogenic APCs obtained by the method of the invention may be used for targeted immune therapy where a mammalian subject has or is at risk of an unwanted immune reaction to an antigen. The antigen may, for example, be a biological drug or a self-antigen. Further, it is expected that the tolerogenic APCs obtained by the method of the invention may be used to prevent immune rejection of an allograft in a recipient subject.

Thus, in a first aspect of the invention, there is provided an ex vivo method of obtaining tolerogenic APCs that have the capability to induce tolerance to an antigen, the method comprising, (a) isolating monocytes from a sample obtained from a mammal; and (b) culturing the isolated monocytes in a cell culture to induce differentiation of the monocytes into APCs having a tolerogenic phenotype, wherein the cell culture comprises (i) retinoic acid and TGFbeta, (ii) retinoic acid, TGFbeta and an AhR agonist or (iii) retinoic acid and an AhR agonist.

In another aspect of the invention, there is provided a tolerogenic APC or population thereof obtainable or obtained by the method of the present invention.

In a yet another aspect of the invention, there is provided a tolerogenic APC or population thereof, wherein the cell or population when unstimulated or when stimulated e.g. with an immunogenic stimulus such as LPS, expresses CD103 and has high expression of CD141, GARP and ILT3 and low expression of CD83 and CD86.

In a further aspect of the present invention, there is provided a tolerogenic APC or population thereof according to the invention for use in a method of treating a mammalian subject with or at risk of an immune reaction to an antigen, wherein the method comprises administering the tolerogenic APCs to the mammalian subject thereby establishing immune tolerance to the antigen.

In yet a further aspect of the present invention, there is provided a tolerogenic APC or population thereof for use in a method of treating a mammalian subject with or at risk of an immune reaction to an antigen, wherein the method comprises (i) obtaining a tolerogenic APC or population thereof that has the capability to induce tolerance to an antigen according to the invention, wherein the tolerogenic APC or population thereof is obtained from a sample of isolated monocytes derived from the mammalian subject and (ii) administering the tolerogenic APC or population thereof back to the mammalian subject thereby establishing immune tolerance to the antigen.

In another aspect of the invention, there is provided a tolerogenic APC or population thereof according to the invention for use in a method of preventing immune rejection of an allograft in a recipient subject, wherein the allograft is derived from a donor, wherein the method comprises administering the tolerogenic APCs to the recipient subject thereby establishing tolerance to the allograft, wherein the tolerogenic APCs are obtained from monocytes isolated from a sample taken from the donor.

In yet another aspect of the invention, there is provided a tolerogenic APC or population thereof according to the invention for use in a method of preventing immune rejection of an allograft in a recipient subject, wherein the allograft is derived from a donor, wherein the method comprises administering the tolerogenic APCs to the recipient subject thereby establishing tolerance to the allograft, wherein the tolerogenic APCs are obtained from monocytes isolated from a sample taken from the recipient.

6

Figure 2:
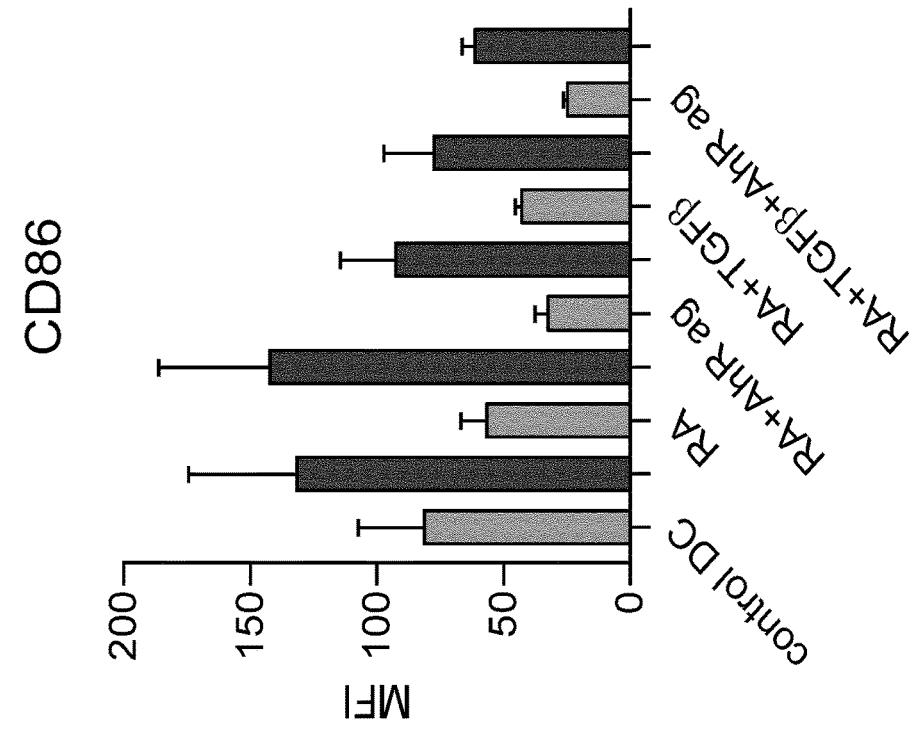
Figure 2:
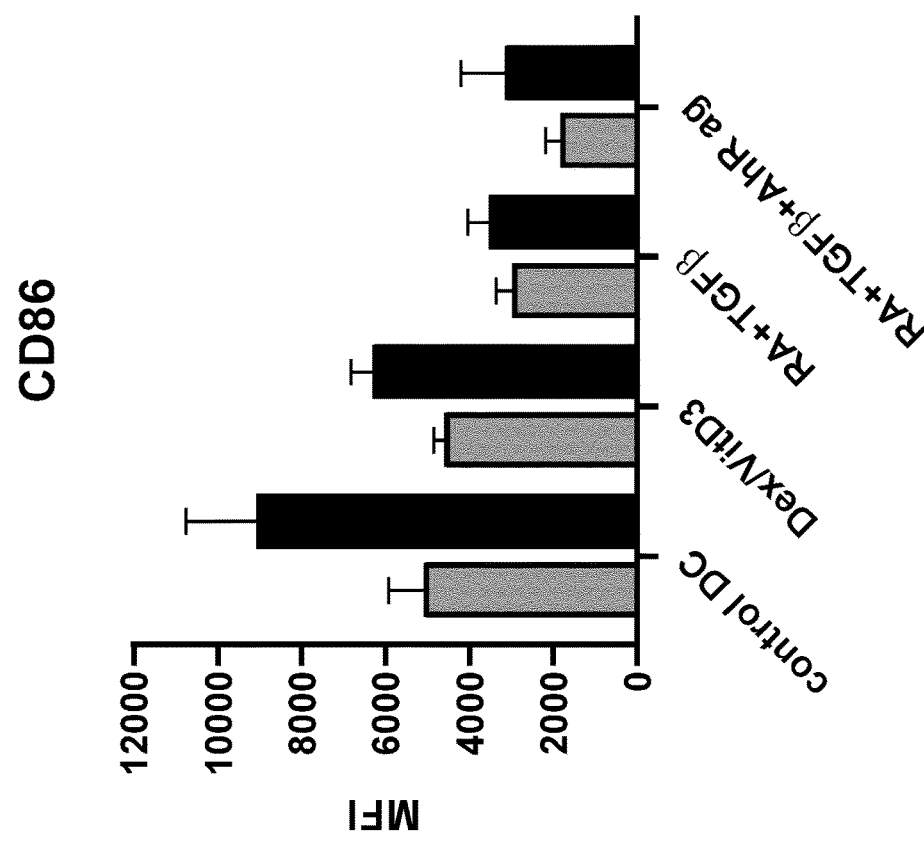

FIG. 2 shows the expression of the activation marker CD86 on DCs cultured under various conditions (FIGS. (A) and (B)). The DCs were unstimulated (grey bars) or stimulated (black bars) with LPS (see Example 2).

Figure 3:
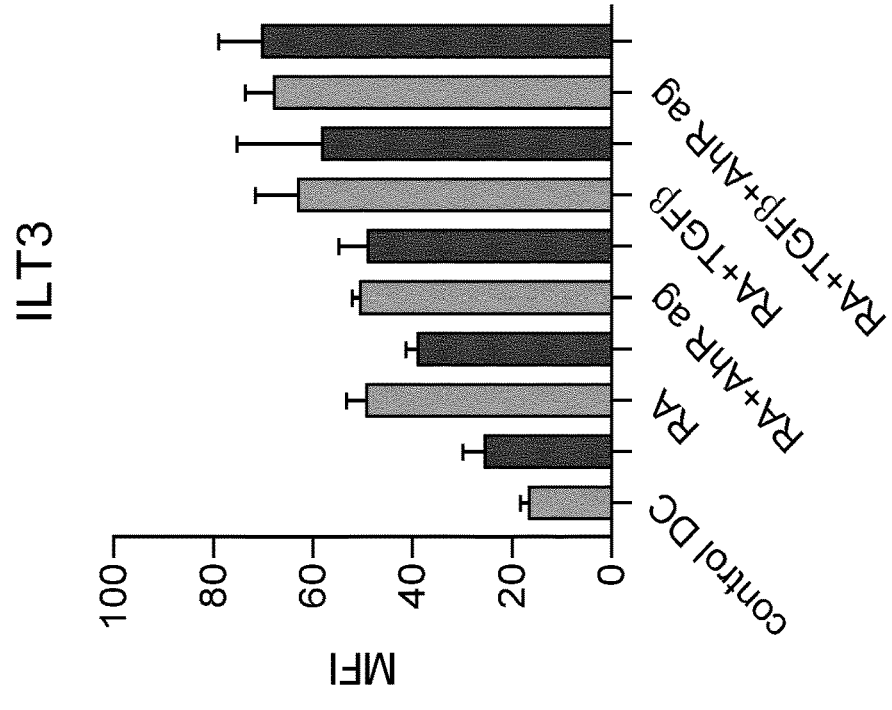
Figure 3:
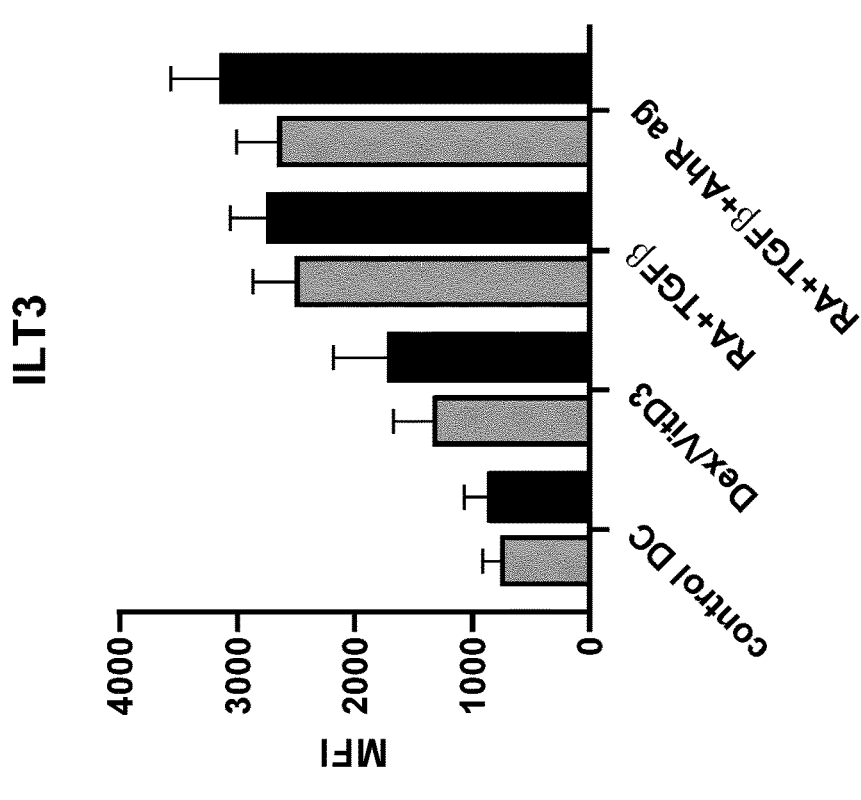

FIG. 3 shows the expression of the tolerogenic marker ILT3 on DCs cultured under various conditions (FIGS. (A) and (B)). The DCs were unstimulated (grey bars) or stimulated (black bars) with LPS (see Example 3).

Figure 4:
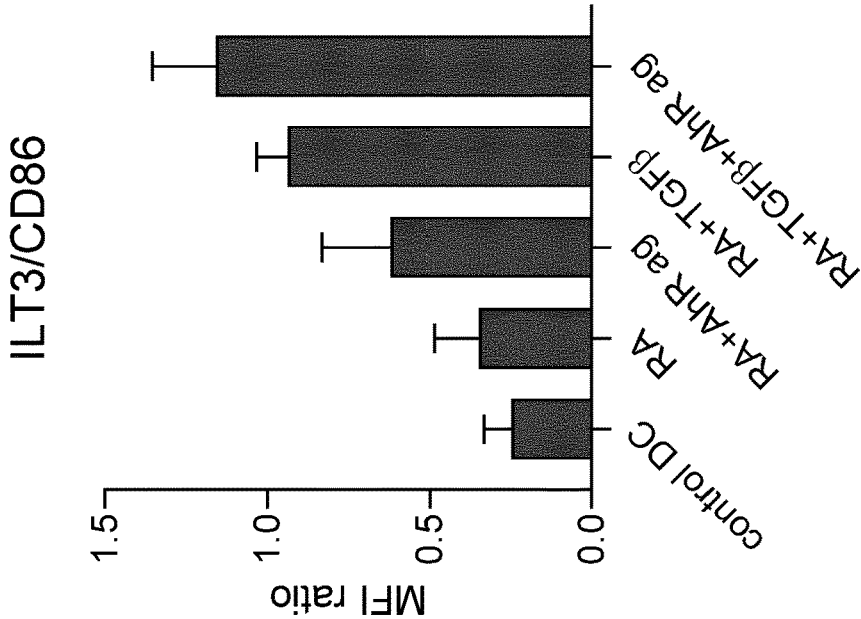
Figure 4:
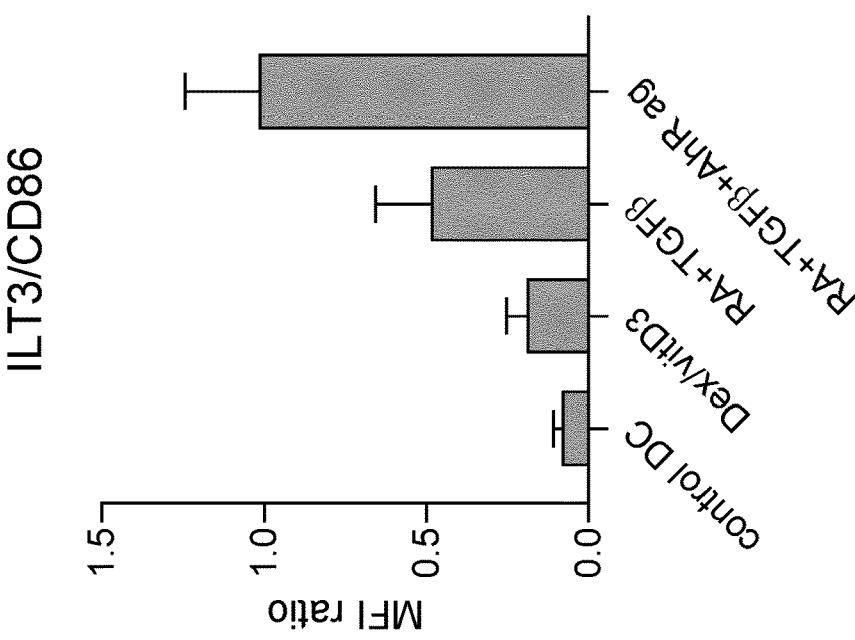

FIG. 4 shows the tolerogenic index, defined as the ILT3/CD86 expression (MFI) ratio on DCs cultured under various conditions. The DCs were unstimulated (FIG. (A)) or stimulated (FIG. (B)) with LPS (see Example 4).

Figure 5:
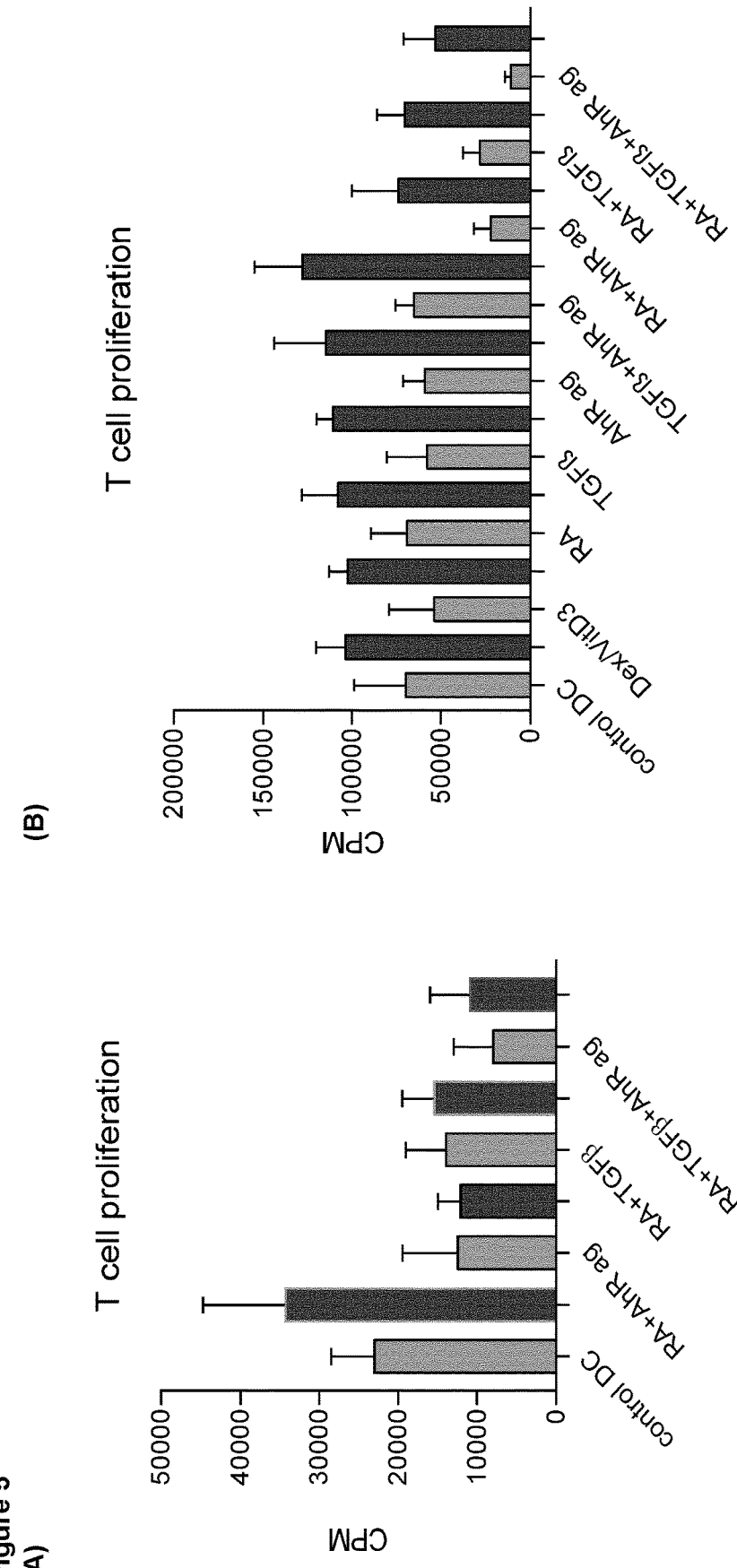

FIG. 5 shows the capacity of DCs to stimulate CD4$^+$ T cell proliferation in mixed lymphocyte reactions (MLR). The DCs were unstimulated (grey bars) or stimulated (black bars) with either LPS (FIG. (A)) or a pro-inflammatory cytokine cocktail (Figure (B)) before being co-cultured with the T cells (see Example 5).

Figure 6:
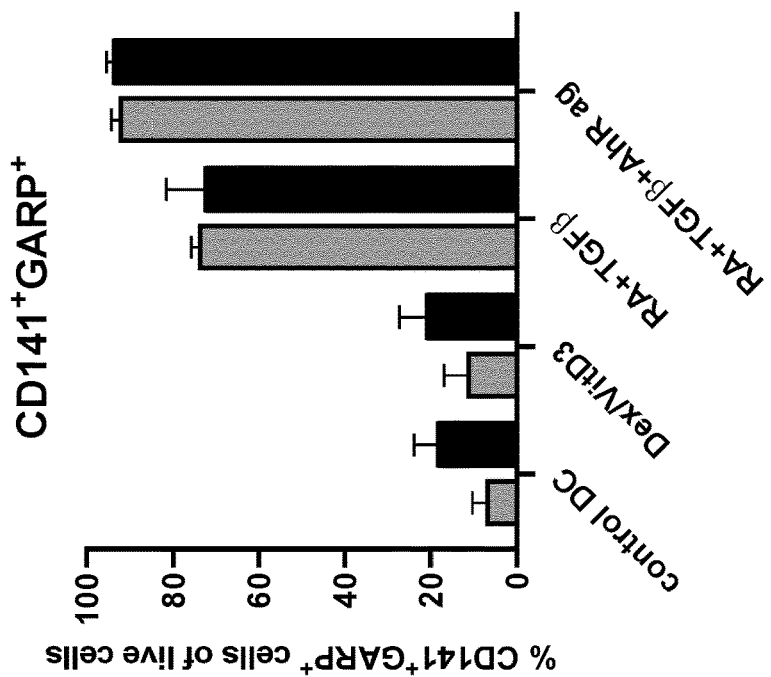
Figure 6:
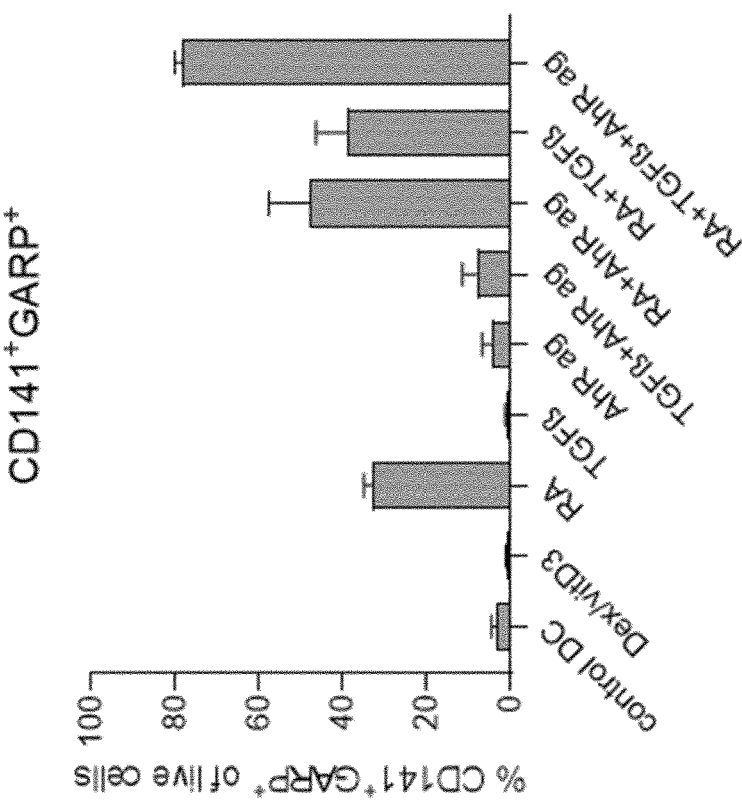

FIG. 6 shows the frequencies of CD141 and GARP co-expressing cells among DCs cultured under various conditions (FIGS. (A) and (B)). The DCs were unstimulated (grey bars) or stimulated (black bars) with LPS (see Example 6).

Figure 7:
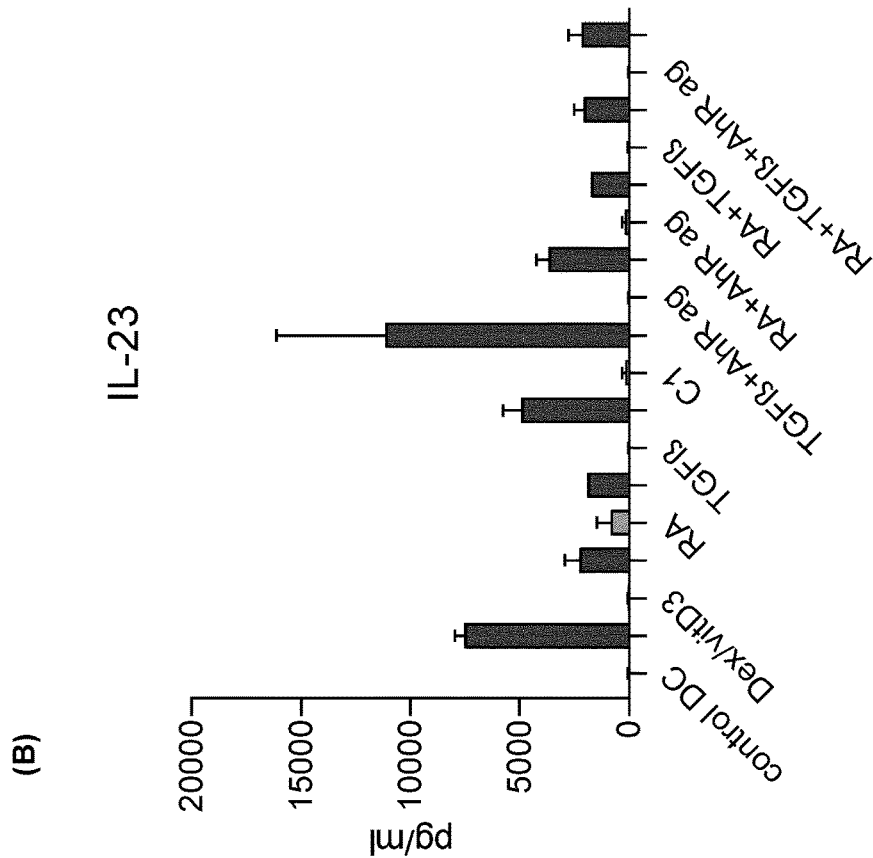
Figure 7:
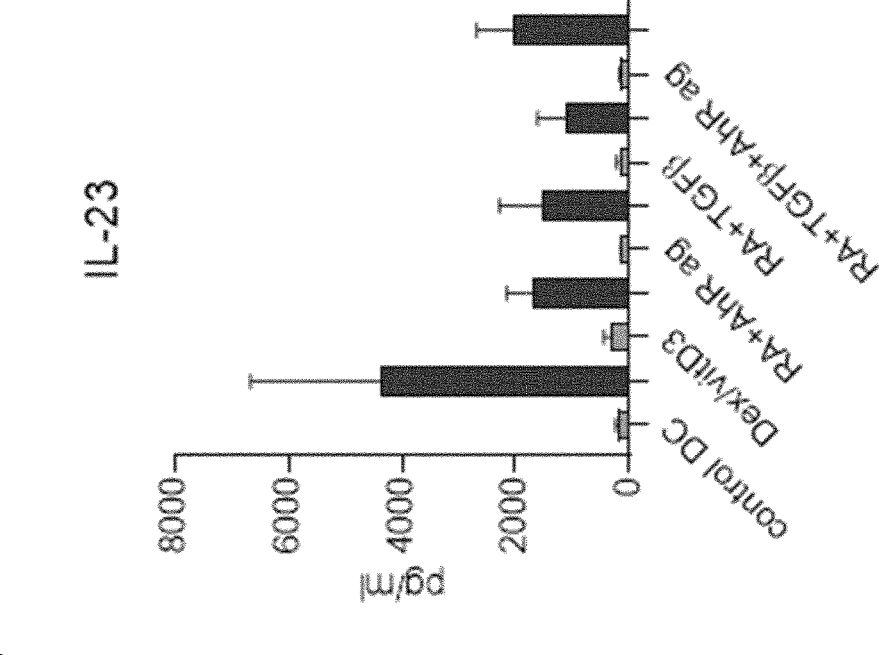

FIG. 7 shows the production of IL-23 by DCs cultured under various conditions (FIGS. (A) and (B)). The DCs were unstimulated (grey bars) or stimulated (black bars) with either LPS (FIG. (A)) or a pro-inflammatory cytokine cocktail (FIG. (B)) (see Example 7).

Figure 8:
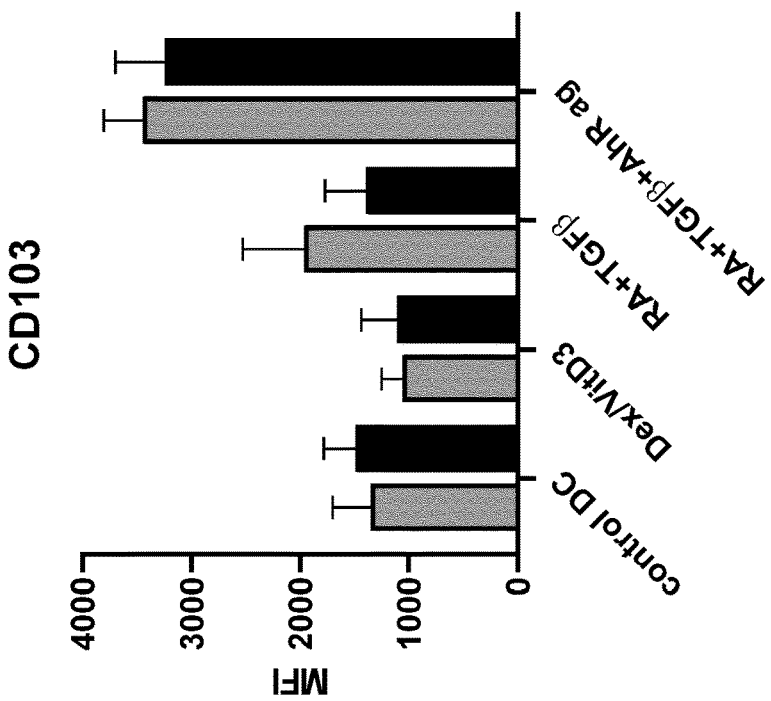
Figure 8:
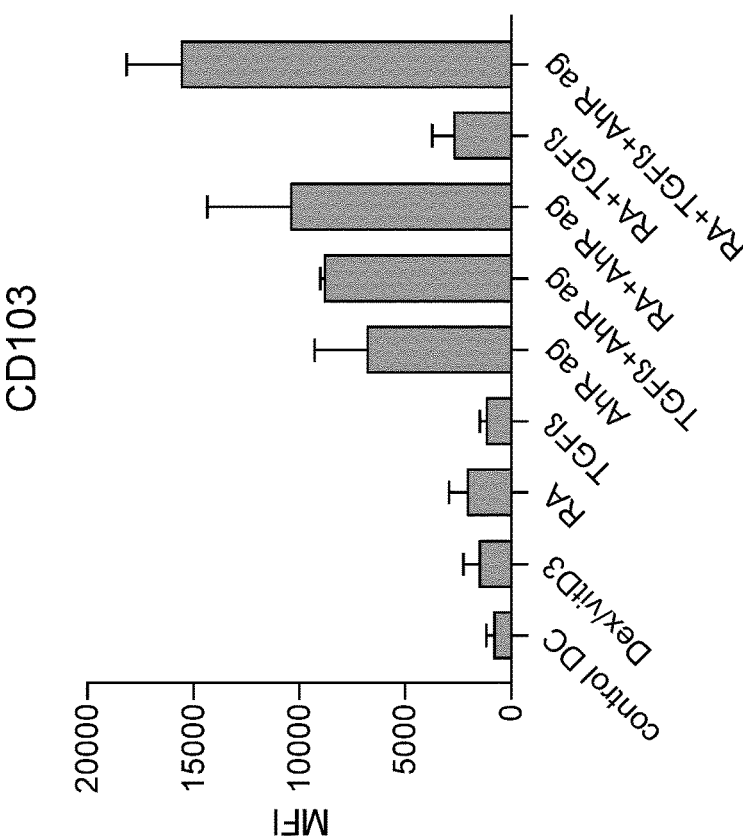

FIG. 8 shows the expression of the marker CD103 on DCs cultured under various conditions (FIGS. (A) and (B)). The DCs were unstimulated (grey bars) or stimulated (black bars) with LPS (see Example 8).

FIG. 9 shows the expression levels of the tolerogenic markers MERTK (Figure A), BTLA (FIG. B), LAP (FIG. C), HLA-G (FIG. D) and CD49b (FIG. E) on DCs cultured under various conditions (see Example 9).

Figure 10:
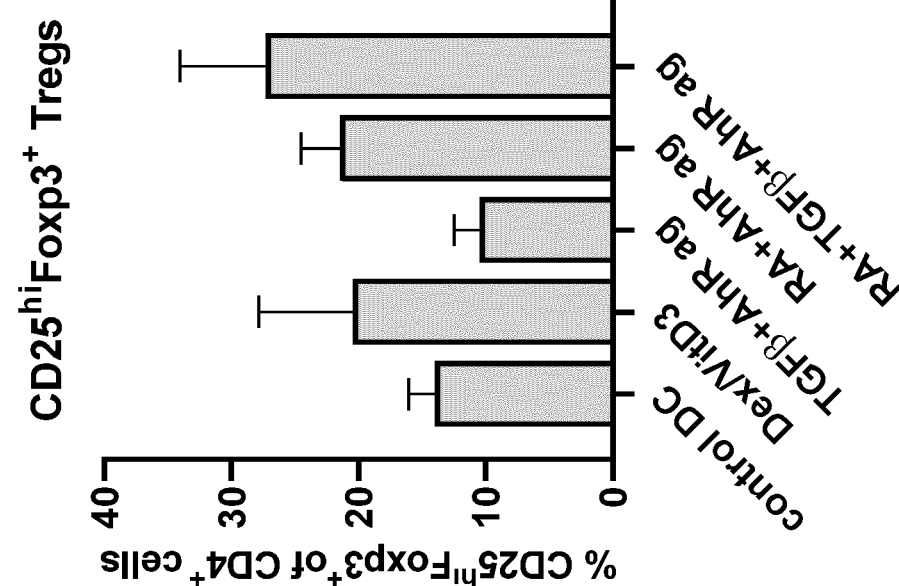
Figure 10:
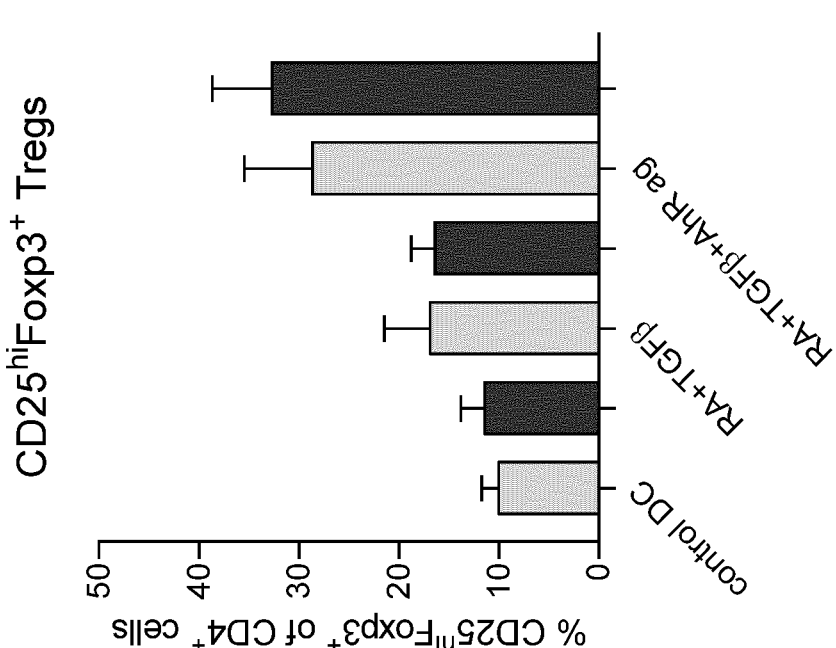

FIG. 10 shows the capacity of DCs to induce CD4$^+$CD25$^{hi}$Foxp3$^+$ Tregs in time-extended MLRs (FIGS. (A) and (B)). The DCs were unstimulated (grey bars) or stimulated (black bars) with LPS before being co-cultured with the T cells (see Example 10).

Figure 11:
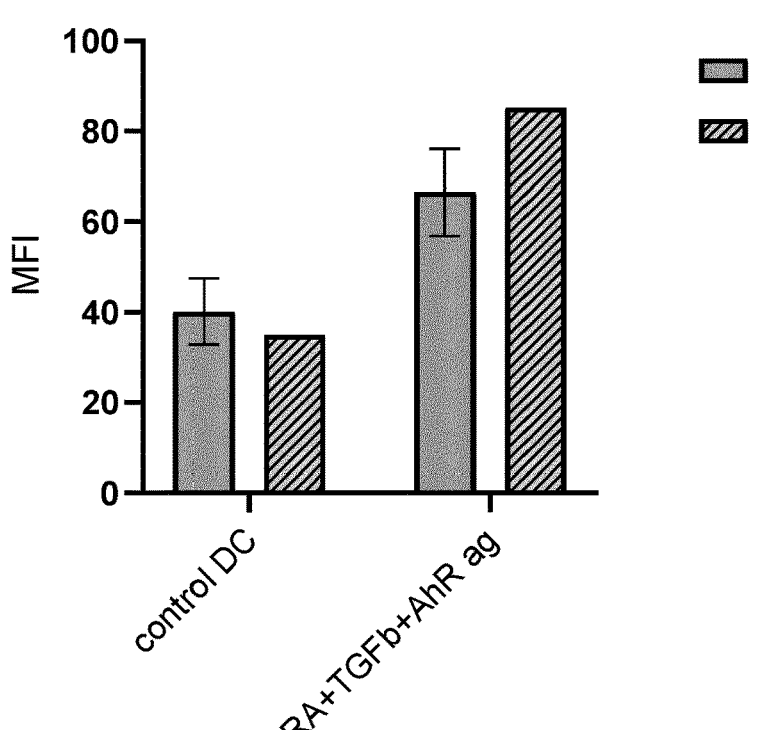
Figure 11:
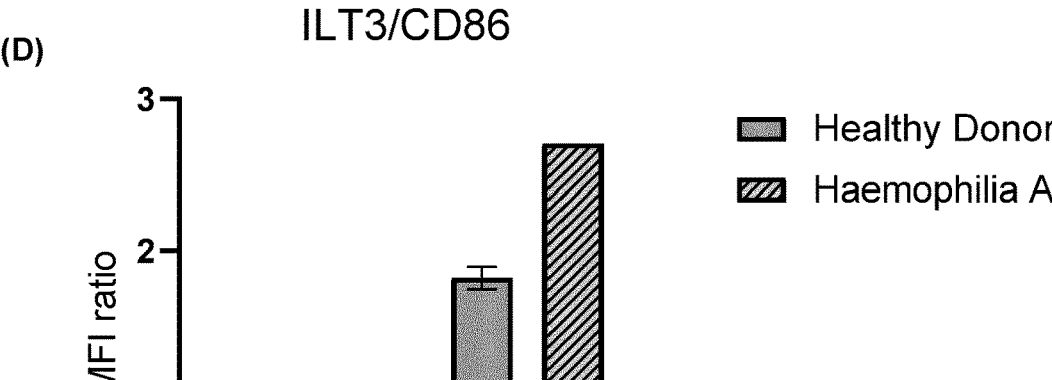
Figure 11:
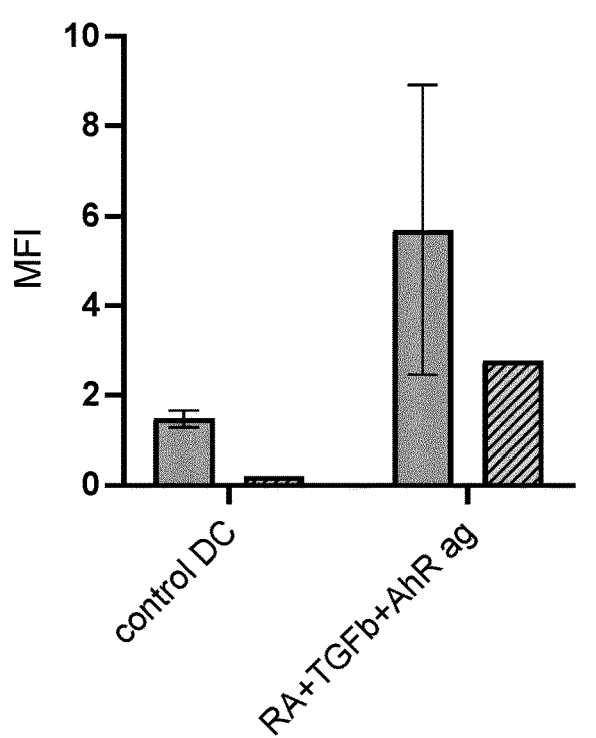
Figure 11:
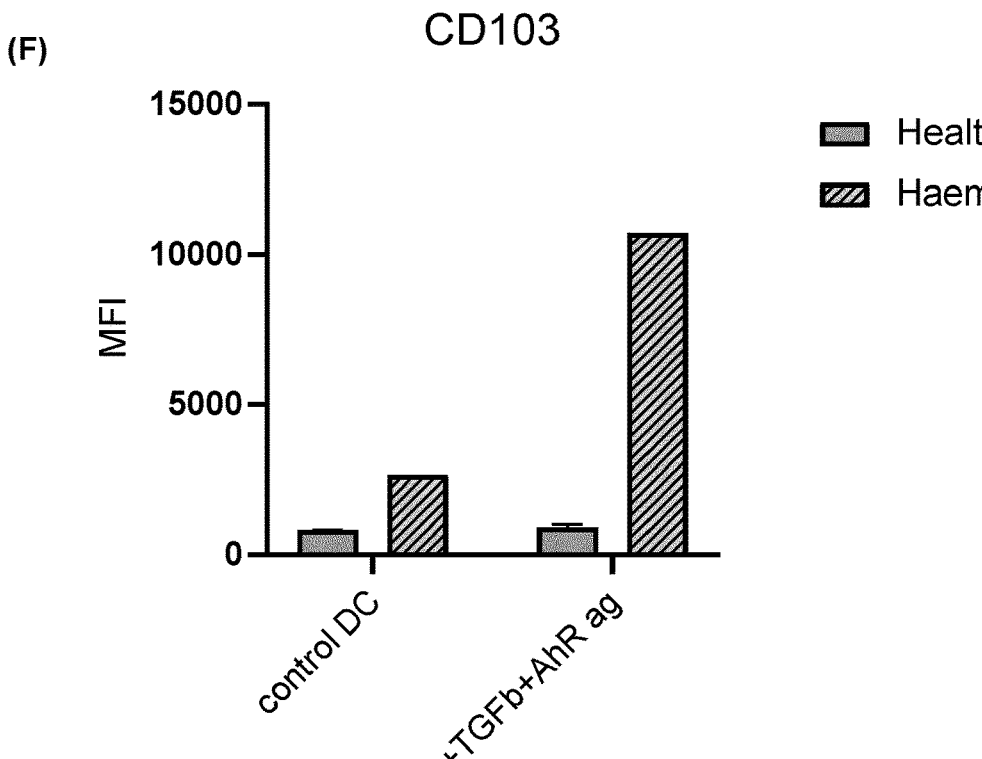
Figure 11:
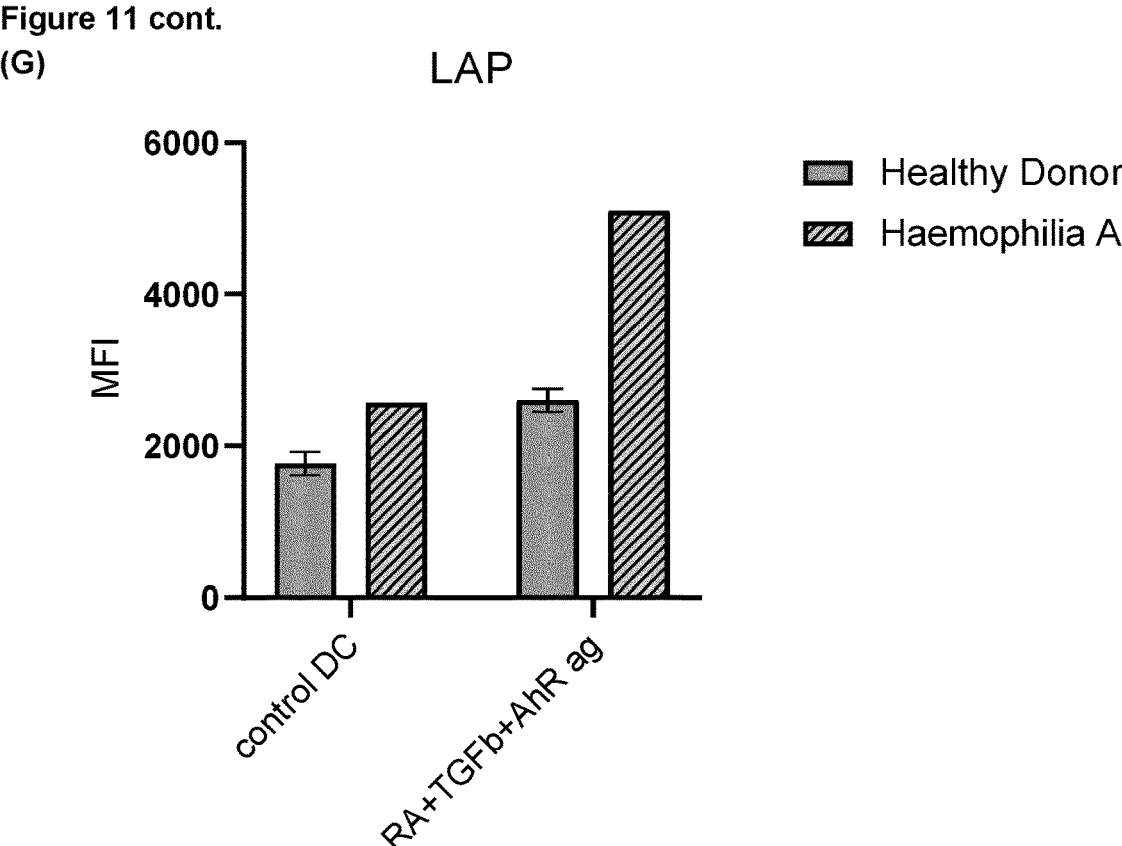
Figure 11:
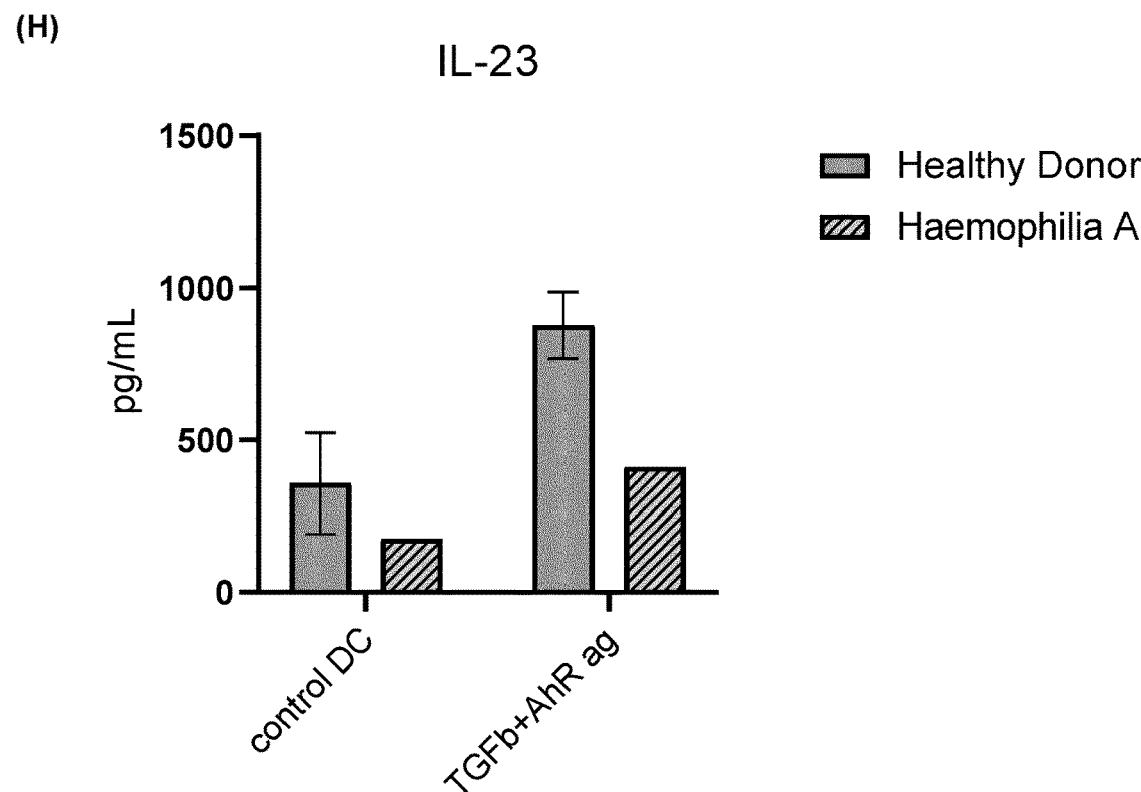
Figure 11:
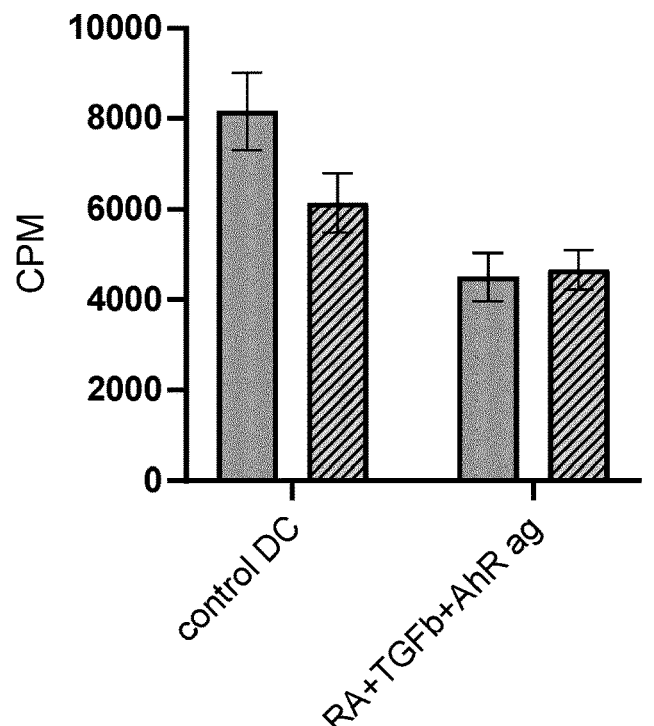
Figure 11:
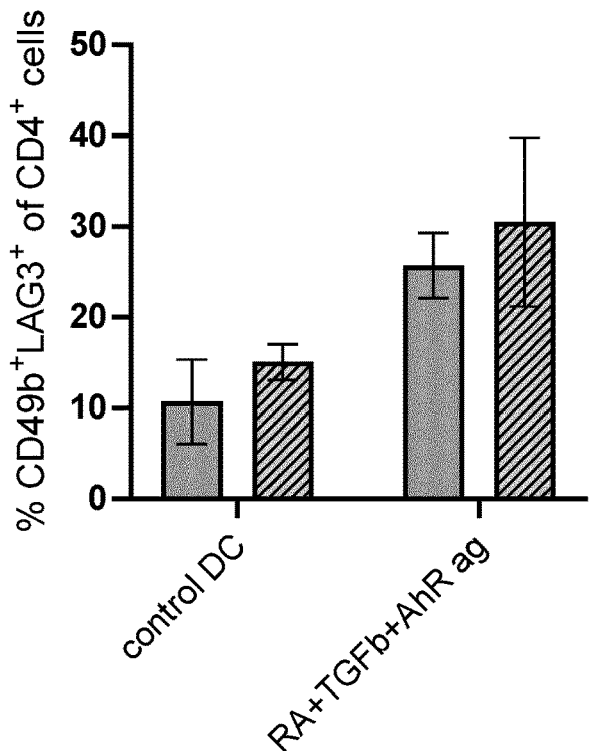

FIG. 11 shows the expression of the maturation marker CD83 (Figure A), the activation marker CD86 (FIG. B), the tolerogenic marker ILT3 (FIG. C), the tolerogenic index, defined as the ILT3/CD86 expression (MFI) ratio (FIG. D), the frequencies of CD141 and GARP co-expressing cells (FIG. E), the expression of the marker CD103 (FIG. F), the expression level of the tolerogenic marker LAP (FIG. G), the production of IL-23 (FIG. H), T cell proliferation (FIG. 1) and induction of CD4$^+$CD49b$^+$LAG3$^+$Tr1 cells (FIG. J) when DCs generated from CD14+ monocytes isolated from blood from a healthy donor (solid bars) or a haemophilia patient (striped bars) and cultured in the presence of RA+TGFb+AhR agonist. (see Example 11).

Figure 12:
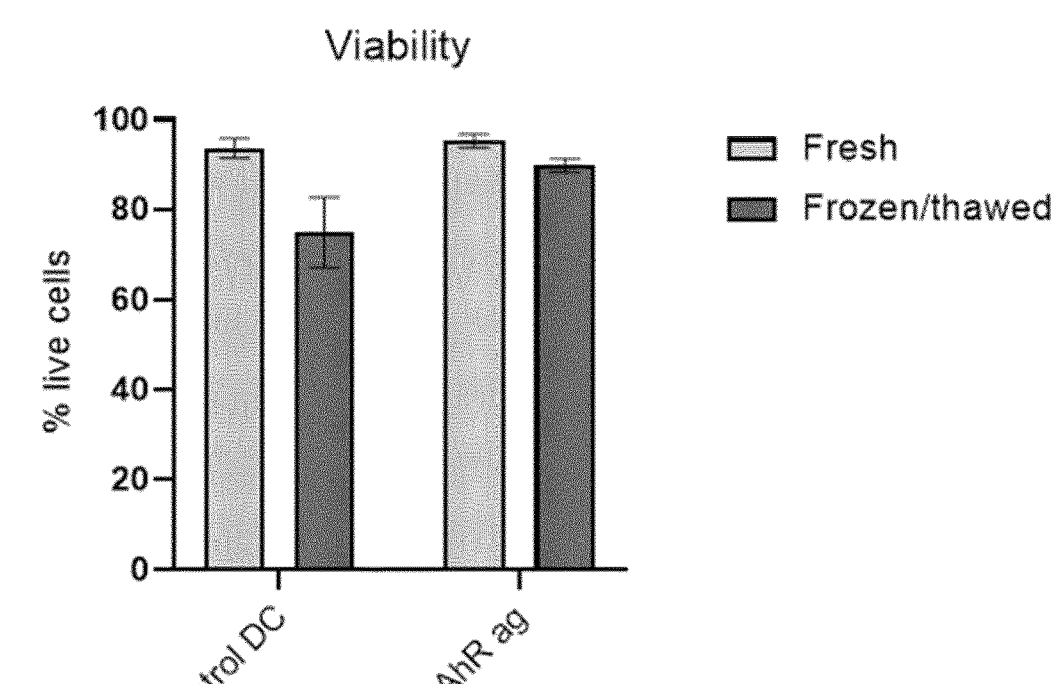
Figure 12:
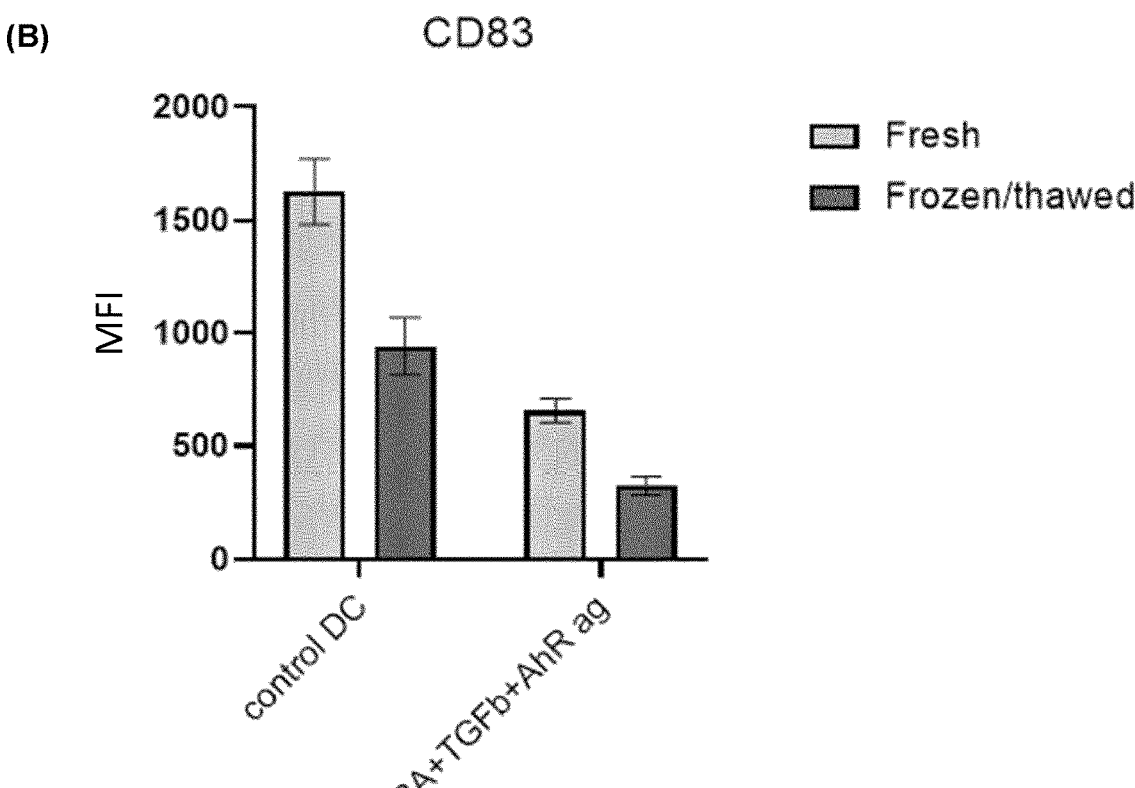
Figure 12:
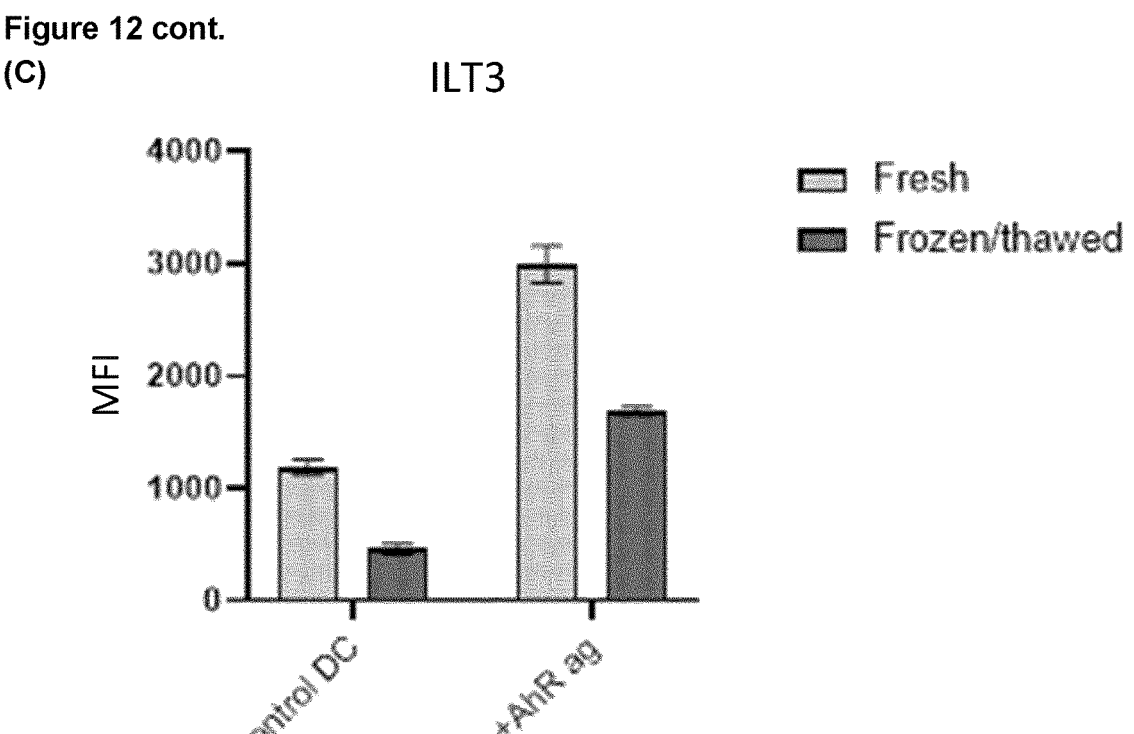
Figure 12:
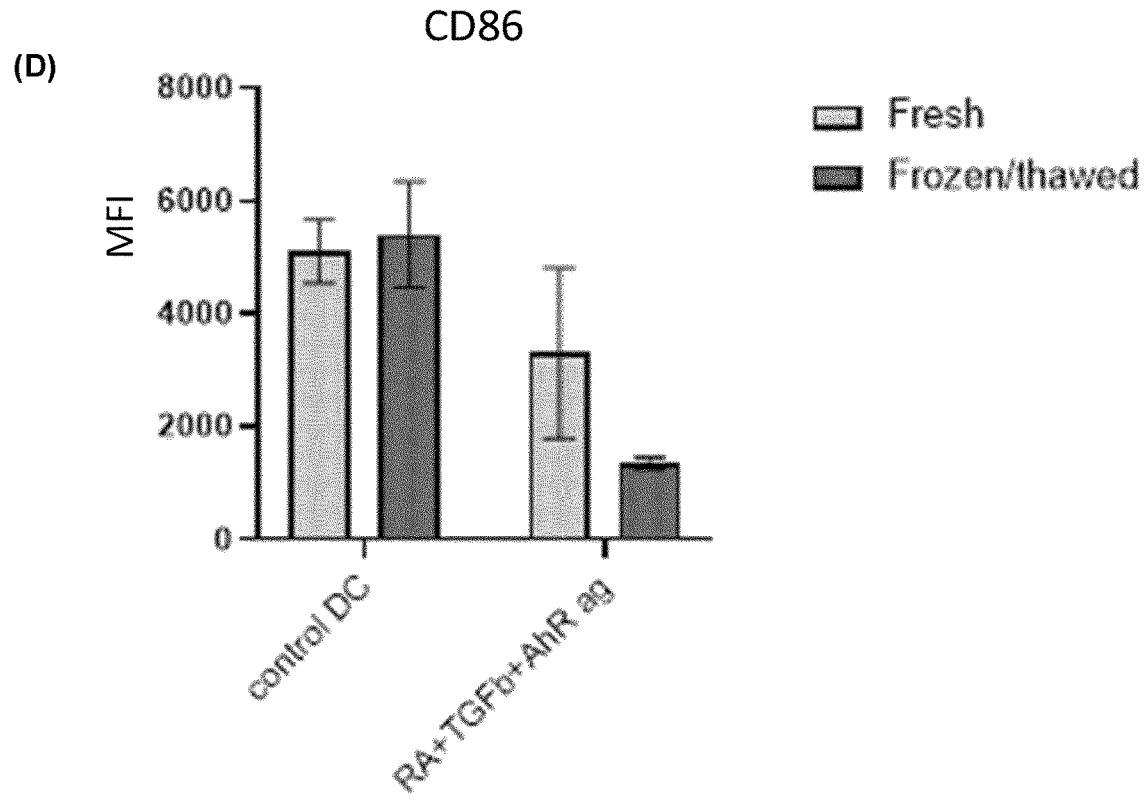
Figure 12:
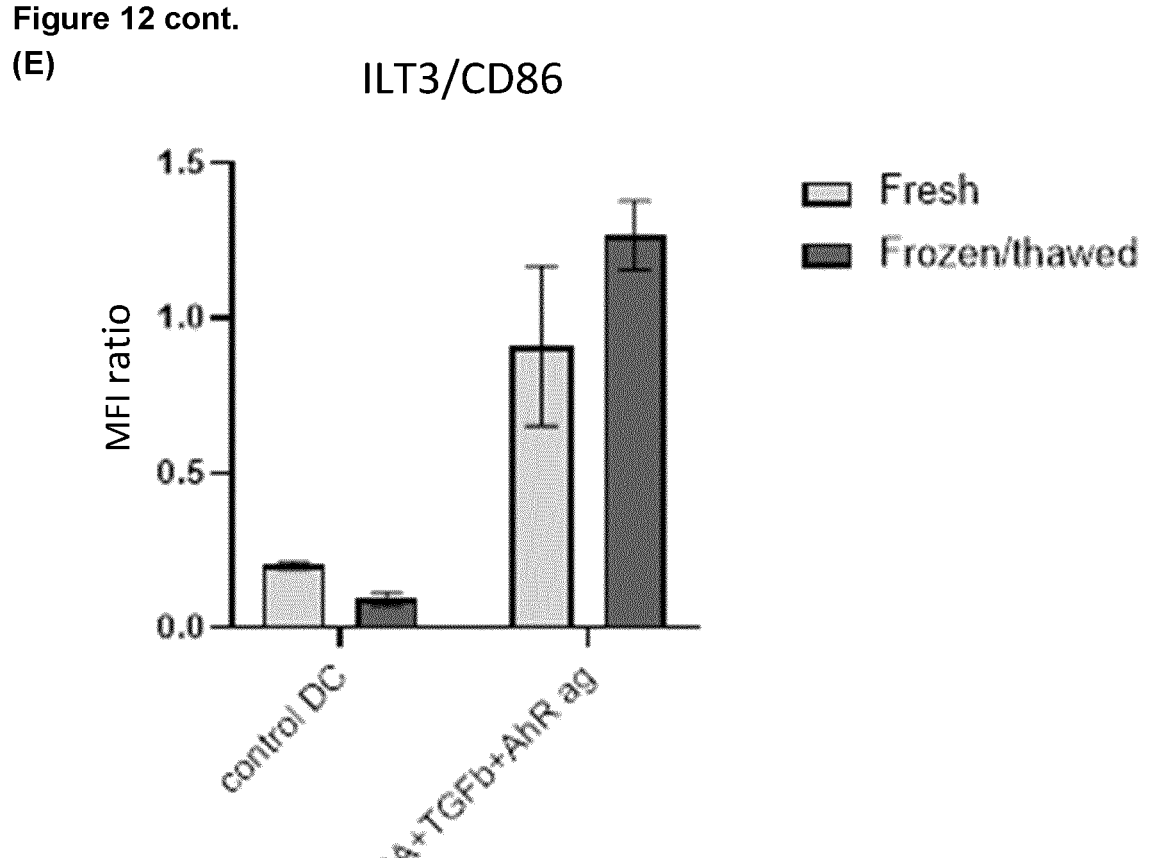
Figure 12:
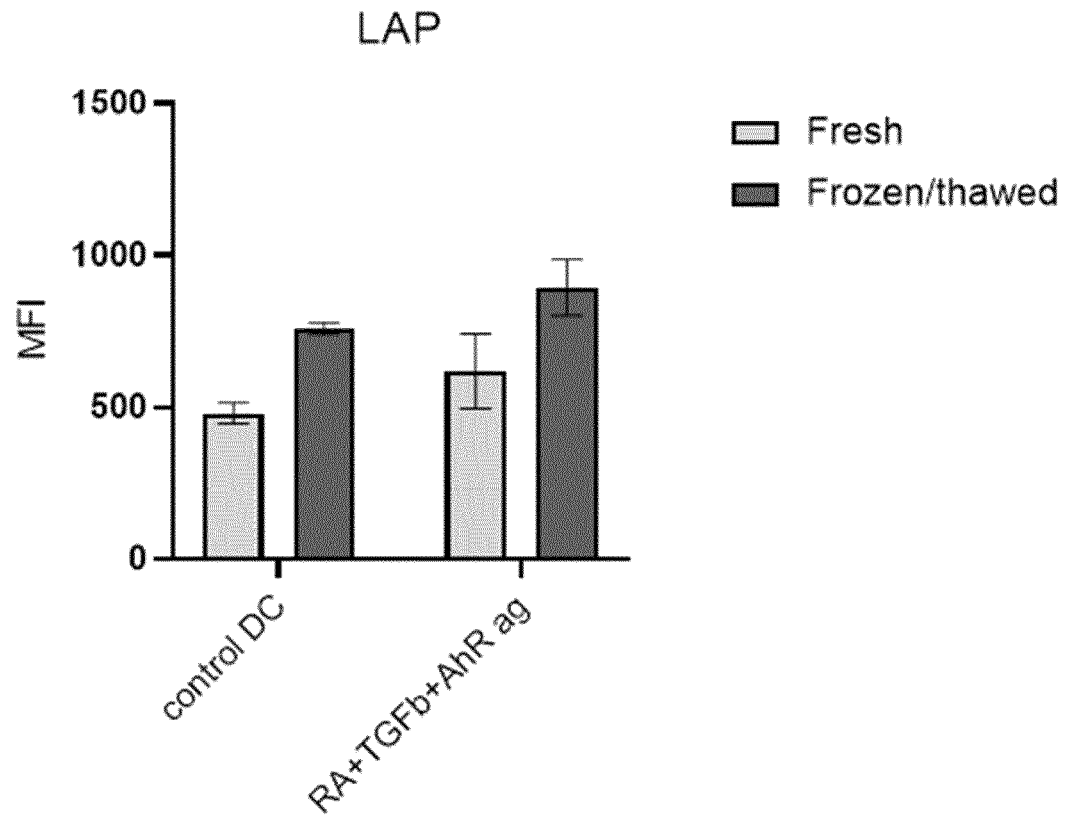
Figure 12:
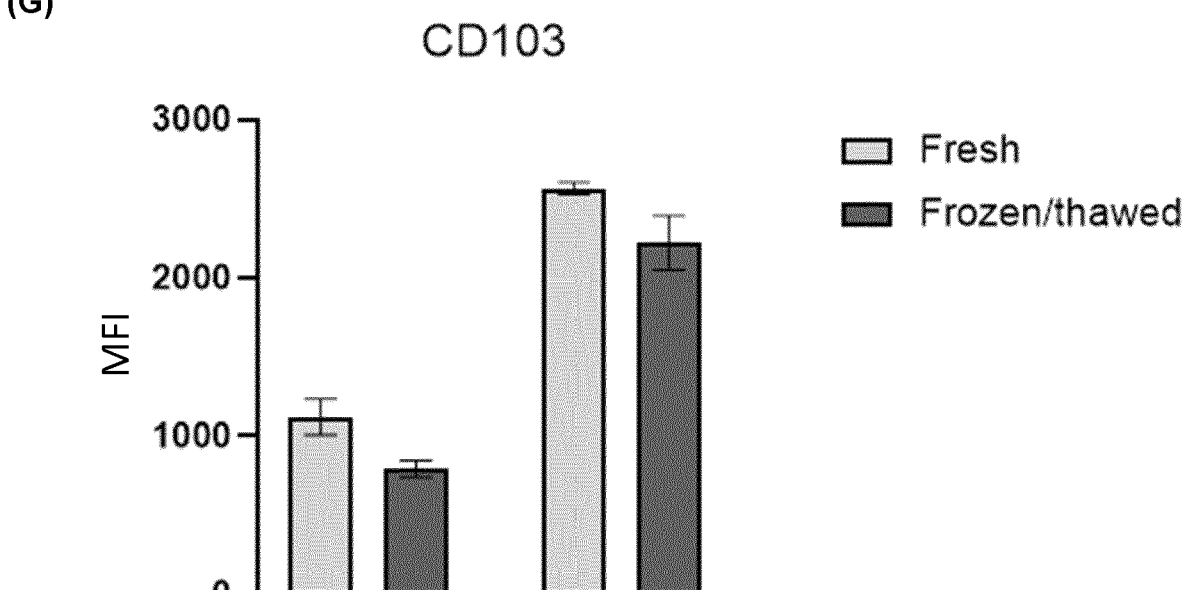

FIG. 12 shows the viability (FIG. A), expression of the maturation marker CD83 (FIG. B), the tolerogenic marker ILT3 (FIG. C), the activation marker CD86 (FIG. D), the tolerogenic index, defined as the ILT3/CD86 expression (MFI) ratio (FIG. E), the expression level of the tolerogenic marker LAP (FIG. F) and the expression of the marker CD103 (FIG. G) when DCs were cultured in the presence of RA+TGFb+AhR agonist and have undergone freeze/thaw (dark grey bars). The phenotype of the frozen/thawed cells was compared to fresh cells (light grey bars) (see Example 12).

Figure 13:
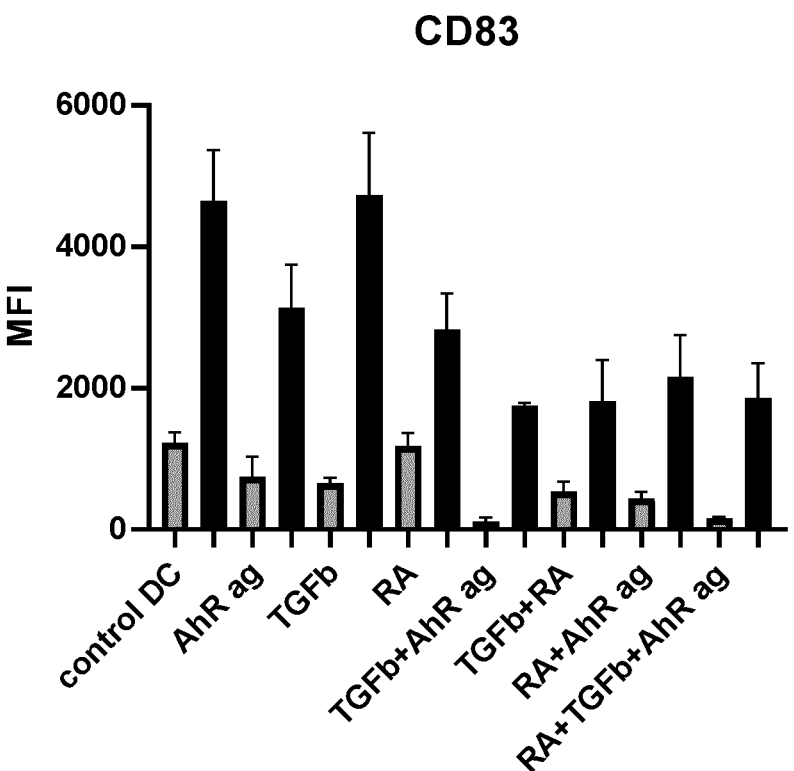
Figure 13:
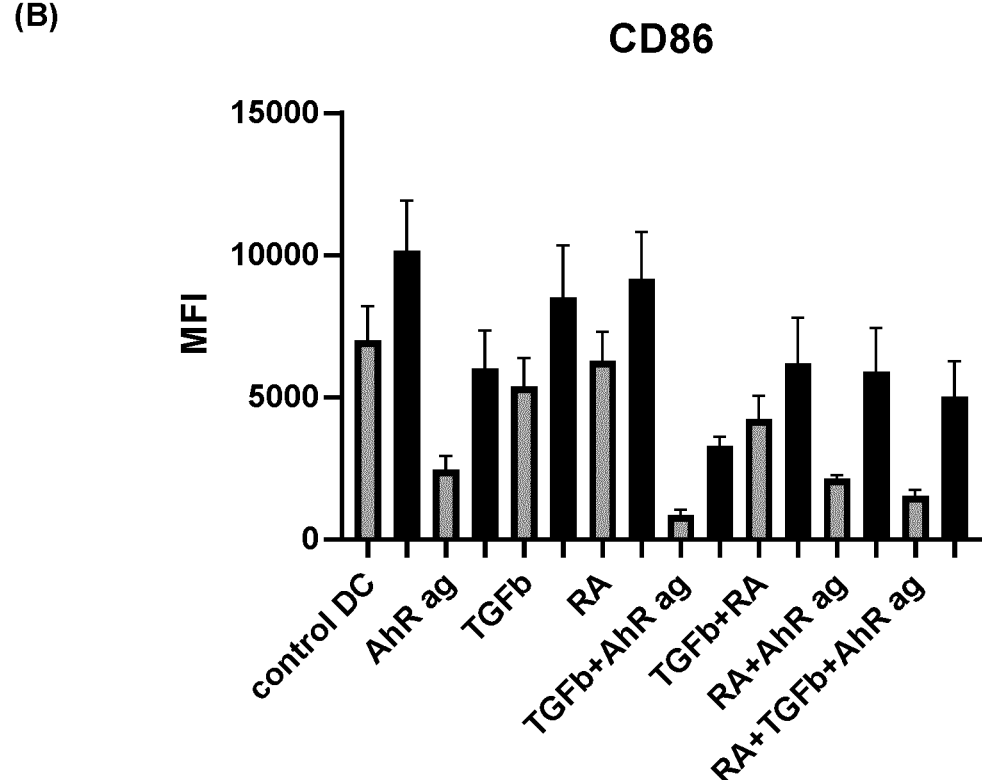
Figure 13:
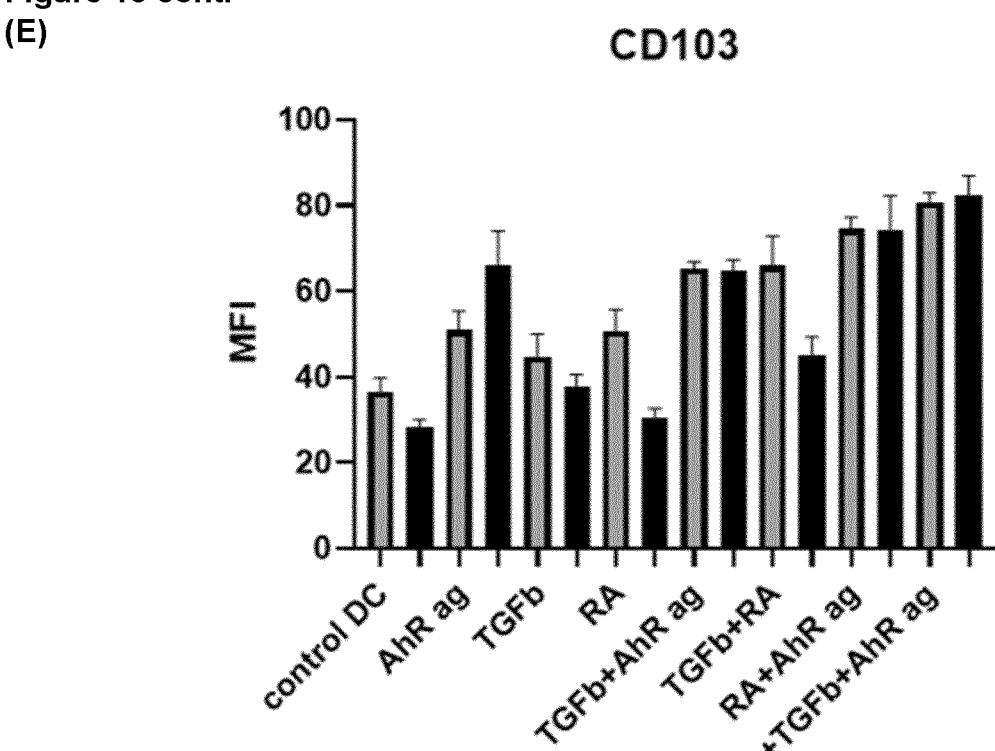
Figure 13:
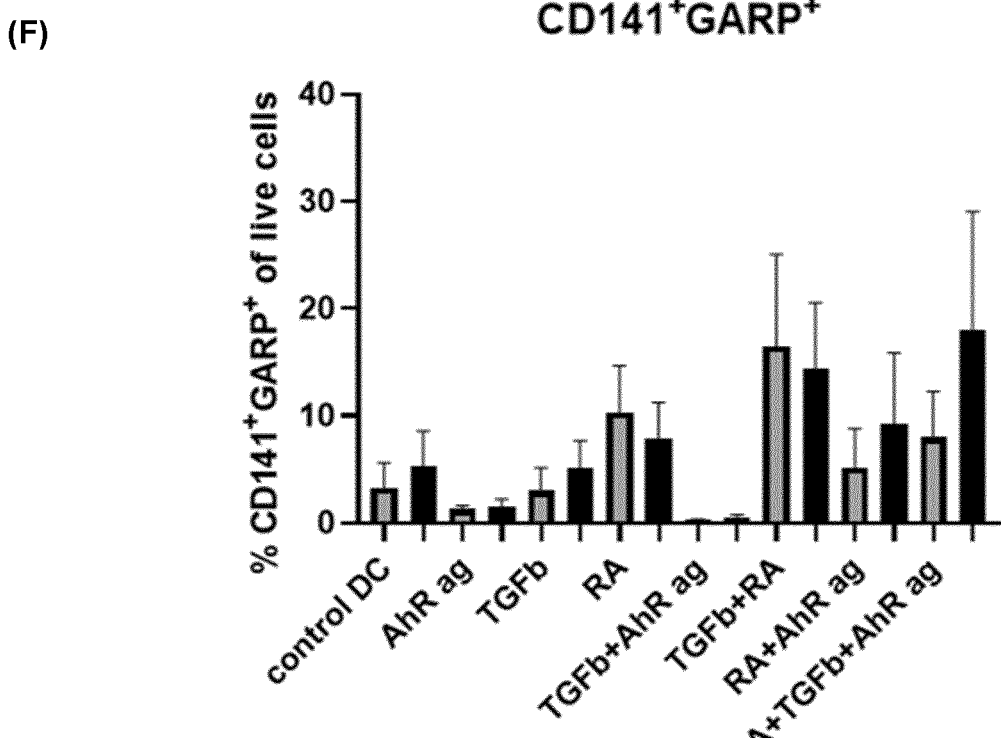
Figure 13:
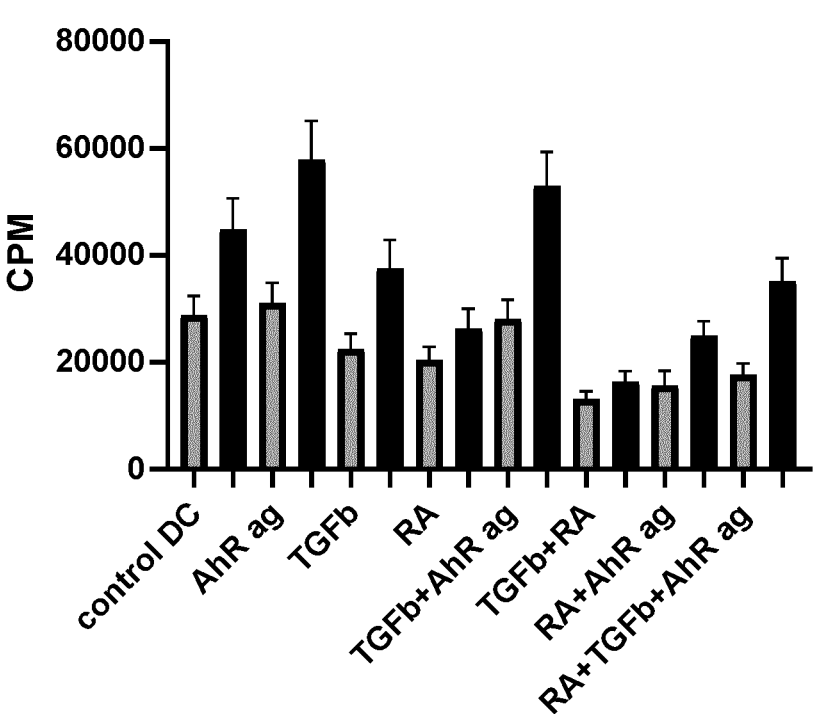
Figure 13:
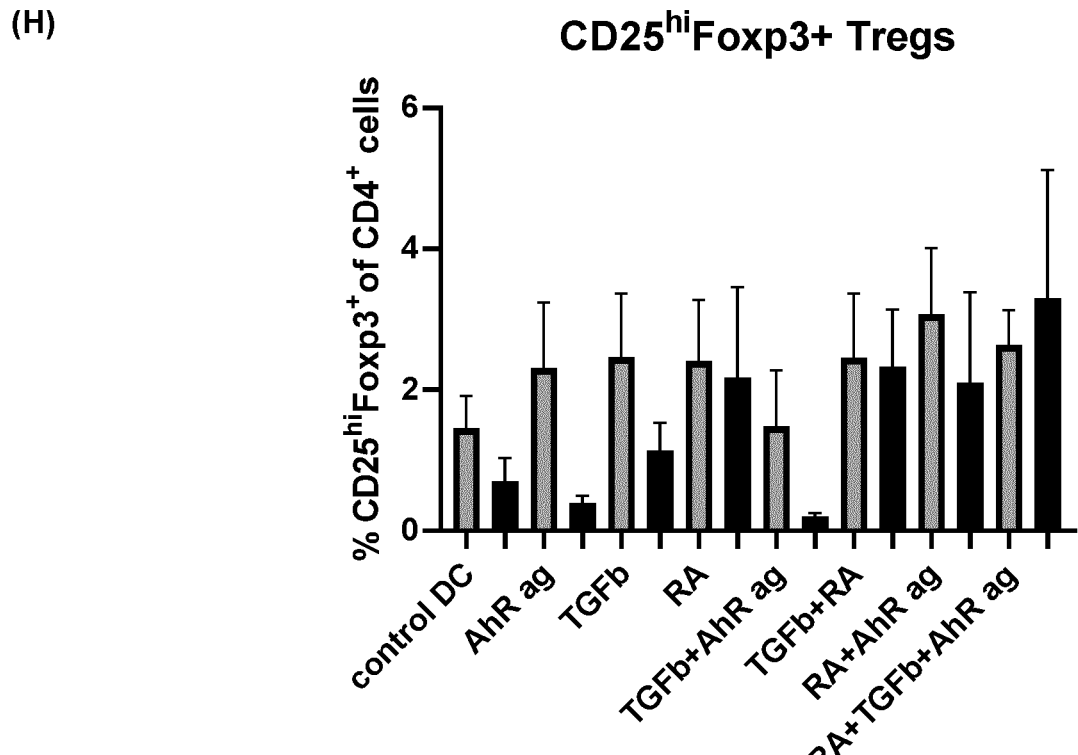

FIG. 13 shows the expression of the maturation marker CD83 (FIG. A), the activation marker CD86 (FIG. B), the tolerogenic marker ILT3 (FIG. C), the tolerogenic index, defined as the ILT3/CD86 expression (MFI) ratio (FIG. D), the expression of the marker CD103 (FIG. E), the frequencies of CD141 and GARP co-expressing cells (FIG. F), T cell proliferation (FIG. G) and production of CD4$^+$ CD25hiFoxp3$^+$ Treg cells (FIG. H) when DCs were cultured under various conditions. The DCs were unstimulated (grey bars) or stimulated (black bars) with LPS (see Example 13).

Figure 14:
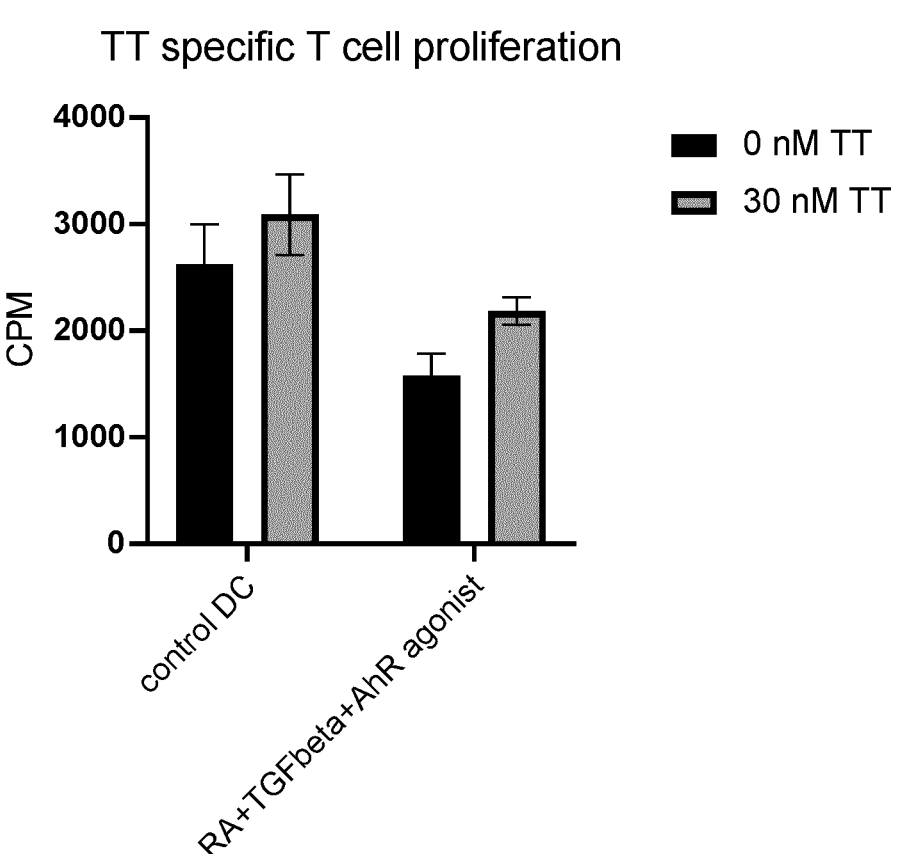

FIG. 14 shows T cell proliferation when DCs cultured in the presence of RA+TGFb+AhR agonist were loaded with tetanus toxoid and subsequently cultured in the presence of T cells. The DCs were unloaded (black bars) or loaded with TT (grey bars) (see Example 14).

Figure 15:
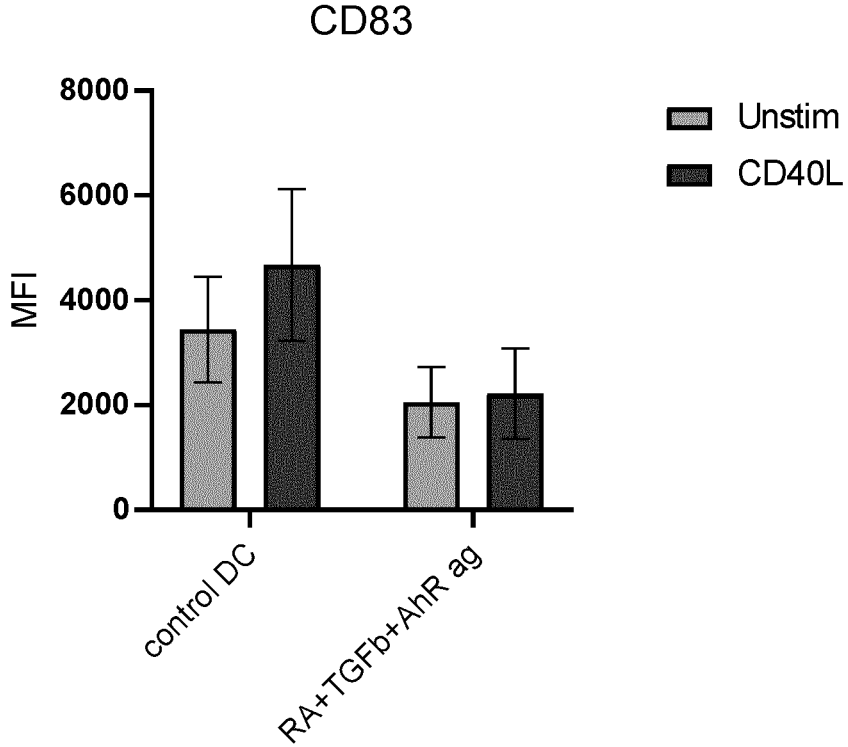
Figure 15:
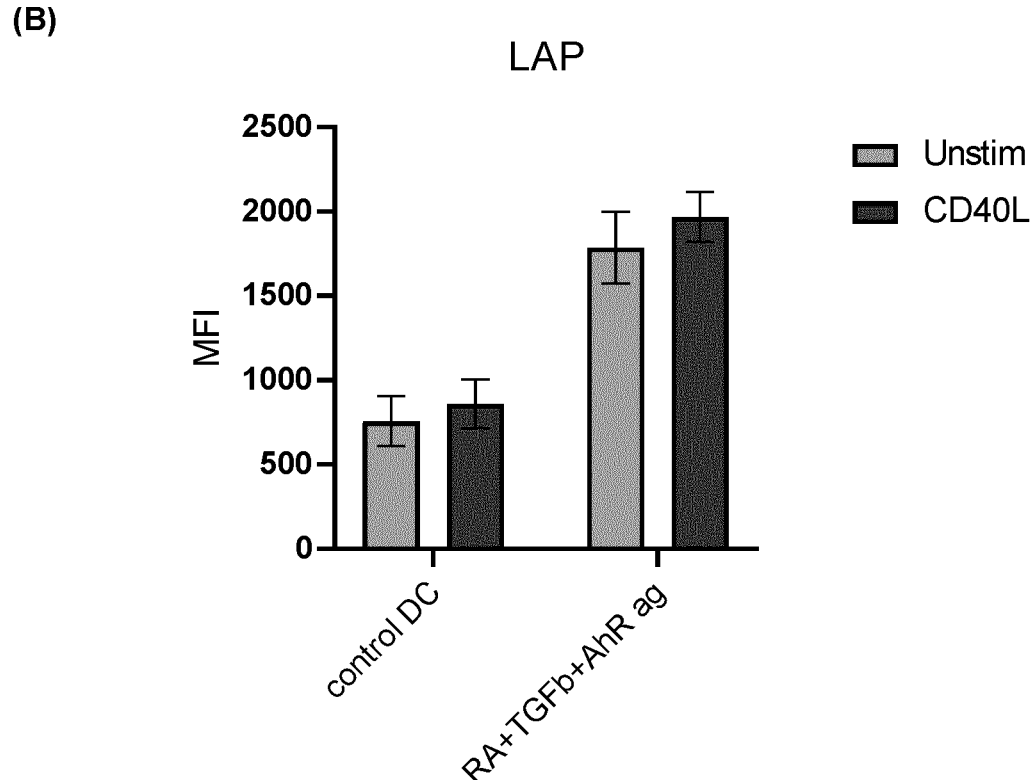
Figure 15:
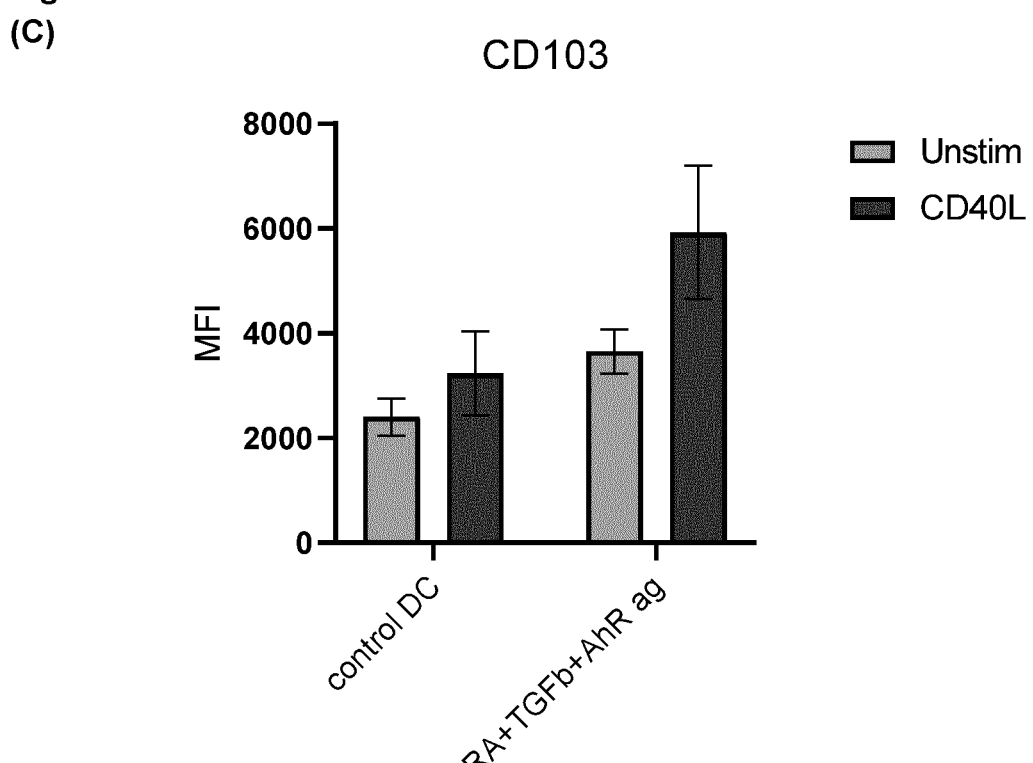
Figure 15:
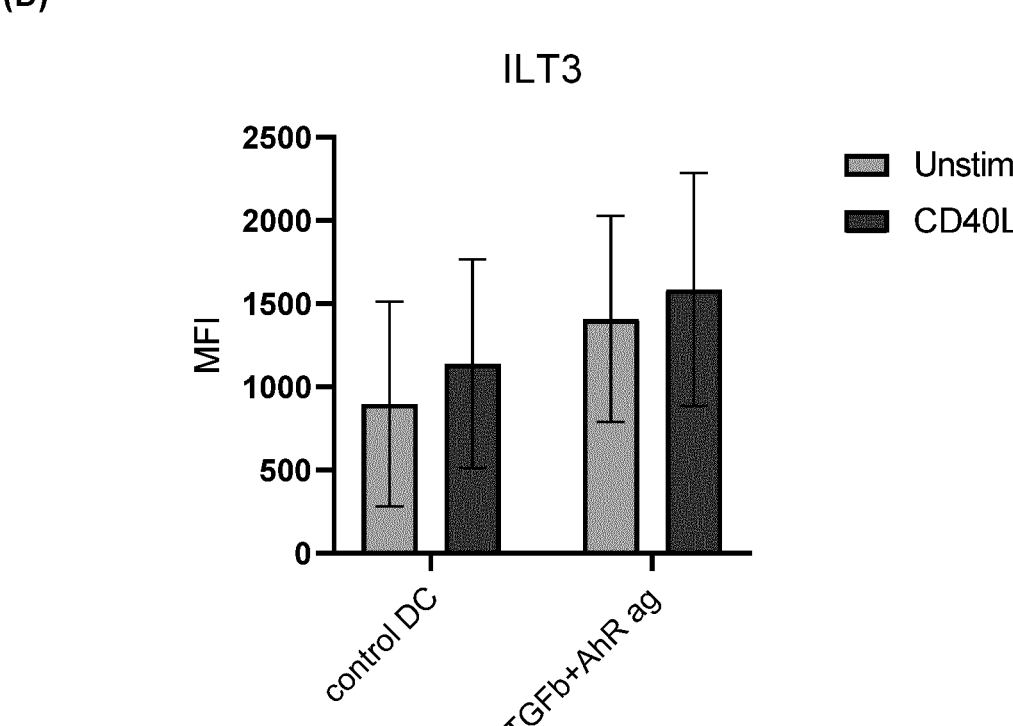
Figure 15:
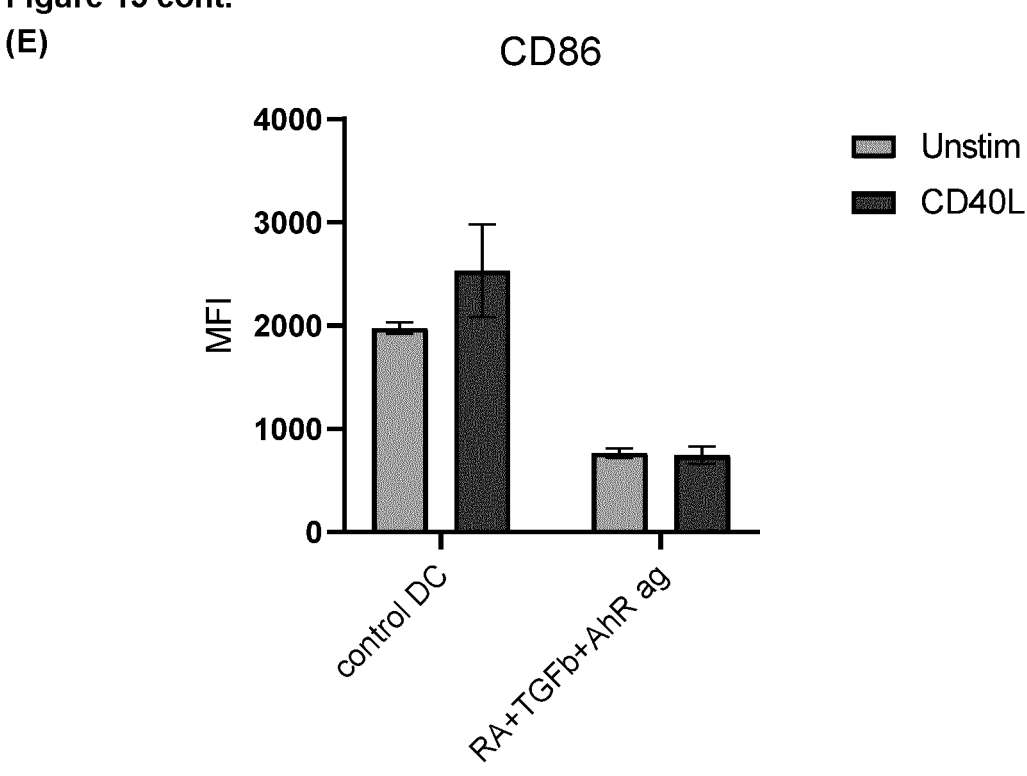
Figure 15:
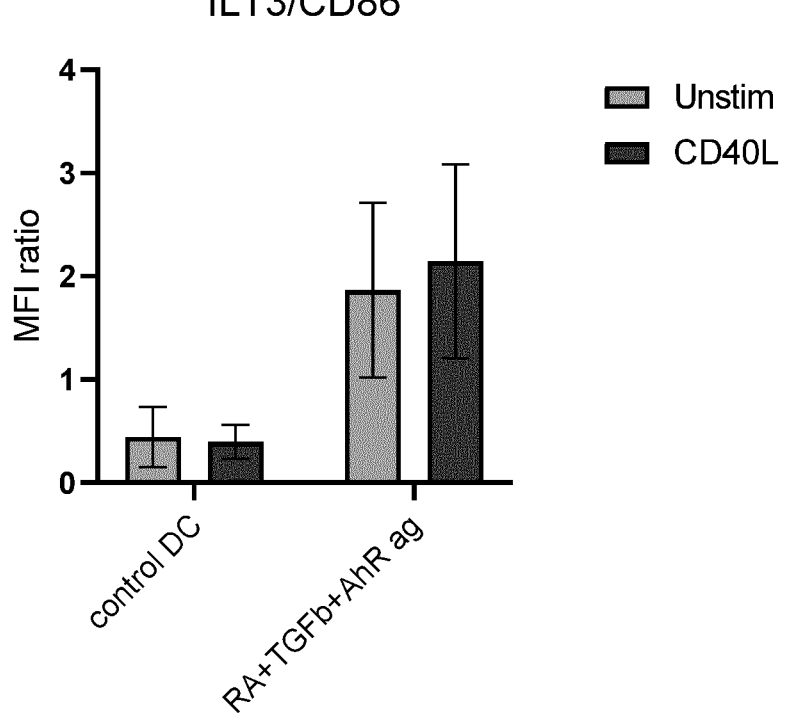
Figure 15:
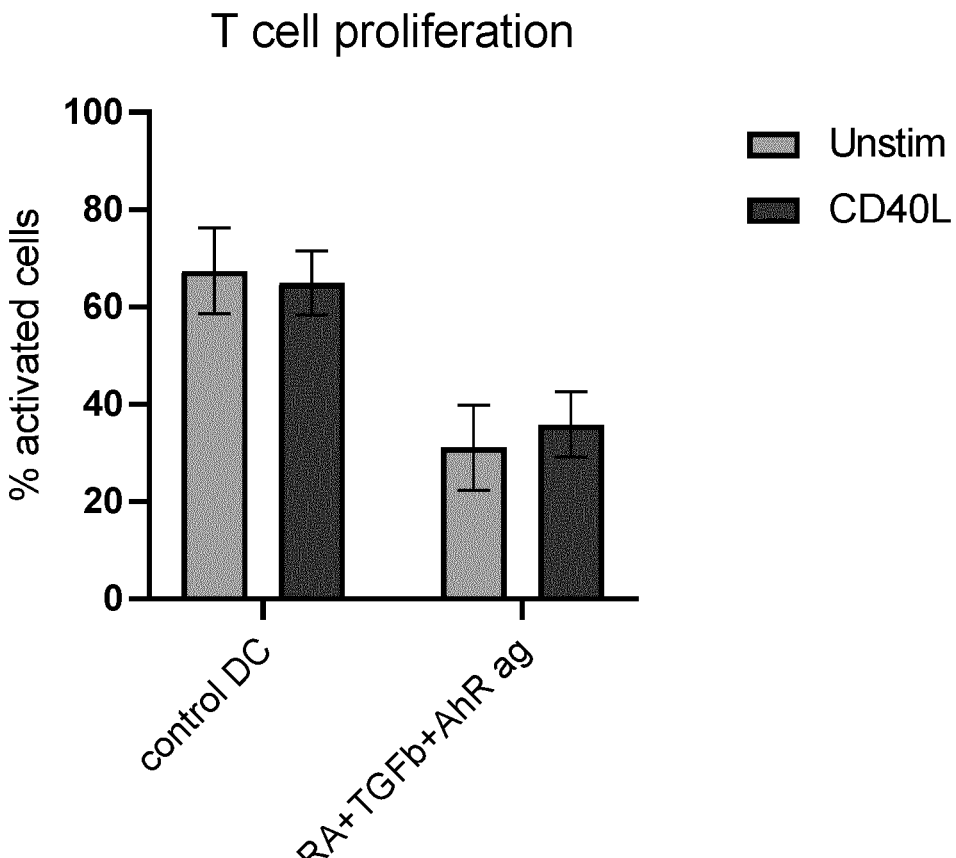

FIG. 15 shows the expression of the maturation marker CD83 (FIG. A), the expression level of the tolerogenic marker LAP (FIG. B), the expression of the marker CD103 (FIG. C), the tolerogenic marker ILT3 (FIG. D), the activation marker CD86 (FIG. E), the tolerogenic index, defined as the ILT3/CD86 expression (MFI) ratio (FIG. F) of DCs, cultured in the presence of RA+TGFb+AhR agonist and thereafter stimulated with CD40L (black bars) or unstimulated (grey bars). Induction of T cell proliferation with unstimulated and CD40L stimulated RA+TGFb+AhR agonist treated DCs is shown in (FIG. G) (see Example 15).

Figure 16:
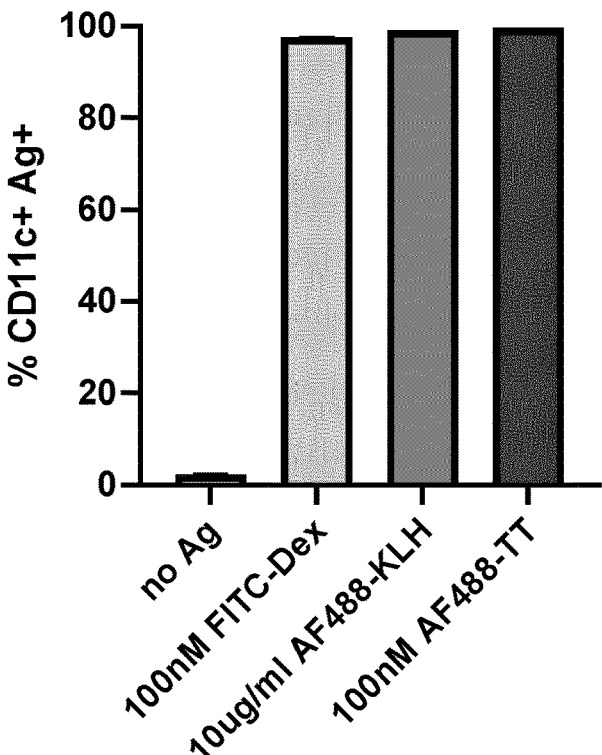
Figure 16:
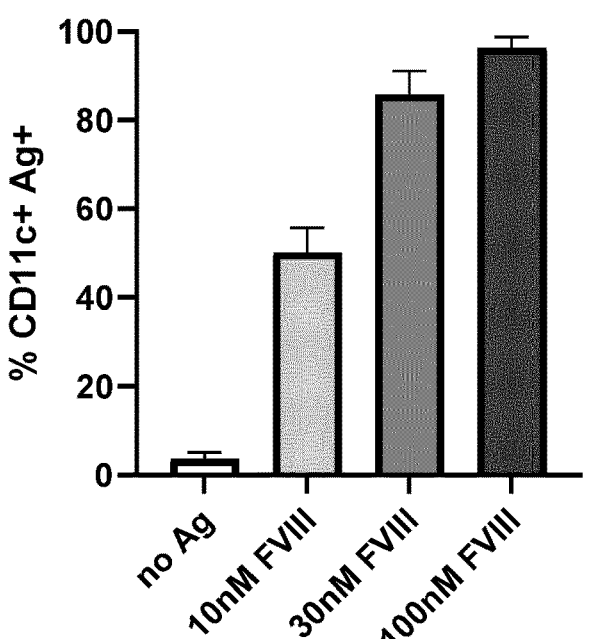
Figure 16:
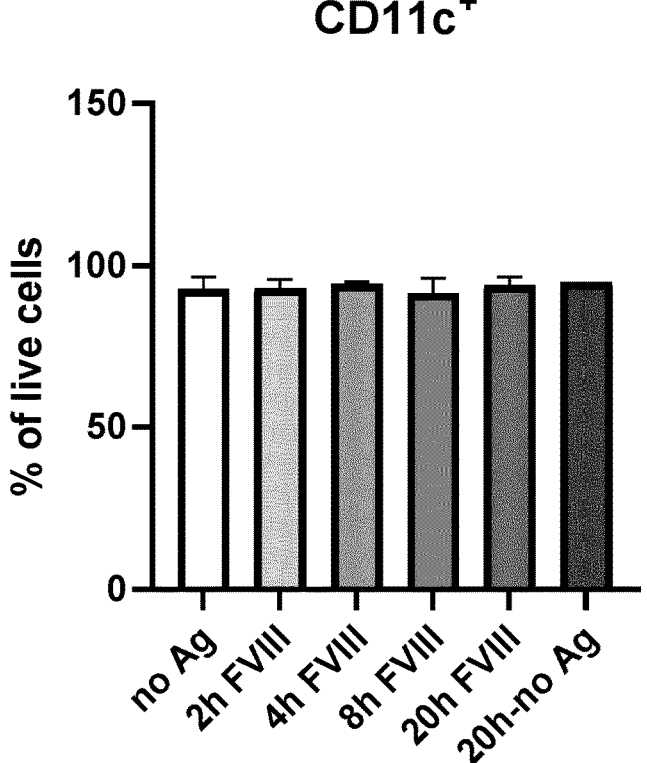
Figure 16:
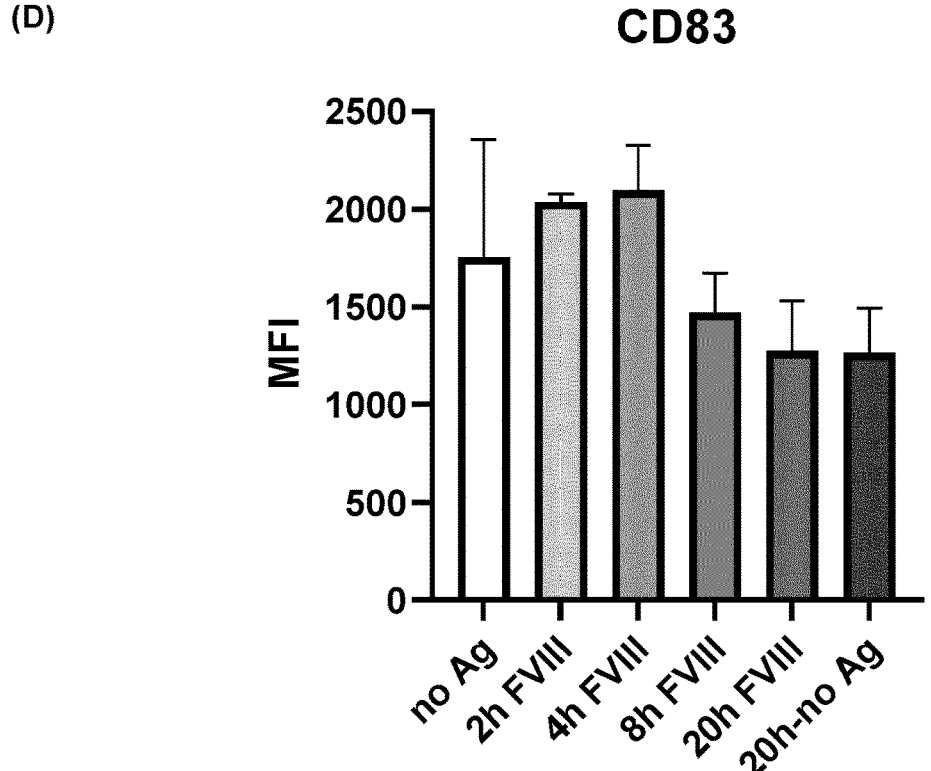
Figure 16:
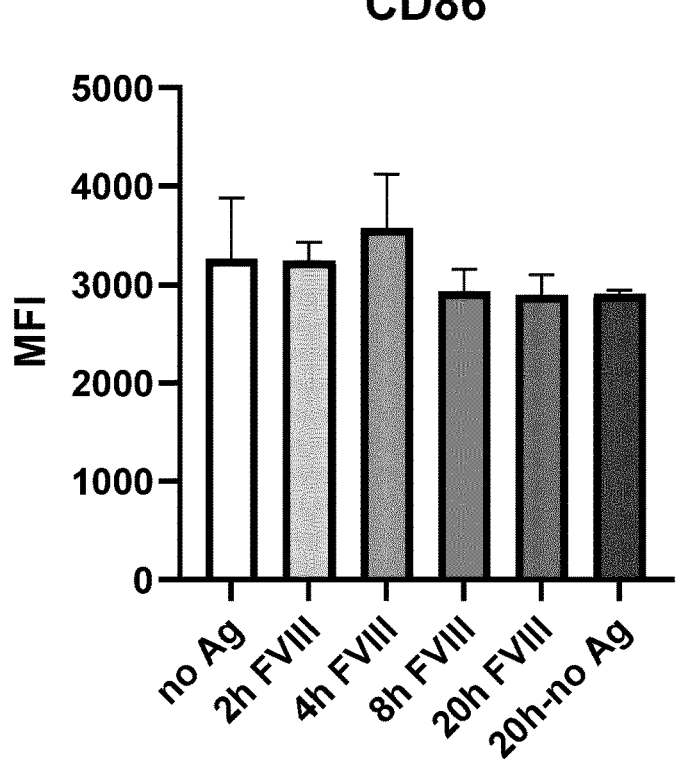
Figure 16:
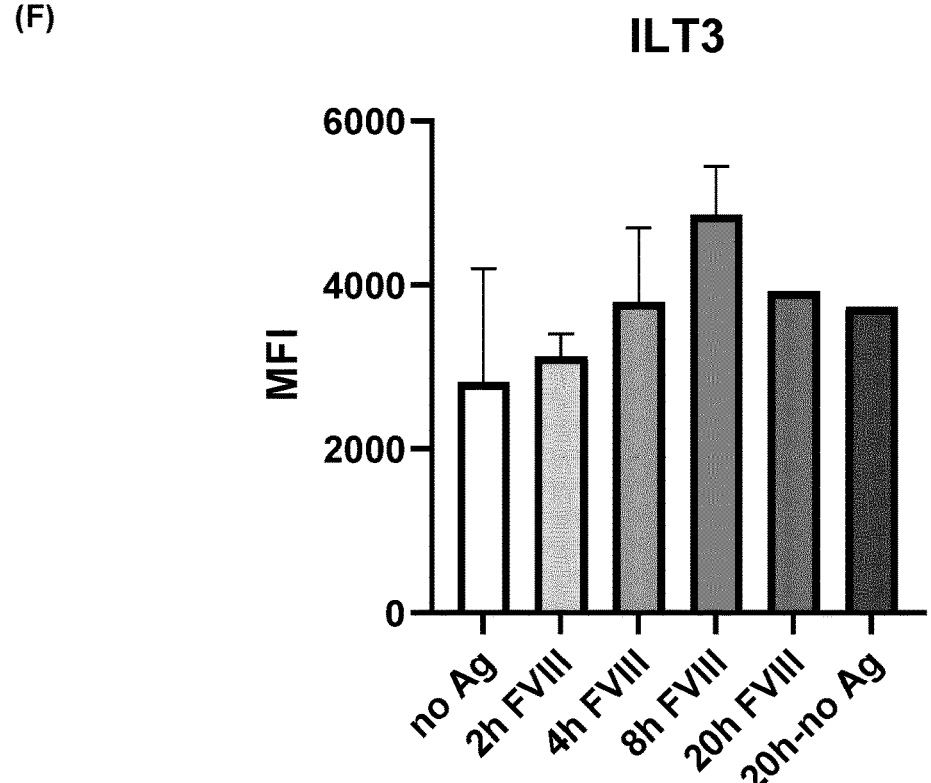
Figure 16:
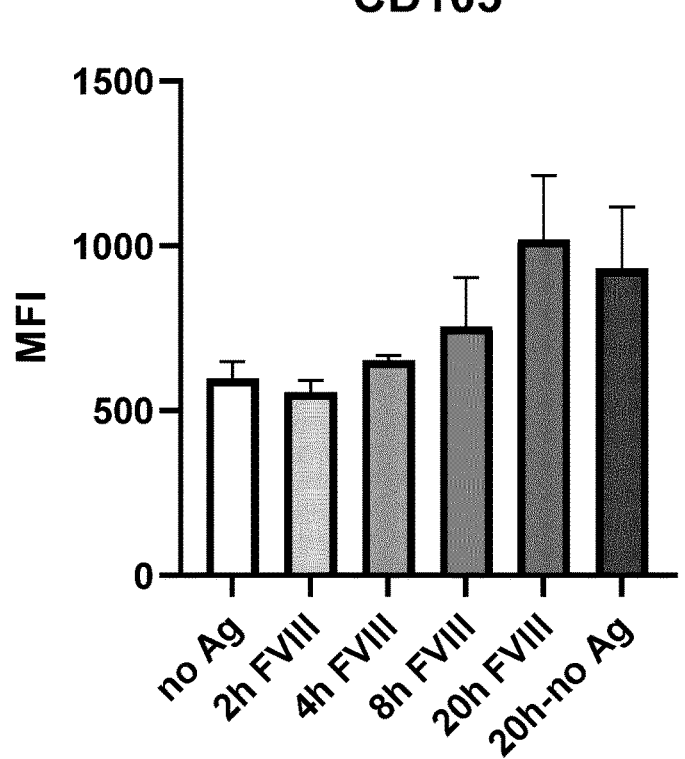
Figure 16:
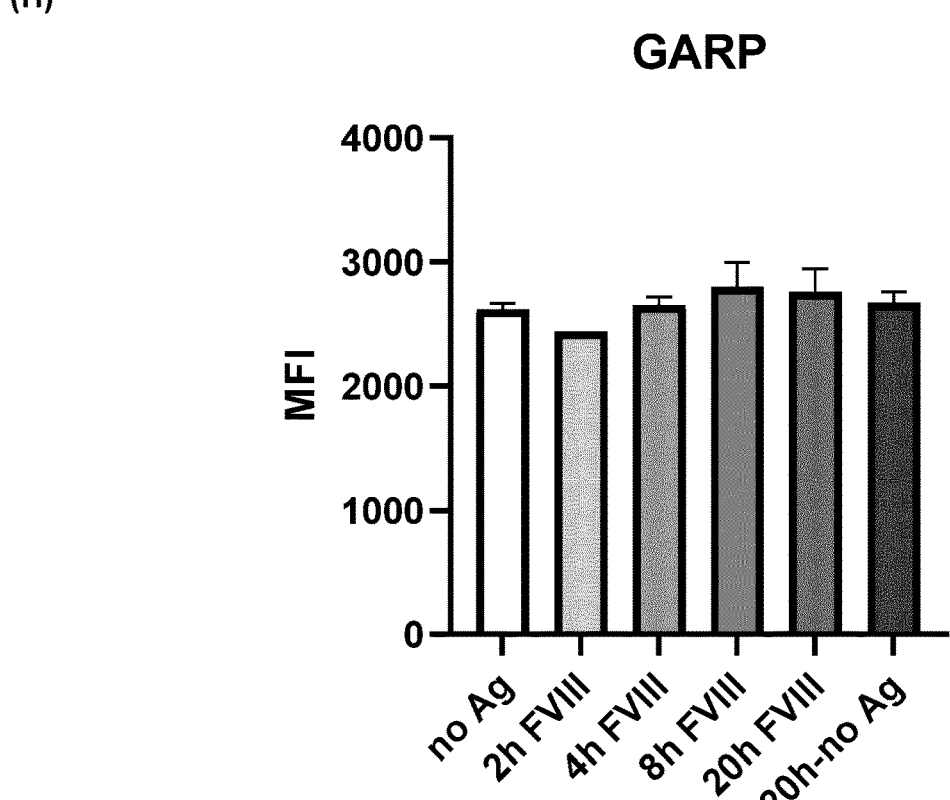
Figure 16:
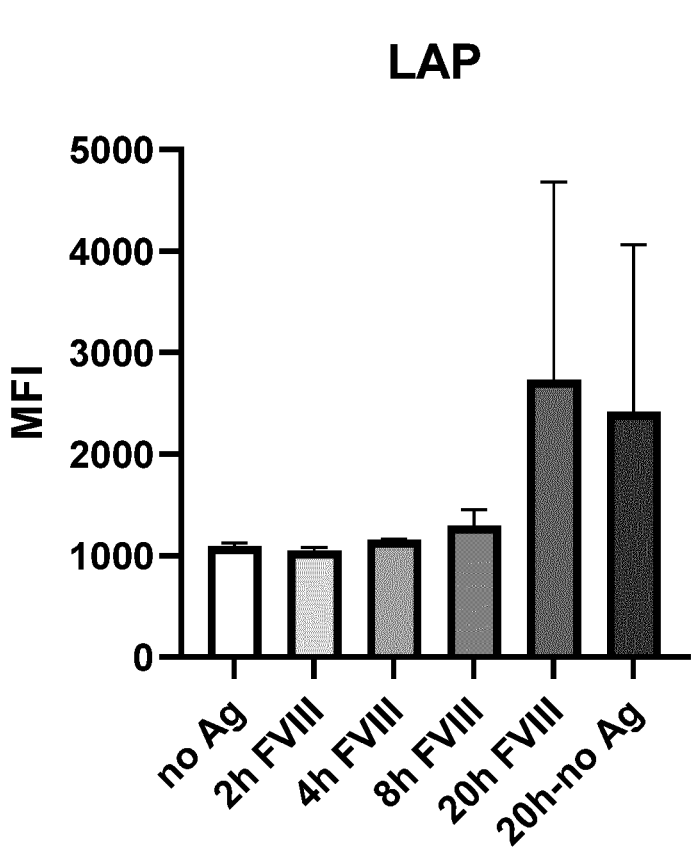

FIG. 16 shows antigen loading of DCs (FIGS. A-B), the expression of CD11c following antigen loading (FIG. C), the expression of the maturation marker CD83 following antigen loading (FIG. D), the activation marker CD86 following antigen loading (FIG. E), the tolerogenic marker ILT3 following antigen loading (FIG. F), the expression of the marker CD103 following antigen loading (FIG. G), the expression of the tolerogenic marker GARP following antigen loading (FIG. H) and the expression level of the tolerogenic marker LAP following antigen loading (FIG. 1) of DCs cultured in the presence of RA+TGFb+AhR agonist and antigen (see Example 16).

Figure 17:
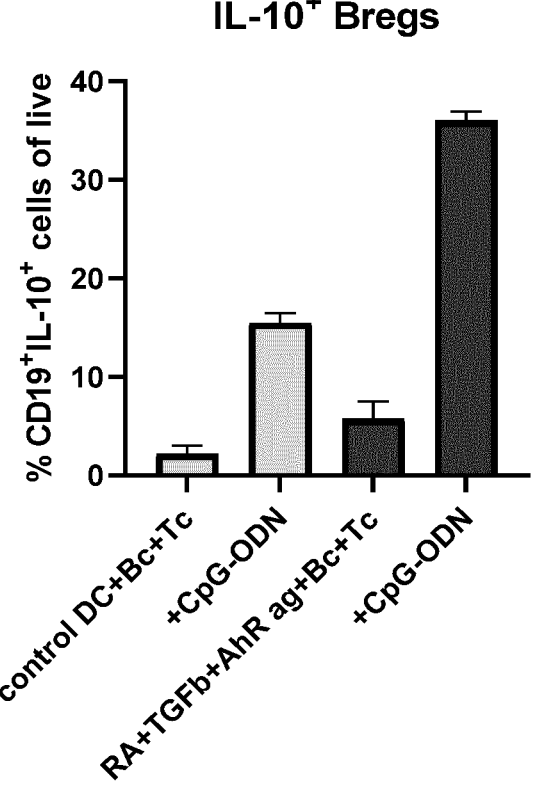
Figure 17:
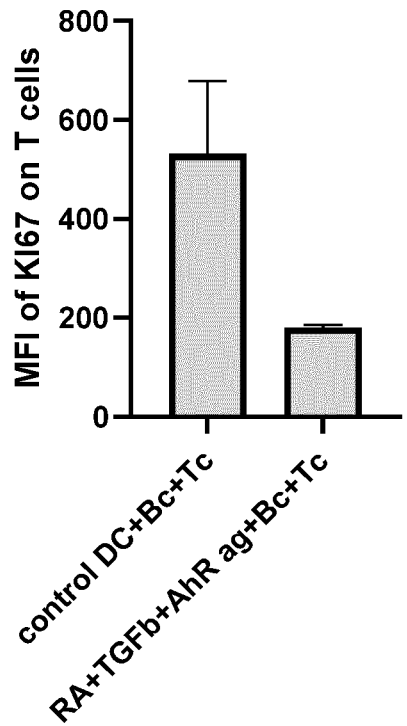
Figure 17:
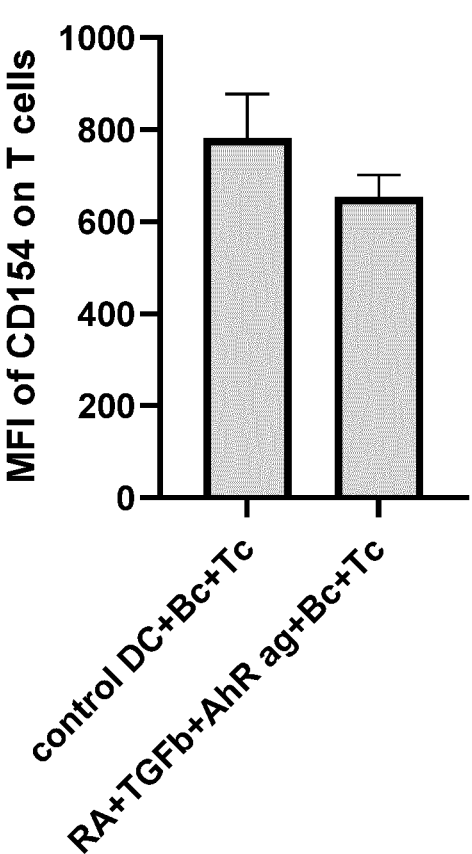

FIG. 17 shows B regulatory cell induction in a culture comprising RA+TGFbeta+AhR agonist treated DCs, B cells and T cells (FIG. A), the capacity of RA+TGFbeta+AhR agonist treated DCs, B cells and T cells to stimulate T cell proliferation (FIG. B) and the capacity of RA+TGFbeta+AhR agonist treated DCs, B cells and T cells to induce T cell activation (FIG. C).

Figure 18:
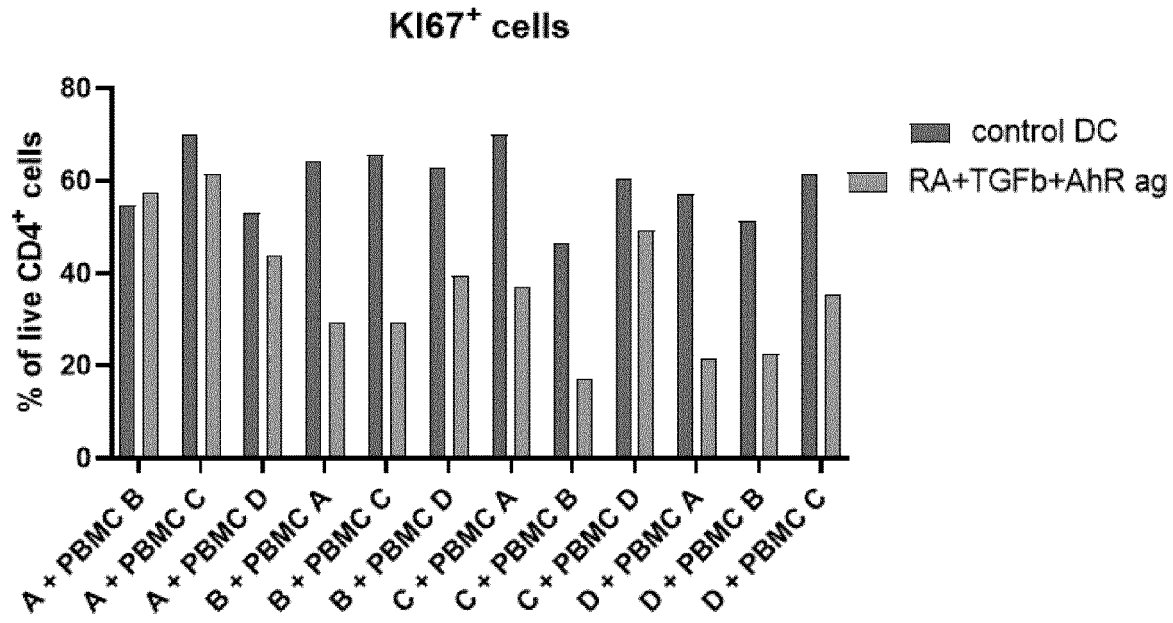
Figure 18:
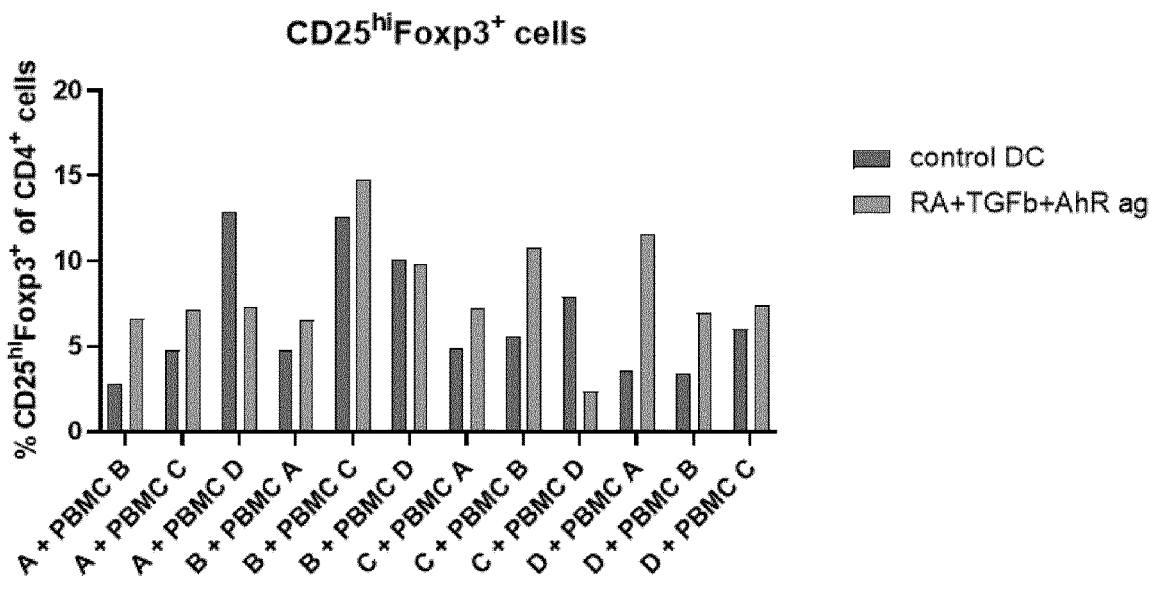

FIG. 18 shows the capacity of RA+TGFbeta+AhR agonist treated DCs to induce T cell proliferation when co-cultured with allogeneic PBMCS (FIG. A) and the capacity of RA+TGFbeta+AhR agonist treated DCs to induce Tregs in a mixed lymphocyte reaction (MLR) with allogeneic PBMCs (FIG. B).

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only and is not intended to be limiting. In addition, as used in this specification and the appended claims, the singular forms "a", "an", and "the" include plural referents unless the content clearly dictates otherwise. Thus, for example, reference to "an antigen" includes two or more such antigens, and the like.

Definitions

A "monocyte" is a large mononuclear phagocyte of the peripheral blood. Monocytes typically range in size from 10 to 30 um in diameter. The nucleus to cytoplasm ratio typically ranges from 2:1 to 1:1. The nucleus is often band shaped (horseshoe), or reniform (kidney-shaped). It may fold over on top of itself, thus showing brain-like convolutions. No nucleoli are visible. The chromatin pattern is fine and arranged in skein-like strands. The cytoplasm is abundant and appears blue gray with many fine azurophilic granules, giving a ground glass appearance in Giemsa staining. Vacuoles may be present. Often, the expression of specific surface markers is used to determine whether a cell is a monocyte. For instance, monocytes express CD14 (monocyte marker) and not CD1c (DC marker), CD56 (NK cell marker), CD19 (B cell marker), CD3 (T cell marker), CD16b (neutrophil marker) or CD66b (neutrophil marker).

An "antigen presenting cell" (APC) is part of a heterogeneous group of immune cells that mediate the cellular immune response by processing and presenting antigen for recognition by certain lymphocytes such as T cells. An APC displays antigen complexed with MHC on their surface. T cells may recognize these complexes using their T cell receptors (TCR). Classical APCs include DCs, macrophages, Langerhans cell and B cells.

A "dendritic cell" (DC) is an APC existing in vivo, in vitro, ex vivo or which can be derived from a hematopoietic stem cell, a hematopoietic progenitor or a monocyte. DCs and their precursors can be isolated from a variety of lymphoid organs, e.g., spleen, lymph nodes, as well as from bone marrow and peripheral blood. DCs have a characteristic morphology with thin sheets (lamellipodia) extending in multiple directions away from the DC body. DCs express constitutively both MHC class I and class II molecules, which present peptide antigens to CD8$^+$ and CD4$^+$ T cells, respectively. In addition, human skin and mucosal DCs also express the CD1 gene family, MHC class I-related molecules that present microbial lipid or glycolipid antigens. The DC membrane is also rich in molecules that allow adhesion of T cells (e.g. intercellular adhesion molecule 1 or CD54) or that co-stimulate T cell activation such as B7-1 and B7-2 (also known as CD80 and CD86 respectively).

"Tolerance" is the outcome of tolerogenic mechanisms of an immune response to a particular antigen, leading to prevention, silencing, downmodulation or downregulation of an adaptive immunological response to one or more antigens either directly or indirectly. A substance that is capable of inducing tolerance, i.e. a tolerogenic substance, is one that modulates APCs, e.g. DCs, to become tolerogenic and the resultant tolerogenic DCs are able to mediate tolerance induction.

"Tolerogenic" means an ability of a cell or a substance to induce tolerance mediated through mechanisms such as deletion, induction of unresponsiveness or anergy, and active suppression of an antigen specific T cell response through induction of Tregs. "Tolerised" refers to tolerance that has been induced in the adaptive immune system to an antigen meaning that tolerogenic mechanisms have been mediated to induce immunosuppressive actions.

"Immunogenic" means a cell or a substance capable of activating an adaptive immunological response to an antigen directly or indirectly.

"Tolerogenic APC" means an APC which, due to exposure to a tolerogenic stimulus, which can be of microbial origin, components of mammalian cells, a combination of cytokines, hormones, vitamins and other biological or pharmaceutical agents, has acquired the ability to induce tolerance. A tolerogenic APC has low ability to induce an immunogenic response, but high ability to induce active Tregs and other tolerance inducing responses.

"Tolerogenic DC" means a DC which, due to exposure to a tolerogenic stimulus, which can be of microbial origin, components of mammalian cells, a combination of cytokines, hormones, vitamins and other biological or pharmaceutical agents, has acquired the ability to induce tolerance. A tolerogenic DC has low ability to induce an immunogenic response, but high ability to induce active Tregs and other tolerance inducing responses.

"Autoimmune disease" means a pathological condition, in which the adaptive immune system is directed against self-antigens in a destructive manner.

"Self-antigen" (or "autoantigen") means any molecule or chemical group of a mammal (e.g. human) which acts as an antigen in the induction of an unwanted immune response in a disease state (e.g. antibody or effector T cell response), but to which the healthy immune system of the mammal is tolerant. The terms "self-antigen" and "autoantigen" are to be regarded as synonymous and are used interchangeably herein.

"Stimulated" means exposed to any artificial or natural compound that leads to cell signaling.

Method

The invention provides for a method of obtaining tolerogenic APCs that have the capability to tolerise the immune system to an antigen, comprising culturing isolated monocytes under specific culture conditions. Monocytes can be isolated from a number of sources. APCs are obtained according to the invention. The APCs that are obtained according to the invention include DCs and macrophages, preferably DCs. The DCs obtained by the method of the present invention may be myeloid DCs. The method is typically carried out under ex vivo or in vitro conditions, preferably ex vivo conditions. The monocytes that are isolated are typically present in a sample taken from a mammal. The mammal from which the sample is taken is typically a human (*Homo sapiens*). The sample is typically a blood sample, more preferably a sample of peripheral blood mononuclear cells (PBMCs) prepared from blood. The sample typically comprises mononuclear cells, preferably monocytic cells and in particular comprises monocytes. The method typically comprises isolating a population of monocytes from the sample, for example a PBMC sample. Preferably the isolated cells are $CD14^+$ monocytes. The method further comprises culturing the isolated monocytes cells in cell culture.

In one embodiment, the cell culture of the method of the invention comprises retinoic acid and TGFbeta. In another embodiment of the invention the cell culture of the method of the invention comprises retinoic acid, TGFbeta and an AhR agonist. In a further embodiment of the invention the cell culture of the method of the invention comprises retinoic acid and an AhR agonist. The cell culture preferably comprises retinoic acid and TGFbeta and even more preferably comprises retinoic acid, TGFbeta and an AhR agonist.

Retinoic acid is a metabolite of vitamin A1. The cell culture comprises retinoic acid. Retinoic acid may be present in the cell culture in any form, for example all-trans-retinoic acid, 13-cis-retinoic acid and/or 9-cis-retinoic acid, particularly all-trans-retinoic acid. Retinoic acid may be provided as a retinoic acid precursor for example retinol and/or a variant form of vitamin A, for example retinal, which generates retinoic acid in situ.

The AhR agonist used in the cell culture of the invention may be any AhR agonist, for example any of the AhR agonists disclosed in WO2012/050500, the contents of which are incorporated by reference in its entirety. The AhR agonist may be a full agonist or a partial agonist. The AhR agonist used in the method of the invention is preferably N-ethyl-N-phenyl-5-chloro-1,2-dihydro-4-hydroxy-1-methyl-2-oxo-quinoline-3-carboxamide (IMA-06201) (Mahiout et al. 2017), referred to in the present specification as "C1". The AhR agonist may alternatively be 6-formylindolo [3,2-b]carbazole (FICZ), 2-(1H-Indol-3-ylcarbonyl)-4-thiazolecarboxylic acid methyl ester (ITE), N-acetyl-N-phenyl-4-acetoxy-5-chloro-1,2-dihydro-1-methyl-2-oxo-quinoline-3-carboxamide ("C2"), N-(4-trifluoromethylphenyl)-1,2-dihydro-4-hydroxy-5-methoxy-1-methyl-2-oxo-quinoline-3-carboxamide ("C3") or N-acetyl-N-(4-trifluoromethylphenyl)-4-acetoxy-1,2-di-hydro-5-methoxy-1-methyl-2-oxo-quinoline-3-carboxam-ide ("C4"). Other potentially useful AhR agonists are described in Denison and Nagy, Ann. Rev. Pharmacol. Toxicol., 43:309-34, 2003 and references cited therein, all of which are incorporated by reference in their entirety.

TGFbeta used in the cell culture of the invention may be any TGFbeta isoform, for example TGFbeta1, TGFbeta2 or TGFbeta3, preferably TGFbeta1. Any TGFbeta isoform may be used alone or in combination with any other TGFbeta isoform.

The cell culture typically comprises GM-CSF and IL-4. Alternatively, the cell culture may comprise of GM-CSF alone, e.g. GM-CSF without IL-4, or M-CSF. The cell culture preferably comprises GM-CSF and IL-4. GM-CSF and IL-4 is added to the cell culture to induce differentiation of the isolated monocytes into APCs, preferably DCs. M-CSF is added to the cell culture to induce differentiation of isolated monocytes into APCs, preferably macrophages.

Typically, the GM-CSF and IL-4 or GM-CSF or M-CSF are added to the cell culture before or at the same time as any one of TGFbeta, AhR agonist and retinoic acid are added to the cell culture. Preferably, the GM-CSF and IL-4 are added to the cell culture before or at the same time as any one of TGFbeta, AhR agonist and retinoic acid are added to the cell culture. Typically, the AhR agonist is added to the cell culture in a first dose at the same time as GM-CSF or M-CSF and IL-4 are first added to the cell culture. Typically, the TGFbeta and a second dose of AhR agonist are added to the cell culture after the first dose of AhR agonist is added to the cell culture. Further typically, the retinoic acid is added to the cell culture after the TGFbeta and the second dose of AhR agonist are added to the cell culture. Typically, the GM-CSF or M-CSF and IL-4 are added to the cell culture in a second dose. Preferably, the second dose of GM-CSF or M-CSF and IL-4 is added to the cell culture at the same time as the TGFbeta and the second dose of AhR agonist are added to the cell culture.

The GM-CSF or M-CSF may be added to the cell culture before or at the same time as any one of TGFbeta, AhR agonist and retinoic acid are added to the cell culture and the IL-4 is added to the cell culture after a first dose of the AhR agonist is added to the cell culture. Typically, the TGFbeta and a second dose of AhR agonist are added to the cell culture after the first dose of AhR agonist is added to the cell culture. Further typically, the retinoic acid is added to the cell culture after the TGFbeta and the second dose of AhR agonist are added to the cell culture. The GM-CSF or M-CSF may be added to the cell culture in a second dose. Preferably, the second dose of GM-CSF or M-CSF is added to the cell culture at the same time as the TGFbeta and the second dose of AhR agonist are added to the cell culture.

The cell culture may further comprise the antigen or an epitope containing fragment of the antigen. The antigen or epitope containing fragment thereof may be associated with or expressed on the isolated monocytes in culture. The antigen or epitope containing fragment thereof may be expressed on the cell surface of the monocytes or APCs. The antigen or epitope containing fragment thereof may be intracellular. The antigen or epitope containing fragment thereof may be an antigen or epitope containing fragment that is not native to the monocytes, e.g. the monocytes may have taken up an antigen or epitope containing fragment thereof from other cells prior to being isolated. The monocytes or APCs may be transfected with antigen-encoding mRNA to express an antigen or epitope containing fragment thereof. Methods to transfect cells with antigen-encoding mRNA are known in the art.

In the case of methods to induce tolerance to an allograft, the antigen or epitope containing fragment thereof may be associated with or expressed on monocytes isolated from a sample taken from a graft donor or may be expressed by the APC during or after culture using the method of the invention. The isolated monocytes from a sample taken from a donor cultured, using the method of the invention, allows for tolerogenic APCs to be produced. Such tolerogenic APCs may be administered to a recipient to prevent immune rejection of an allograft transplant from the donor.

In the case of the isolated monocytes from a sample taken from a recipient, the monocytes may be cultured using the method of the invention allowing for tolerogenic APCs to be produced. The tolerogenic APCs may be loaded with donor antigens such that they present donor-derived antigens. Alternatively, the tolerogenic APCs may not be loaded with donor antigens ex vivo. Such tolerogenic APCs presenting (or not) donor-derived antigens may be administered back to a recipient to prevent immune rejection of an allograft transplant from the donor.

Alternatively, the antigen or epitope containing fragment thereof is a component that is added to the cell culture. Thus, the cell culture further comprises an antigen or epitope containing fragment thereof. Preferably, the antigen or epitope containing fragment is added to the cell culture before, at the same time as or after the retinoic acid is added to the cell culture. The antigen or epitope containing fragment thereof may be added as part of a mixture of antigens, for example, cells, a tissue or sample containing one or more antigens may be added to the culture.

The antigen or epitope containing fragment may be single antigen or epitope containing fragment thereof (e.g. in purified form), or a pool or antigens and/or epitope containing fragments thereof. The antigen or epitope containing fragment may be a cell, blood, tissue sample or extract thereof. In the case of methods to induce tolerance to an allograft, the antigen or epitope containing fragment thereof may be a sample of the graft, or may be derived from a sample of the graft or other donor-derived tissue, cell or blood and said antigen or epitope containing fragment thereof may be added directly to the cell culture.

The antigen or epitope containing fragment thereof optionally may not be added directly to the cell culture. Instead, the antigen or epitope containing fragment thereof may be present in vivo. Thus, the tolerogenic APCs optionally may not be loaded with an antigen or epitope containing fragment thereof ex vivo, but instead have the capability to be loaded with an antigen or epitope containing fragment thereof in vivo when the tolerogenic APCs are administered. The tolerogenic APCs therefore recognize and process an antigen or epitope containing fragment thereof in vivo.

The antigen or epitope containing fragment thereof may be or be derived from a biological drug. Thus, the biological drug may be used as the antigen in whole or in part (i.e. an epitope containing part).

The antigen or epitope containing fragment thereof may be or be derived from a self-antigen.

Generation of Regulatory T Cells

The method of the present invention may further comprise culturing ex vivo the obtained tolerogenic APCs with T cells thereby inducing the generation of Tregs. Thus, the tolerogenic APCs of the invention when cultured ex vivo with T cells induce Tregs. The induced Tregs may be any Tregs, for example $CD4^+CD25^+Foxp3^+$ Tregs and/or Type 1 regulatory T (Tr1) $CD4^+CD49b^+LAG3^+$ cells, preferably $CD4^+CD25^+Foxp3^+$ Tregs. A Treg or population thereof may be obtainable or obtained by the method of the present invention.

A Treg or population thereof may be used in a method of treating a mammalian subject or a method of treatment of a mammalian subject with or at risk of an immune reaction to an antigen.

As shown in FIGS. 5 (A) and 5 (B), tolerogenic DCs of the invention, when unstimulated or stimulated e.g. with an immunogenic stimulus such as LPS or a pro-inflammatory cytokine cocktail, show a low T cell proliferation induction capacity. The combination of retinoic acid, TGFbeta and an AhR agonist was superior to the combinations of retinoic acid and TGFbeta and retinoic acid and a AhR agonist in reducing T cell proliferation induction capacity.

Thus, suitably tolerogenic APCs of the present invention (e.g. DCs of the invention) when unstimulated have a T cell proliferation induction capacity which is no more than 100% e.g. no more than 90%, e.g. no more than 80%, e.g. no more than 70% of that of control cells when unstimulated. Further, suitably tolerogenic APCs of the present invention (e.g. DCs of the invention) when stimulated, e.g. with an immunogenic stimulus such as LPS or a pro-inflammatory cytokine cocktail, have a T cell proliferation induction capacity which is no more than 70% e.g. no more than 60% e.g. no more than 50% of that of control cells when stimulated e.g. with an immunogenic stimulus such as LPS. Control cells are the same type of APCs from the same subject which have not been exposed to the tolerogenic compounds.

As shown in FIGS. 10 (A) and 10 (B), tolerogenic DCs of the invention have a high Treg induction capacity. The combination of retinoic acid, TGFbeta and an AhR agonist was superior to the combinations of retinoic acid and TGFbeta or retinoic acid and AhR agonist in inducing Tregs.

Thus, suitably the tolerogenic APCs of the present invention (e.g. DCs of the invention) when unstimulated have a Treg induction capacity which is at least 130%, e.g. at least 150%, e.g. at least 175%, e.g. at least 200% of that of control cells when unstimulated. Further, suitably tolerogenic APCs of the present invention (e.g. DCs of the invention) when stimulated, e.g. with an immunogenic stimulus such as LPS, suitably have a Treg induction capacity which is at least 130% e.g. at least 150% e.g. at least 200% of that of control cells when stimulated e.g. with an immunogenic stimulus such as LPS. Control cells are the same type of APCs from the same subject which have not been exposed to the tolerogenic compounds.

As shown in FIG. 11 (J), tolerogenic DCs of the invention have a high Treg induction capacity when CD14+ monocytes are isolated from the blood of a patient with haemophilia.

Thus, suitably the tolerogenic APCs of the present invention (e.g. DCs of the invention when unstimulated have a Treg induction capacity which is at least 130%, e.g. at least 150%, e.g. at least 175%, e.g. at least 200% of that of control cells when unstimulated. Further, suitably tolerogenic APCs of the present invention (e.g. DCs of the invention) when stimulated, e.g. with an immunogenic stimulus such as LPS, suitably have a Treg induction capacity which is at least 130% e.g. at least 150% e.g. at least 200% of that of control cells when stimulated e.g. with an immunogenic stimulus such as LPS. Control cells are the same type of APCs from the same subject which have not been exposed to the tolerogenic compounds.

Tolerogenic Antigen Presenting Cells

Monocytes are differentiated into DCs. During differentiation, a proportion of the DCs may be polarised towards a tolerogenic phenotype. The method of the invention typically allows for the generation of tolerogenic APCs, for example, tolerogenic DCs, that have tolerogenic cell surface marker expression.

CD83 is an integral membrane protein and is an activation/maturation marker. Typically, unstimulated APCs, particularly DCs, show a level of expression of CD83 which does not differ greatly between tolerogenic cells and non-tolerogenic cells. However, when stimulated, e.g. with an immunogenic stimulus such as LPS, APCs, particularly DCs, may show an increased level of expression of CD83. Thus, the level of CD83 expression is typically increased to a higher degree in stimulated non-tolerogenic cells than in stimulated tolerogenic cells. Desirable tolerogenic APC, particularly DCs, have a low level of expression of CD83 even when stimulated. Desirable tolerogenic APCs, particularly DCs, are as resistant as possible to stimulation by immunogenic stimulus e.g. LPS with respect to upregulation of CD83 expression.

The tolerogenic APCs of the present invention (e.g. DCs of the invention) in at least some embodiments have the merit of having low expression of CD83 when stimulated, e.g. with an immunogenic stimulus such as LPS, compared to correspondingly stimulated control cells. Control cells are the same type of APCs from the same subject which have not been exposed to the tolerogenic compounds.

Suitably, the tolerogenic APCs of the present invention (e.g. DCs of the invention) when unstimulated have a level of expression of CD83 which is no more than 100%, e.g. no more than 90%, e.g. no more than 80%, e.g. no more than 70%, e.g. no more than 60%, e.g. no more than 50% of that of control cells when unstimulated.

Figure 1:
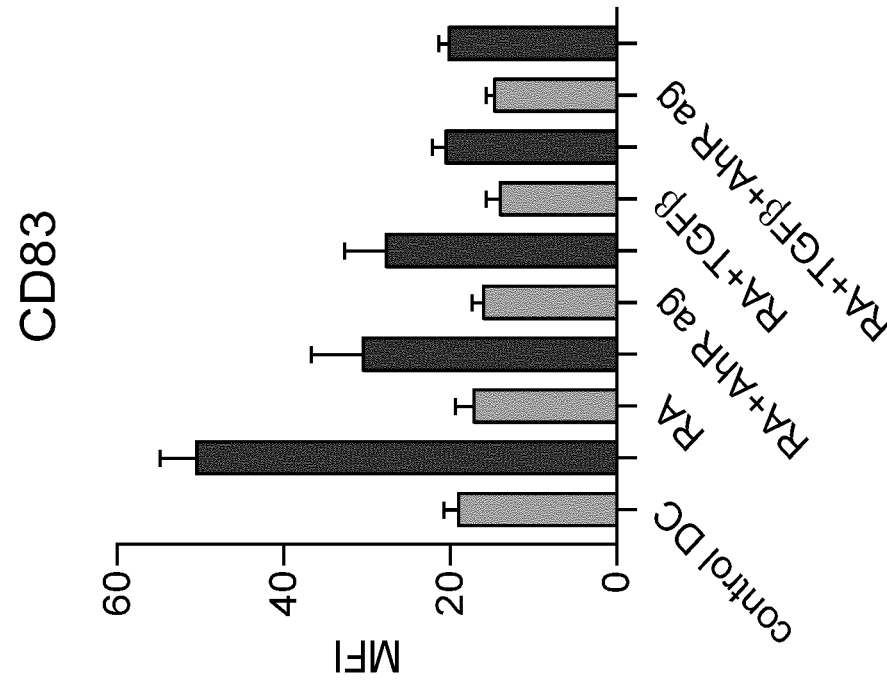
FIG. 1 shows the expression of the maturation marker CD83 on DCs cultured under various conditions (FIGS. (A) and (B)). The DCs were unstimulated (grey bars) or stimulated (black bars) with lipopolysaccharide (LPS) (see Example 1).
Figure 1:
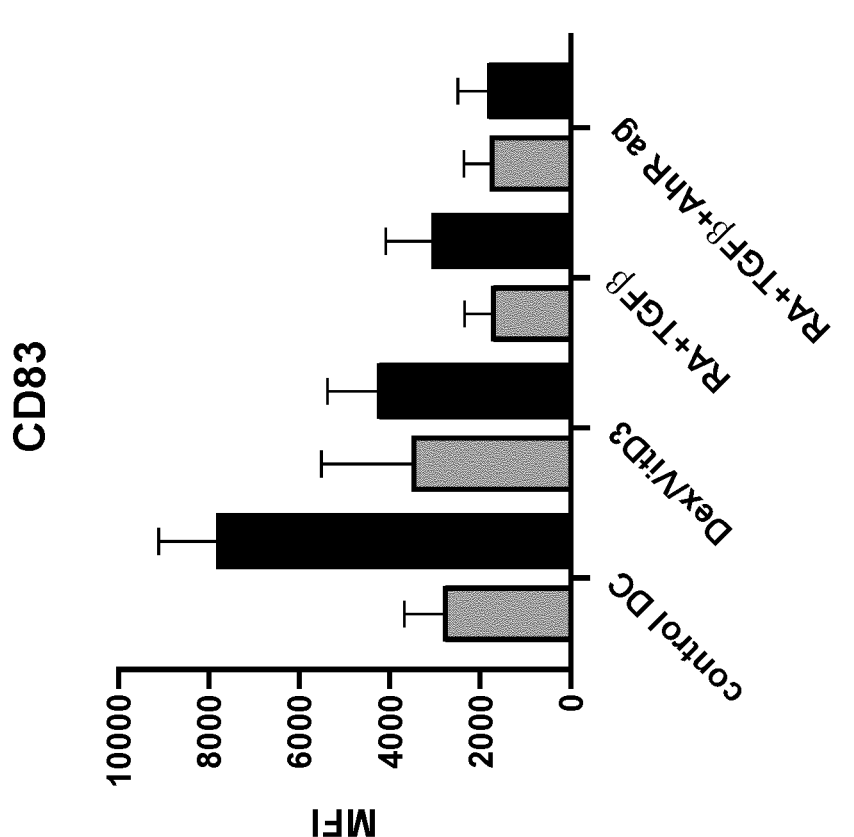

Suitably, the tolerogenic APCs of the present invention (e.g. DCs of the invention) when stimulated, e.g. with an immunogenic stimulus such as LPS, have a level of expression of CD83 which is no more than 70% e.g. no more than 60% e.g. no more than 50% of that of control cells when stimulated e.g. with an immunogenic stimulus such as LPS. As described in more detail in the Examples section and as shown in FIG. 1, the greatest reduction in the level of expression of CD83 in stimulated APCs as compared with corresponding control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta which was superior to use of retinoic acid and an AhR agonist.

The tolerogenic APCs of the present invention (e.g. DCs of the invention) in at least some embodiments also have the merit of having a level of expression of CD83 which is resistant to further upregulation upon stimulation.

Suitably, tolerogenic APCs of the present invention (e.g. DCs of the invention) when stimulated, e.g. with an immunogenic stimulus such as LPS, have a level of expression of CD83 which is no more than 200% e.g. no more than 175% e.g. no more than 150% e.g. no more than 125% of that of corresponding cells when not stimulated. As described in more detail in the Examples section and as shown in FIG. 1, the greatest reduction in the level of expression of CD83 in stimulated APCs as compared with corresponding unstimulated cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta which was superior to use of retinoic acid and an AhR agonist.

CD86 is an integral membrane protein and is an activation/maturation marker and a co-stimulatory molecule. Typically, unstimulated APCs, particularly DCs, show a level of expression of CD86 which does not differ greatly between tolerogenic cells and non-tolerogenic cells. However, when stimulated, e.g. with an immunogenic stimulus such as LPS, APCs, particularly DCs, may show an increased level of expression of CD86. The level of CD86 expression is typically increased to a higher degree in non-tolerogenic cells than in tolerogenic cells. Desirable tolerogenic APCs, particularly DCs, have a low level of expression of CD86 when stimulated. Desirable tolerogenic APCs, particularly DCs, are as resistant as possible to stimulation by immunogenic stimulus e.g. LPS with respect to upregulation of CD86 expression.

The tolerogenic APCs of the present invention (e.g. DCs of the invention) in at least some embodiments have the merit of having low expression of CD86 when stimulated, e.g. with an immunogenic stimulus such as LPS, compared to control cells when stimulated. Control cells are the same type of APC from the same subject which have not been exposed to the tolerogenic compounds.

Suitably the tolerogenic APCs of the present invention (e.g. DCs of the invention) when unstimulated have a level of expression of CD86 which is no more than 100%, e.g. no more than 90%, e.g. no more than 80%, e.g. no more than 70% e.g. no more than 60%, e.g. no more than 50% of that of control cells when unstimulated.

Suitably, the tolerogenic APCs of the present invention (e.g. DCs of the invention) when stimulated, e.g. with an immunogenic stimulus such as LPS, have a level of expression of CD86 which is no more than 80% e.g. no more than 70% e.g. no more than 60% e.g. no more than 50% of that of control cells when stimulated e.g. with an immunogenic stimulus such as LPS. As described in more detail in the Examples section and as shown in FIG. 2, the greatest reduction in the level of expression of CD86 in stimulated APCs as compared with corresponding control cells when stimulated was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta which was superior to use of retinoic acid and an AhR agonist.

The tolerogenic state of DCs is characterized by a low co-stimulatory potential and in addition high expression of inhibitory molecules. ILT3 is an inhibitory cell surface receptor which can be expressed by tolerogenic APCs, preferably DCs. DCs overexpressing ILT3 display lower phosphorylation levels of NF-kappaB and fail to stimulate the full program of Th proliferation and maturation eliciting instead the differentiation of Treg cells (Vlad et al 2009). ILT3 expression and upregulation is typically not dependent on an immunogenic stimulus such as LPS. Typically, non-tolerogenic and tolerogenic APCs, particularly DCs, show a level of expression of ILT3 which does not differ greatly between unstimulated and stimulated (e.g. with an immunogenic stimulus such as LPS) conditions. The level of ILT3 expression is typically much higher in in tolerogenic cells than in non-tolerogenic cells. Desirable tolerogenic APCs, particularly DCs, have a high level of expression of ILT3 which is not downregulated upon stimulation by immunogenic stimulus e.g. LPS.

The tolerogenic APCs of the present invention (e.g. DCs of the invention) in at least some embodiments have the merit of having high expression of ILT3 when unstimulated or stimulated, e.g. with an immunogenic stimulus such as LPS, compared to control cells when unstimulated or stimulated, respectively. Control cells are the same type of antigen presenting cell from the same subject which have not been exposed to the tolerogenic compounds.

Suitably, the tolerogenic APCs of the present invention (e.g. DCs of the invention) when unstimulated and stimulated, e.g. with an immunogenic stimulus such as LPS, have a level of expression of ILT3 which is at least 150% e.g. at least 175% e.g. at least 200% e.g. at least 250% e.g. at least 300% of that of control cells when unstimulated and stimulated e.g. with an immunogenic stimulus such as LPS, respectively. As described in more detail in the Examples section and as shown in FIG. 3, the greatest increase in the level of expression of ILT3 in unstimulated and stimulated APCs as compared with control cells was obtained when the APCs of the present invention were produced by the method of the invention when the tolerogenic inducing compounds used were retinoic acid, TGFbeta and an AhR agonist. Use of the combination of retinoic acid, TGFbeta and an AhR agonist was superior to use of retinoic acid and TGFbeta which was superior to use of retinoic acid and an AhR agonist.

The tolerogenic capacity of APCs, particularly DCs may be determined by the ratio between ILT3 and CD86 expression levels. The ILT3/CD86 ratio is typically much higher in tolerogenic cells than in non-tolerogenic cells. Desirable tolerogenic APCs, particularly DCs, have a high ILT3/CD86 ratio regardless of being unstimulated or stimulated by immunogenic stimulus e.g. LPS.

The tolerogenic APCs of the present invention (e.g. DCs of the invention) in at least some embodiments have the merit of having a high ILT3/CD86 ratio when unstimulated or stimulated, e.g. with an immunogenic stimulus such as LPS, compared to control cells when unstimulated or stimulated, e.g. with an immunogenic stimulus such as LPS, respectively. Control cells are the same type of APCs from the same subject which have not been exposed to the tolerogenic compounds.

Suitably, the APCs of the present invention (e.g. DCs of the invention) when unstimulated, have an ILT3/CD86 ratio which is at least 150% e.g. at least 200% e.g. at least 250% e.g. at least 300% e.g. at least 350% e.g. at least 400% e.g. at least 500% of that of control cells when unstimulated. As described in more detail in the Examples section and as shown in FIG. 4, the greatest increase in the ILT3/CD86 ratio in unstimulated APCs as compared with control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta which was superior to use of retinoic acid and an AhR agonist.

Suitably, the APCs of the present invention (e.g. DCs of the invention) when stimulated, e.g. with an immunogenic stimulus such as LPS, have an ILT3/CD86 ratio which is at least 150% e.g. at least 200% e.g. at least 250% e.g. at least 300% e.g. at least 350% e.g. at least 400% e.g. at least 500% of that of control cells when stimulated e.g. with an immunogenic stimulus such as LPS. As described in more detail in the Examples section and as shown in FIG. 4, the greatest increase in the ILT3/CD86 ratio in stimulated APCs as compared with stimulated control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta which was superior to use of retinoic acid and an AhR agonist.

CD141 and GARP are when co-expressed tolerogenic APC markers. Tolerogenic APCs that co-express CD141 and GARP have been shown to be associated with enhanced capability to induce Tregs (Agrawal et al. 2016). CD141 and GARP may be co-expressed on the cell surface of both unstimulated and stimulated APCs, particularly DCs. CD141 and GARP co-expression and upregulation on tolerogenic APCs may not be dependent on an immunogenic stimulus, for example LPS. The frequency of CD141 and GARP co-expressing cells is typically much higher among tolerogenic cells than among non-tolerogenic cells. Desirable tolerogenic APCs, particularly DCs, have a high frequency of CD141 and GARP co-expressing cells when unstimulated or stimulated by immunogenic stimulus e.g. LPS.

The tolerogenic APCs of the present invention (e.g. DCs of the invention) in at least some embodiments have the merit of having a high degree of CD141 and GARP co-expression when unstimulated or stimulated, e.g. with an immunogenic stimulus such as LPS, compared to control cells when unstimulated or stimulated, respectively. Control cells are the same type of APCs from the same subject which have not been exposed to the tolerogenic compounds.

Suitably, the APCs of the present invention (e.g. DCs of the invention) when unstimulated, comprise a high frequency of cells co-expressing CD141 and GARP which is at least 400% e.g. at least 450% e.g. at least 500% e.g. at least 600% e.g. at least 700% e.g. at least 800% e.g. at least 900% e.g. at least 1000% of that of control cells when unstimulated. As described in more detail in the Examples section and as shown in FIG. 6, the greatest increase in the frequency of CD141 and GARP co-expressing cells among unstimulated APCs as compared with unstimulated control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and an AhR agonist which was superior to use of retinoic acid and TGFbeta. Use of the combination of retinoic acid, TGFbeta and an AhR agonist was superior to use of retinoic acid and TGFbeta.

Suitably, the APCs of the present invention (e.g. DCs of the invention) when stimulated e.g. with an immunogenic stimulus such as LPS, have a frequency of CD141 and GARP co-expressing cells which is at least 200% e.g. at least 250% e.g. at least 300% at least 400% e.g. at least 450% e.g. at least 500% of that of control cells when stimulated. As described in more detail in the Examples section and as shown in FIG. 6, the greatest increase in the frequency of CD141 and GARP co-expressing cells among stimulated APCs as compared with stimulated control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta.

IL-23 is a pro-inflammatory cytokine released from APCs, in particular DCs, during inflammation. Produced by DCs and macrophages, this cytokine promotes the protection of the host against mucosal pathogens through the induction of IL-17 and related cytokines by lymphocytes. IL-23 is generally only released from APCs, in particular DCs, when the cells are activated. Typically, unstimulated APCs, particularly DCs, show a level of production of IL-23 which does not differ greatly between tolerogenic cells and non-tolerogenic cells. However, when stimulated, e.g. with an immunogenic stimulus such as LPS or a pro-inflammatory cytokine cocktail, APCs, particularly DCs, may show an increased level of production of IL-23. The level of IL-23 production is typically increased much more in non-tolerogenic cells than in tolerogenic cells. Desirable tolerogenic APCs, particularly DCs, produce low levels of IL-23 when stimulated by immunogenic stimulus e.g. LPS or a pro-inflammatory cytokine cocktail. Desirable tolerogenic APCs, particularly DCs, are as resistant as possible to stimulation by immunogenic stimulus e.g. LPS or a pro-inflammatory cytokine cocktail with respect to IL-23 production.

The tolerogenic APCs of the present invention (e.g. DCs of the invention) in at least some embodiments have the merit of exhibiting low production of IL-23 when stimulated, e.g. with an immunogenic stimulus such as LPS or a pro-inflammatory cytokine cocktail, compared to control cells when stimulated, e.g. with an immunogenic stimulus such as LPS or a pro-inflammatory cytokine cocktail. They also exhibit low production of IL-23 when unstimulated. Control cells are the same type of APC from the same subject which have not been exposed to the tolerogenic compounds.

Suitably, the tolerogenic APCs of the present invention (e.g. DCs of the invention) when unstimulated have a level of production of IL-23 which is no more than 100% e.g. no more than 90%, e.g. no more than 80%, e.g. no more than 70% e.g. no more than 60%, e.g. no more than 50% of that of control cells when unstimulated.

Suitably, the APCs of the present invention (e.g. DCs of the invention) when stimulated, e.g. with an immunogenic stimulus such as LPS or a pro-inflammatory cytokine cocktail, have a level of production of IL-23 which is no more than 50% e.g. no more than 40% e.g. no more than 30% of that of control cells when stimulated e.g. with an immunogenic stimulus such as LPS or a pro-inflammatory cytokine cocktail. As described in more detail in the Examples section and as shown in FIG. 7, the level of production of IL-23 in stimulated APCs as compared with stimulated control cells was reduced when the APCs of the present invention were produced by the method of the invention when the tolerogenic compounds used were retinoic acid and an AhR agonist, retinoic acid and TGFbeta, and retinoic acid, TGFbeta and an AhR agonist.

The APCs of the present invention (e.g. DCs of the invention) in at least some embodiments also have the merit of having a level of production of IL-23 which is more resistant to further upregulating production after stimulation, e.g. with an immunogenic stimulus such as LPS or a pro-inflammatory cytokine cocktail, than control cells.

CD103 is a cell surface marker associated with intestinal tolerogenic DCs. Tolerogenic APCs that express CD103 have been shown to be able to maintain tolerance by inducing Tregs and protecting against tissue infection through cross-presentation of foreign antigens to CD8$^+$ T cells (Scott et al. 2011). CD103 expression can be upregulated on the cell surface of tolerogenic APCs, particularly DCs. CD103 expression and upregulation may not be dependent on an immunogenic stimulus, e.g. LPS. Typically, non-tolerogenic and tolerogenic APCs, particularly DCs, show a level of expression of CD103 which does not differ greatly between unstimulated and stimulated (e.g. with an immunogenic stimulus such LPS) conditions. The level of CD103 expression is typically increased much more in tolerogenic cells than in non-tolerogenic cells. Desirable tolerogenic APCs, particularly DCs, have a high level of expression of CD103 when unstimulated or stimulated by immunogenic stimulus e.g. LPS.

The tolerogenic APCs of the present invention (e.g. DCs of the invention) in at least some embodiments have the merit of having high CD103 expression when unstimulated or stimulated, e.g. with an immunogenic stimulus such as LPS, compared to control cells when unstimulated or stimulated, e.g. with an immunogenic stimulus such as LPS, respectively. Control cells are the same type of APC from the same subject which have not been exposed to the tolerogenic compounds.

Suitably, the APCs of the present invention (e.g. DCs of the invention) when unstimulated, have a level of expression of CD103 which is at least 150%, e.g. at least 200% e.g. at least 250% e.g. at least 300% of that of control cells when unstimulated. As described in more detail in the Examples section and as shown in FIG. 8, the greatest increase in the level of expression of CD103 in unstimulated APCs as compared with unstimulated control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and an AhR agonist which was superior to use of retinoic acid and TGFbeta. Use of the combination of retinoic acid, TGFbeta and an AhR agonist was superior to use of retinoic acid and TGFbeta.

Suitably, the APCs of the present invention (e.g. DCs of the invention) when stimulated, e.g. with an immunogenic stimulus such as LPS, have a level of expression of CD103 which is at least 200% e.g. at least 250% e.g. at least 300% of that of control cells when stimulated, e.g. with an immunogenic stimulus such as LPS. As described in more detail in the Examples section and as shown in FIG. 8, the greatest increase in the level of expression of CD103 in stimulated APCs as compared with stimulated control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta.

MERTK, BTLA, LAP, HLA-G and CD49b are cell surface markers of tolerogenic APCs, particularly DCs. MERTK, BTLA, LAP, HLA-G and CD49b can be expressed on the cell surface of tolerogenic APCs, particularly DCs.

The level of MERTK, BTLA, LAP, HLA-G and CD49b expression is typically much higher in tolerogenic cells than in non-tolerogenic cells. Desirable tolerogenic APCs, particularly DCs, have a high level of expression of MERTK, BTLA, LAP and HLA-G when unstimulated. Desirable tolerogenic APCs, particularly DCs, have a high level of expression of MERTK, BTLA, LAP, HLA-G and CD49b when unstimulated.

The tolerogenic APCs of the present invention (e.g. DCs of the invention) in at least some embodiments have the merit of having high MERTK, BTLA, LAP and HLA-G expression when unstimulated, compared to control cells when unstimulated. The tolerogenic APCs of the present invention (e.g. DCs of the invention) in at least some embodiments have the merit of having high MERTK, BTLA, LAP, HLA-G and CD49b expression when unstimulated, compared to control cells when unstimulated. Control cells are the same type of APC from the same subject which have not been exposed to the tolerogenic compounds.

Suitably, the APCs of the present invention (e.g. DCs of the invention) when unstimulated, have a level of expression of MERTK which is at least 120% e.g. at least 150% e.g. at least 175% of that of control cells when unstimulated. As described in more detail in the Examples section and as shown in FIG. 9 (A), the greatest increase in the level of expression of MERTK in unstimulated APCs as compared with unstimulated control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta.

Suitably, the APCs of the present invention (e.g. DCs of the invention) when unstimulated, have a level of expression of BTLA which is at least 120% e.g at least 150% e.g. at least 200% of that of control cells when unstimulated. As described in more detail in the Examples section and as shown in FIG. 9 (B), the greatest increase in the level of expression of BTLA in unstimulated APCs as compared with unstimulated control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta.

Suitably, the APCs of the present invention (e.g. DCs of the invention) when unstimulated, have a level of expression of LAP which is at least 120% e.g at least 150% e.g. at least 200% e.g. at least 250% of that of control cells when unstimulated. As described in more detail in the Examples section and as shown in FIG. 9 (C), the greatest increase in the level of expression of LAP in unstimulated APCs as compared with unstimulated control cells was obtained when the APCs of the present invention were produced by the method of the invention when the tolerogenic compounds used were retinoic acid, TGFbeta and an AhR agonist. Use of the combination of retinoic acid, TGFbeta and an AhR agonist was superior to use of retinoic acid and TGFbeta.

Suitably, the APCs of the present invention (e.g. DCs of the invention) when unstimulated, have a level of expression of HLA-G which is at least 120%, e.g. at least 150% e.g. at least 200% e.g. at least 250% e.g. at least 300% of that of control cells when unstimulated. As described in more detail in the Examples section and as shown in FIG. 9 (D), the greatest increase in the level of expression of HLA-G in unstimulated APCs as compared with unstimulated control cells was obtained when the APCs of the present invention were produced by the method of the invention when the tolerogenic compounds used were retinoic acid, TGFbeta and an AhR agonist.

The APCs (e.g. DCs) of the present invention when unstimulated suitably have high expression of ILT3 and low expression of CD83 and CD86 compared to control APCs when unstimulated. Also, the APCs (e.g. DCs) of the present invention when stimulated, e.g. with an immunogenic stimulus such as LPS, suitably have high expression of ILT3 and low expression of CD83 and CD86 compared to control APCs when stimulated, e.g. with an immunogenic stimulus such as LPS. Control cells are the same type of APC from the same subject which have, however, not been treated with the tolerogenic compounds according to the invention.

The level of expression of ILT3 in APCs (e.g. DCs) of the present invention when unstimulated suitably is at least 150% e.g. at least 175% e.g. at least 200% e.g. at least 250% e.g. at least 300% of that of control cells when unstimulated. The level of expression of CD83 in APCs (e.g. DCs) of the present invention when unstimulated suitably is no more than 110% e.g. no more than 100% of that of control cells when unstimulated. The level of expression of CD86 in APCs (e.g. DCs) of the present invention when unstimulated suitably is no more than 110% e.g. no more than 100% of that of control cells when unstimulated.

The level of expression of ILT3 in APCs (e.g. DCs) of the present invention when stimulated, e.g. with an immunogenic stimulus such as LPS suitably is at least 150% e.g. at least 175% e.g. at least 200% e.g. at least 250% e.g. at least 300% of that of control cells when stimulated, e.g. with an immunogenic stimulus such as LPS. The level of expression of CD83 in APCs (e.g. DCs) of the present invention when stimulated, e.g. with an immunogenic stimulus such as LPS suitably is no more than 70% e.g. no more than 60% e.g. no more than 50% of that of control cells when stimulated, e.g. with an immunogenic stimulus such as LPS. The level of expression of CD86 in APCs (e.g. DCs) of the present invention when stimulated, e.g. with an immunogenic stimulus such as LPS, suitably is no more than 80% e.g. no more than 70% e.g. no more than 60% e.g. no more than 50% of that of control cells when stimulated, e.g. with an immunogenic stimulus such as LPS.

The APCs (e.g. DCs) of the present invention when unstimulated or stimulated, e.g. with an immunogenic stimulus such as LPS, suitably express CD103 and most suitably have high expression of CD103 compared to control APCs when unstimulated or stimulated, e.g. with an immunogenic stimulus such as LPS, respectively. Control cells are the same type of antigen presenting cell from the same subject which have not been treated with the tolerogenic compounds according to the invention. The level of expression of CD103 in APCs (e.g. DCs) of the present invention when unstimulated or stimulated, e.g. with an immunogenic stimulus such as LPS, suitably is at least 200% e.g. at least 250% e.g. at least 300% of that of control cells when unstimulated or stimulated, e.g. with an immunogenic stimulus such as LPS, respectively.

The APCs (e.g. DCs) of the present invention when unstimulated suitably express CD103 (most suitably have high expression of CD103), and have high expression of CD141, GARP and ILT3 and low expression of CD83 and CD86 compared to control APCs when unstimulated. Also, the APCs (e.g. DCs) of the present invention when stimulated, e.g. with an immunogenic stimulus such as LPS, suitably express CD103 (most suitably have high expression of CD103), and have high expression of CD141, GARP and ILT3 and low expression of CD83 and CD86 compared to control APCs when stimulated, e.g. with an immunogenic stimulus such as LPS. Control cells are the same type of APCs from the same subject which have not been treated with the tolerogenic compounds according to the invention. The level of expression of CD103 in APCs (e.g. DCs) of the present invention when stimulated, e.g. with an immunogenic stimulus such as LPS suitably is at least 200% e.g. at least 250% e.g. at least 300% of that of control cells when stimulated, e.g. with an immunogenic stimulus such as LPS. The level of co-expression of CD141 and GARP in APCs (e.g. DCs) of the present invention when stimulated, e.g. with an immunogenic stimulus such as LPS, suitably is at least 200% e.g. at least 250% e.g. at least 300% at least 400% e.g. at least 450% e.g. at least 500% of that of control cells when stimulated, e.g. with an immunogenic stimulus such as LPS. The level of expression of ILT3 in APCs (e.g. DCs) of the present invention when stimulated, e.g. with an immunogenic stimulus such as LPS, suitably is at least 150% e.g. at least 175% e.g. at least 200% e.g. at least 250% e.g. at least 300% of that of control cells when stimulated, e.g. with an immunogenic stimulus such as LPS. The level of expression of CD83 in APCs (e.g. DCs) of the present invention when stimulated, e.g. with an immunogenic stimulus such as LPS, suitably is no more than 70% e.g. no more than 60% e.g. no more than 50% of that of control cells when stimulated, e.g. with an immunogenic stimulus such as LPS. The level of expression of CD86 in APCs (e.g. DCs) of the present invention when stimulated, e.g. with an immunogenic stimulus such as LPS, suitably is no more than 80% e.g. no more than 70% e.g. no more than 60% e.g. no more than 50% of that of control cells when stimulated e.g. with an immunogenic stimulus such as LPS.

The APCs (e.g. DCs) of the present invention, for example when unstimulated, suitably express (and suitably have a high expression of) one or more of (e.g. two, three or all four of) MERTK, BTLA, LAP and HLA-G compared to control APCs when unstimulated. The APCs (e.g. DCs) of the present invention, for example when unstimulated, suitably express (and suitably have a high expression of) one or more of (e.g. two, three or all four of) MERTK, BTLA, LAP, HLA-G and CD49b compared to control APCs when unstimulated. Control cells are the same type of APC from the same patient which have not been treated with the tolerogenic compounds according to the invention. The level of expression of MERTK in APCs (e.g. DCs) of the present invention when unstimulated suitably is at least 120% e.g. at least 150%, e.g. at least 175% of that of control cells when unstimulated. The level of expression of BTLA in APCs (e.g. DCs) of the present invention when unstimulated suitably is at least 120% e.g. at least 150%, e.g. at least 200% of that of control cells when unstimulated. The level of expression of LAP in APCs (e.g. DCs) of the present invention when unstimulated suitably is at least at least 150%, e.g. at least 200% e.g. at least 250% of that of control cells when unstimulated. The level of expression of HLA-G in APCs (e.g. DCs) of the present invention when unstimulated suitably is 120%, e.g. at least 150% e.g. at least 200% e.g. at least 250% e.g. at least 300% of that of control cells when unstimulated. The level of expression of CD49b in APCs (e.g. DCs) of the present invention when unstimulated suitably is 120%, e.g. at least 150% e.g. at least 200% e.g. at least 250% e.g. at least 300% of that of control cells when unstimulated.

The antigen presenting cells (e.g. DCs) of the present invention when stimulated, e.g. with an immunogenic stimulus such as LPS, suitably have low production of IL-23 compared to control APCs when stimulated, e.g. with an immunogenic stimulus such as LPS or a pro-inflammatory cytokine cocktail. Control cells are the same type of APC from the same subject which have not been treated with the tolerogenic compounds according to the invention. The level of production of IL-23 in APCs (e.g. DCs) of the present invention when stimulated, e.g. with an immunogenic stimulus such as LPS or a pro-inflammatory cytokine cocktail suitably is no more than 50% e.g. no more than 40% e.g. no more than 30% of that of control cells when stimulated, e.g. with an immunogenic stimulus such as LPS. The level of expression of CD86 in APCs (e.g. DCs) of the present invention when stimulated, e.g. with an immunogenic stimulus such as LPS, suitably is no more than 80% e.g. no more than 70% e.g. no more than 60% e.g. no more than 50% of that of control cells when stimulated, e.g. with an immunogenic stimulus such as LPS.

Suitably the tolerogenic APCs (e.g. DCs) of the invention are phenotypically stable e.g. with respect to their cell surface marker presentation, high Treg induction capability, low T cell proliferation induction capacity and other advantageous properties described herein.

Expression of cell surface markers may be evaluated using methods widely used and known in the art, for example flow cytometric analysis and the like.

Dose Regimen

A compound in the cell culture of the invention may be added to the culture in a suitable dose. Actual dosage levels of the compounds in the cell culture of the present invention may be varied so as to obtain an amount of the compound that is effective to achieve the desired tolerogenic effect on the cells without being toxic.

When retinoic acid is added to the cell culture, a suitable dose for retinoic acid may be, for example, in the range of from about 0.5 uM to about 10 uM. For example, a suitable dosage may be from about 0.5 uM to about 8 uM, 0.5 uM to about 6 uM, 0.5 uM to about 5 uM, 0.5 uM to about 4 uM, preferably 0.5 uM to about 3 uM.

When an AhR agonist is added to the cell culture, a suitable dose for an AhR agonist may be, for example, in the range of from about 1 nM to about 10 uM, typically from about 5 nM to about 2 uM e.g. about 5 nM to about 750 nM. For example, a suitable dosage may be from about 5 nM to about 500 nM, 5 nM to about 250 nM, 5 nM to about 100 nM, preferably 5 nM to about 50 nM. A suitable dose for an AhR agonist when it is not present in the cell culture is 0 nM.

When TGFbeta is added to the cell culture, a suitable dose for TGFbeta may be, for example, in the range of from about 1 ng/ml to about 200 ng/ml e.g. about 5 ng/ml to about 200 ng/ml, typically from about 5 ng/ml to about 150 ng/ml. For example, a suitable dosage may be from about 5 ng/ml to about 125 ng/ml, 5 ng/ml to about 100 ng/ml, 5 ng/ml to about 75 ng/ml, 5 ng/ml to about 50 ng/ml, preferably 5 ng/ml to about 30 ng/ml. A suitable dose for TGFbeta when it is not present in the cell culture is 0 ng/ml.

When retinoic acid, TGFbeta and AhR agonist are added to the cell culture, a suitable dose for retinoic acid may be, for example, in the range of from about 0.5 uM to about 10 uM. For example, a suitable dosage may be from about 0.5 uM to about 8 uM, 0.5 uM to about 6 uM, 0.5 uM to about 5 uM, 0.5 uM to about 4 uM, preferably 0.5 uM to about 3 uM. A suitable dose for the AhR agonist may be, for example, in the range of from about 1 nM to about 10 uM, typically from about 5 nM to about 2 uM e.g. about 5 nM to about 750 nM. For example, a suitable dosage may be from about 5 nM to about 500 nM, 5 nM to about 250 nM, 5 nM to about 100 nM, preferably 5 nM to about 50 nM. A suitable dose for TGFbeta may be, for example, in the range of from about 1 ng/ml to about 200 ng/ml e.g. about 5 ng/ml to about 200 ng/ml, typically from about 5 ng/ml to about 150 ng/ml. For example, a suitable dosage may be from about 5 ng/ml to about 125 ng/ml, 5 ng/ml to about 100 ng/ml, 5 ng/ml to about 75 ng/ml, 5 ng/ml to about 50 ng/ml, preferably 5 ng/ml to about 30 ng/ml.

When retinoic acid, TGFbeta and AhR agonist are added to the cell culture, a suitable dose for retinoic acid may be, for example, in the range of from about 0.5 uM to about 3 uM. A suitable dose for the AhR agonist may be, for example, in the range of from about 5 nM to about 50 nM, preferably about 20 nM. A suitable dose for TGFbeta may be, for example, in the range of from about 5 ng/ml to about 30 ng/ml, preferably about 20 ng/ml.

When retinoic acid, TGFbeta and AhR agonist are added to the cell culture, a suitable dose for retinoic acid may be, for example, in the range of from about 0.5 uM to about 3 uM, preferably about 2 uM. A suitable dose for the AhR agonist may be, for example, in the range of from about 5 nM to about 50 nM, preferably about 10 nM. A suitable dose for TGFbeta may be, for example, in the range of from about 5 ng/ml to about 30 ng/ml, preferably about 10 ng/ml.

Dosage regimens may be adjusted to provide the optimum desired response. For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the culture conditions used; each unit contains a predetermined quantity of active compound calculated to produce the desired therapeutic effect.

Compounds used in the cell culture of the invention may be administered alone or in combination with one or more compounds. One compound may be co-administered with one or more other compounds. Two compounds may be co-administered with one or more other compounds.

Combined administration of two or more compounds may be achieved in a number of different ways. Both may be administered together in a single composition, or they may be administered in separate compositions as part of a combined administration. For example, one or more, or two or more compounds may be administered before or separately, after or sequential, or concurrently or simultaneously with the other one or more compounds.

Treatment and Prevention of an Immune Reaction to an Antigen and Prevention of Immune Rejection The present invention provides a tolerogenic APC or population thereof for use in treating a mammalian subject with or at risk of an unwanted immune reaction to an antigen. The antigen may be any antigen discussed in the present specification, for example FVIII, FIX, an antibody, an antigen associated with a graft (e.g. an allograft), or a self-antigen.

The tolerogenic APCs generated by the culture method of the present invention may result in a tolerogenic APC or population thereof that is autologous. The autologous tolerogenic APCs used in the treatment may be obtained from autologous monocytes isolated from a sample taken from the same subject. The monocytes taken from the subject may be cultured with an antigen or epitope containing fragment thereof and autologous tolerogenic APCs subsequently obtained. The autologous tolerogenic APCs then have the capability to induce tolerance to the antigen when administered back to the subject.

The present invention further provides a tolerogenic APC or population thereof for use in a method of preventing rejection of an allograft in a recipient subject. The allograft may be kidney, pancreas, liver, lung, heart, skin graft, blood cell graft e.g. stem cell graft etc. Thus, the present invention provides for treatment of transplant rejection. The tolerogenic APCs used in the treatment may be obtained from monocytes isolated from a sample taken from a donor. The monocytes taken from the donor may be cultured and tolerogenic APCs obtained such that the tolerogenic APCs have the capability to induce tolerance to an antigen present in the allograft derived from the same donor.

The tolerogenic APCs used in the treatment may be obtained from monocytes isolated from a sample taken from the recipient. The monocytes taken from the recipient may be cultured with antigen or an antigen pool and tolerogenic APCs subsequently obtained. The tolerogenic APCs then have the capability to induce tolerance to an antigen present in the allograft derived from a donor. This method may be useful in such a case where derivation of monocytes from the donor is not possible, for example when the donor is not a live donor. The tolerogenic APCs derived the monocytes isolated from a sample taken from a recipient according to the invention may be used in treating immune rejection or in a method of preventing immune rejection of a xenograft.

The tolerogenic APCs of the present invention may be used in a manufacturing method. The present invention encompasses the use of the tolerogenic APCs or population thereof in the manufacture of a medicament for treating a mammalian subject with or at risk of an unwanted immune reaction. The method may comprise administering the tolerogenic APC or population thereof to the mammalian subject thereby establishing immune tolerance to the antigen. The present invention also encompasses the use the tolerogenic APCs or population thereof in the manufacture of a medicament for treating immune rejection of an allograft in a recipient subject where the graft is derived from a donor. The method may comprise administering the tolerogenic APC or population thereof to the recipient subject thereby establishing tolerance to the allograft, where the tolerogenic APC or population thereof is obtained from monocytes isolated from the sample taken from the donor or the recipient. Such manufacturing methods may also apply to xenografts when the tolerogenic APC or population thereof is derived from monocytes isolated from a sample taken from the recipient.

Mammals

Mammals from which a sample according to the method of the invention is obtained and mammals that may be treated by methods according to the invention include in particular humans (*Homo sapiens*). The mammal that may be treated by the methods of the present invention is preferably a human (*Homo sapiens*).

Sample

The method of the present invention may comprise isolating monocytes from any suitable sample from the subject. The sample may be a blood sample, a fractionated buffy coat sample, a leukapheresis material sample, or a PBMC sample. The sample used in the methods of the present invention is preferably a PBMC sample. The sample may be autologous, allogeneic or xenogeneic, preferably the sample is autologous or allogeneic.

Obtaining APCs from the Mammal

According to the invention, monocytes are first obtained from the mammal. One suitable method is to collect PBMCs by apheresis. PMBCs collected by apheresis may be kept under temperature controlled conditions, for example at ambient temperature, for example at 18° C.-25° C., or the PBMCs collected by apheresis may be frozen, for example at −4° C., −20° C. or −80° C. or lower. Alternatively, PBMCs may be isolated by density centrifugation. Monocytes may thereafter be positively selected from PBMCs using a solid phase, for example by plastic adherence or by using beads, e.g. anti-CD14 magnetic bead isolation.

Administration of Cells to the Subject

Cells may be administered back to the mammal by various routes e.g. intravenously, subcutaneously or intra-cutaneously, intranodal or directly at lesional sites where accessible for injections. The medium containing the cells suitably contains human albumin as a cell-protecting protein. Typically, an amount of $1\text{-}100\times10^7$ cells/dose in 1-10 doses at weekly to bi-weekly intervals is administered. The treatment can be extended, and dosing regimen can be changed until the desired tolerance is achieved.

Antigen

The antigen or epitope containing fragment thereof may be or be derived from a biological drug e.g. a protein drug (particularly a drug which is a protein comprising at least 50 or at least 200 or at least 1000 amino acid residues). Biological drugs may contain polysaccharide components.

Example biological drugs include blood factors (including e.g. FVIII or Factor IX), hormones (including insulin and EPO), growth factors (including EGF, IGF, KGF, HGF and FGF), cytokines (e.g. interleukins), enzymes (e.g. imiglucerase, rasburicase, imiglucerase, agalsidase beta, alglucosidase alfa, laronidase, idursulfase and galsulfase) and the like. Further examples include GCSF and analogues e.g. filgrastim and PEGylated versions thereof (such as pegfilgrastim) and interferons (e.g. interferon beta-1a). In one preferred aspect of the invention, the drug is FVIII. In another aspect of the invention, the drug is Factor IX. In the case of FVIII, various recombinant drugs are available including the commercial products ReFacto AF, Helixate NexGen, Kogenate Bayer, Kovaltry, Advate, NovoEight, Esperoct, Nuwiq, Beriate, Beriate P, Feiba, Haemoctin, Hemofil, Monoclate-P, Octanate [LV], Optivate and Recombinate. These products may be used as the antigen and epitope containing fragments may be derived from any of these products.

Further example biological drugs include engineered proteins (such as fusion and chimeric proteins) and recombinant proteins. In some embodiments the drug may be an antibody. The drug may, for example, be a monoclonal antibody, such as a humanized or fully human monoclonal antibody. The drug may also be a protein construct comprising fragments of immunoglobulin. The term antibody includes also bispecific antibodies, antibody-drug conjugates and antibody-nanoparticle conjugates as well as PEGylated or otherwise prolongated analogues. In some embodiments the antibody may be a domain antibody or antibody fragment including a single light chain antibody, VHH, scFv, Fab, F(ab')$_2$ or BiTE as well as PEGylated or otherwise prolongated analogues of such.

Example antibodies include infliximab (chimeric antibody, anti-TNFalpha), adalimumab (human antibody, anti-TNFalpha), basiliximab (chimeric antibody, anti-IL-2), abciximab (chimeric antibody, anti-GpIIb/IIIa), daclizumab (humanized antibody, anti-IL-2), gemtuzumab (humanized antibody, anti-CD33), alemtuzumab (humanized antibody, anti-CD52), edrecolomab (murine Ig2a, anti-EpCAM), rituximab (chimeric antibody, anti-CD20), palivizumab (humanized antibody, anti-respiratory syncytial virus), trastuzumab (humanized antibody, anti-HER2/neu(erbB2) receptor), bevacizumab (humanized antibody, anti-VEGF), cetuximab (chimeric antibody, anti-EGFR), eculizumab (humanized antibody, anti-complement system protein C5), efalizumab (humanized antibody, anti-CD11a), ibritumomab (murine antibody, anti-CD20), muromonab-CD3 (murine antibody, anti-T cell CD3 receptor), natalizumab (humanized antibody, anti-α4 integrin), nimotuzumab (humanized IgGI, anti-EGF receptor), omalizumab (humanized antibody, anti-IgE), panitumumab (human antibody, anti-EGFR), ranibizumab (humanized antibody, anti-VEGF), 1-131 tositumomab (humanized antibody, anti-CD20), ofatumumab (human antibody, anti-CD-20), certolizumab (humanized antibody, anti-TNFalpha), golimumab (human antibody, anti-TNFalpha), emicizumab (humanized bispecific antibody, anti-FIXa/FX), denosumab (human antibody, anti-RANK ligand) and concizumab (humanized antibody, anti-tissue factor pathway inhibitor).

Example biological drugs that are fusion proteins include etanercept.

An extensive list of biological protein drugs in clinical development and approved products are disclosed in the 2013 PhARMA report "Biologics"—https://web.archive.org/web/20161011093352/http://www.phrma.org/sites/default/files/pdf/biologics2013.pdf—which gives details of 907 biologics targeting more than 100 diseases. This document is incorporated by reference in its entirety. It is considered that the present invention may be used against these as well as other biological therapeutics where an immune response is developed in the treated subject.

Thus, the antigen or epitope containing fragment thereof for use in the method as described herein may for example be FVIII or a derivative or fragment thereof, or Factor IX or a derivative or fragment thereof, or an antibody or antibody fragment thereof.

The antigen or epitope containing fragment thereof may be associated with an allograft. Tolerogenic APCs that present antigens associated with allografts can be used for the treatment of allograft rejection.

The antigen or epitope containing fragment thereof may be or be derived from a self-antigen. Tolerogenic APCs that present self-antigens can be used for the treatment of autoimmune diseases. The range of self-antigens involved in autoimmune diseases include desmoglein 3, BP180, BP230, (pemphigus), dystonin and/or type XVII collagen (pemphigoid), myelin (multiple sclerosis), pancreatic beta cell proteins (Type 1 diabetes mellitus), nicotinic acetylcholine receptors (myasthenia gravis), neuronal surface proteins (autoimmune epilepsy and encephalitis), 2-hydrolase (autoimmune Addison's disease), FcεRI (chronic autoimmune urticaria) and acetylcholine receptor (myasthenia gravis), fibrillarin (scleroderma) and cardiolipin (systemic lupus erythematosus). These self-antigens, or epitope containing fragments thereof, can be used as the antigen in the method of the invention.

The antigen or epitope containing fragment may be unknown. Thus, an unknown antigen may be used in the culture method of the present invention. The unknown antigen may be associated with a tissue sample or extract thereof taken from the subject.

The antigen may be delivered from the exogenous culture medium across the cell membrane into the intracellular compartment by any appropriate antigen delivery method or vehicle. For example, the antigen delivery method or vehicle may be a nanoparticle. Thus, the antigen may be associated with a nanoparticle, i.e. an antigen-nanoparticle conjugate. The antigen-nanoparticle may be a FVIII-nanoparticle conjugate. The nanoparticle may be a lipid nanoparticle such as a vesicle or micelle.

Alternatively, the antigen delivery method of vehicle may be a cell penetrating peptide. The antigen may be fused to a cell penetrating peptide allowing for transport across a lipid bilayer membrane from the extracellular environment into the intracellular compartment. The cell penetrating peptide may be a Tat peptide from the trans-activating protein Tat of HIV1, the third helix of the homeodomain of antennapedia called penetratin or polyarginine. Cell penetrating peptides may be cell selective.

Immune Reactions and Use of Tolerogenic APCs of the Invention

The tolerogenic APCs of the invention are useful for inhibiting an undesired immune response in a subject receiving the cells. The undesired immune response may include an antibody response and/or a cellular response.

The tolerogenic APCs of the invention are, for example, suitable for the treatment of mammalian subjects who develop an immune response comprising the raising of ADAs to any drug capable of generating said response, for example any biological drug e.g. a protein drug.

The tolerogenic APCs of the invention are suitable for use in the treatment of mammalian subjects who develop an immune reaction to a drug including the raising of ADAs in a number of drug treatment situations, such as bleeding disorders (haemophilia A and B; respectively deficiency of FVIII and Factor IX), growth factor deficiency (deficiency of EGF, IGF, KGF, HGF, FGF etc), hormone deficiency (deficiency of EPO), enzyme replacement therapy (ADAs raised against, for example, imiglucerase (e.g., CER-EZYME™), a-galactosidase A (a-gal A) (e.g., agalsidase beta, FABRYZYME), acid a-glucosidase (GAA) (e.g., alglucosidase alfa, LUMIZYME™, MYOZYME™), and arylsulfatase B (e.g., laronidase, ALDURAZYME™, idursulfase, ELAPRASE™ galsulfase, NAGLAZYME™) and inflammatory and autoimmune disorders (e.g. anti-TNFalpha monoclonal antibodies).

The tolerogenic APCs of the invention are suitable for use in the treatment of mammalian subjects suffering from an autoimmune disease who have developed an immune response to a self-antigen capable of generating said response.

The tolerogenic APCs of the invention are suitable for use in the treatment of mammalian subjects suffering from or at risk of suffering from rejection of a graft e.g. an allograft who have developed or may develop an immune response to an antigen associated with the graft capable of generating said response.

Autoimmune Diseases or Disorders

The tolerogenic APCs according to the present invention may be useful in the treatment of autoimmune disease. Suitably, the autoimmune diseases or disorders are selected from the group consisting of achlorhydria, acquired haemophilia, acute haemorrhagic leukoencephalitis, acquired thrombocytopenic purpura, Addison's disease, alopecia areata, anemia, ankylosing spondylitis, anti-glomerular basement membrane disease, antiphospholipid syndrome, aplastic anemia, atopic allergy, autoimmune atrophic gastritis, autoimmune hearing loss, autoimmune hemolytic anemia, autoimmune hepatitis, autoimmune hypoparathyroidism, autoimmune hypophysitis, autoimmune lymphoproliferative, autoimmune myocarditis, autoimmune oophoritis, autoimmune orchitis, autoimmune polyendocrinopathy-candidiasis-ectodermal-dystrophy, autoimmune polyendocrinopathy, autoimmune sensineural hearing loss, autoimmune syndrome type II, autoimmune uveitis, Behcet's syndrome/disease, celiac disease, Chagas disease, chronic active hepatitis, chronic inflammatory demyelinating polyneuropathy, chronic lymphocytic thyroiditis, Churg-Strauss syndrome, Crohn's disease, cryoglobulinemia, Cushing syndrome, dermatitis herpetiformis, dermatomyositis, diabetes mellitus type 1,diffuse cerebral sclerosis of Schilder, epidermolysis bullosa acquisita, erythematosis, Felty's syndrome, glomerulonephritis, glomerulonephritis membranous, Goodpasture syndrome, granulomatosis with polyangiitis, Graves' disease, Guillain-Barre syndrome, Hamman-Rich syndrome, idiopathic thrombocytopenic purpura, inflammatory bowel disease, insulin resistance-type B, Lambert-Eaton myasthenic syndrome, lens-induced uveitis, lichen sclerosus et atrophicus, lymphopenia, Meniere's disease, microscopic polyangiitis, mixed connective tissue disease, Mooren's ulcer, mucocutaneous lymph node syndrome, multifocal motor neuropathy, multiple sclerosis, myasthenia gravis, myelitis transverse, myocarditis, narcolepsy, neuromyelitis optica, ocular cicatricial pemphigoid, oculovestibular auditory syndrome, ophthalmia sympathetic, opsoclonus-myoclonus syndrome, pancreatitis, pemphigoid bullous, pemphigus foliaceous, pemphigus vulgaris, polyarteritis nodosa, polymyalgia rheumatica, polyradiculoneuropathy, primary biliary cholangitis, primary biliary cirrhosis, psoriasis, Raynaud's disease, Reiter disease, relapsing polychondritis, rheumatic fever, rheumatoid arthritis, sarcoidosis, scleroderma, sclerosing colangitis, Sjögren's syndrome, stiff-person syndrome, adult-onset Still's disease, Takayasu's arteritis, temporal arteritis, thyrotoxicosis, type B Insulin resistance, ulcerative colitis, uveomeningoencephalitic syndrome, vitiligo and Wegener's granulomatosis.

Suitably, the autoimmune disease is diabetes mellitus type 1, rheumatoid arthritis, chronic lymphocytic thyroiditis, multiple sclerosis and ulcerative colitis.

In addition, diseases that can partly be involved with autoimmune reactivity are arteriosclerosis, Parkinson's disease, and Alzheimer's disease.

Cryo Preservation, Storage and Thawing

The tolerogenic APCs of the present invention may manufactured by a manual, semi-automated or a fully automated closed system. Cells of the invention (e.g. DCs of the invention) may be stored as a single cell suspension in a cryo preservation medium containing 2-10% DMSO (dimethyl sulfoxide). The cells may then be washed, preferably with physiologically sodium chloride buffer containing human serum albumin and resuspended in the cryo preservation medium, preferably at a range of $0.5$-$20 \times 10^6$ cells/ml and transferred into a cryo vial. The cells may thereafter be placed in a freezing container in a $-80°$ C. freezer. After 24 hours in the $-80°$ C. freezer, the cryo vials may be transferred to a $-150°$ C. freezer or liquid nitrogen tank for long-term storage. Preferably, cells of the invention (e.g. DCs of the invention) are cryopreserved below $-120°$ C.

Cells of the invention (e.g. DCs of the invention) may be thawed in the cryo vial until leaving only a small clump of ice before usage.

Storage and Transport

Cells of the invention (e.g. DCs of the invention) may be stored as single cells or in a multicellular aggregate. The single cells or multicellular aggregate may be entrapped or encapsulated in a hydrogel. Entrapping or encapsulating the cells in hydrogels can preserve their functionality at hypothermic temperatures and can be used to effectively store and/or transport multicellular aggregates whilst maintaining mechanical protection and retaining cell morphology, integrity, viability and function.

The single cell or multicellular aggregate may be encapsulated in the hydrogel in vitro. The cells typically have a structurally intact cell membrane, are viable or living cells and have a cell morphology that is representative of the cells of the invention (e.g. DCs of the invention). The hydrogel may be a coating that covers/surrounds completely or incompletely at least the majority of the single cell or multicellular aggregate in order to entrap the cell or aggregate in the hydrogel. A hydrogel coating may be formed separately from the single cell or multicellular aggregate and then placed over the single cell or multicellular aggregate. A hydrogel coating may comprise a layer of cross-linked alginate that is formed separately (i.e. spatially separate from) from the aggregate. Alternatively, the hydrogel coating may be formed in situ (i.e. in the presence of the single cell or multicellular aggregate).

The single cells or multicellular aggregate may be entrapped or encapsulated in a reversibly cross-linked hydrogel, e.g. an alginate hydrogel. A "reversibly cross-linked hydrogel" refers to a hydrogel that is formed by reversible cross-linking (i.e. the cross-linking can be reversed such that the hydrogel reverts back to a solution). Reversal of the cross-linking enables the entrapped or encapsulated multicellular aggregate(s) to be released from the hydrogel (e.g. at their point of use/after transportation or storage is complete). Examples of reversibly cross-linked hydrogels are well known in the art and suitable hydrogels may readily be identified by a person of skill in the art.

The hydrogel may comprise a hydrogel-forming polymer having a cross-linked or network structure or matrix; and an interstitial liquid. The hydrogel is capable of suppressing or preventing cell differentiation in aggregates encapsulated or entrapped therein. The hydrogel may be semi-permeable. The hydrogel may be a "hydrogel-forming polymer" which is capable of forming a cross-linked or network structure or matrix under appropriate conditions, wherein an interstitial liquid and a multicellular aggregate may be retained within such a structure or matrix. The hydrogel may comprise internal pores.

The hydrogel-forming polymer may be alginic acid or an alginate salt of a metal ion. Preferably, the metal is a Group 1 metal (e.g. lithium, sodium, or potassium alginate) or a Group 2 metal (e.g. calcium, magnesium, barium or strontium alginate). Preferably, the polymer is calcium alginate or sodium alginate or strontium alginate. The hydrogel-forming polymer may be a cross-linked acrylic acid-based (e.g. polyacrylamide) polymer. The hydrogel-forming polymer may be a cross-linkable cellulose derivative, a hydroxyl ether polymer (e.g. a poloxamer), pectin or a natural gum.

For multicellular aggregates, the cells may be directly or indirectly adjoined or connected to each other in a manner that forms an aggregate of cells. A matrix, substrate or scaffold, generically referred to as a "structure", may connect the adjoining cells into the aggregate. The structure may be a synthetic or natural polymer. Preferably, the structure is biodegradable. The structure may, for example, be a polymer comprising polylactic acid, collagen, nylon, e.g. a nylon mesh, collagen, gelatin, alginate, cellulose, glass or Matrigel.

The cells may be adjoined via an extracellular matrix (ECM), for example an Alvatex polystyrene scaffold for 3D cell culture. Alternatively, the multicellular aggregates may be structure free.

The single cells or multicellular aggregate encapsulated in a hydrogel may be packaged and sealed in a receptable for storage or transportation from a first location to a second location. The single cells or multicellular aggregate encapsulated in a hydrogel may have as storage stability time of at least 1 hour, at least 2 hours, at least 5 hours, at least 12 hours, at least 24 hours etc. The single cells or multicellular aggregate encapsulated in a hydrogel may be stored or transported within the hydrogel (and the sealed receptacle) at a temperature ranging from −80° C. to 45° C., preferably at 4 to 45° C., or at ambient temperature e.g. 10-25° C., preferably 15-20° C.

The single cells or multicellular aggregate encapsulated in a hydrogel may be stored or transported under cell culture conditions (e.g. about 37° C., about 5% $CO_2$ and about 95% humidity) or under chilled conditions, e.g. 4-6° C., preferably about 4° C. The single cells or multicellular aggregate encapsulated in a hydrogel may be refrigerated when stored or transported, e.g. 2-8° C. or 8-15° C. The single cells or multicellular aggregate encapsulated in a hydrogel may be stored or transported at Controlled Room Temperature (CRT) (which is defined as from 15 to 25° C.). They may be stored or transported cool or at CRT (i.e. from 8 to 25° C.). The single cells or multicellular aggregate encapsulated in a hydrogel may be stored or transported at hypothermic temperatures (i.e. below about 35° C., typically in the range of 0 to 32° C.).

The hydrogel comprising the multicellular aggregate may be frozen prior to storage and/or transportation. This may extend the time during which the cells of the multicellular aggregate are viable post-thawing and/or increase the usable transit-time. Hence the hydrogel may be used in this way as a post-cryoprotectant. For example, the temperature of the hydrogel comprising the aggregate may be reduced to below 0° C., below −15° C. or below −80° C. The hydrogel comprising the multicellular aggregate may or may not be allowed to defrost or thaw, i.e. to increase its temperature to above 0° C. during storage and/or transportation, preferably at a slow, controlled or uncontrolled rate of temperature increase. In other examples the hydrogels of the invention are not chilled or frozen.

The single cells or multicellular aggregate encapsulated in a hydrogel may be stored and/or transported for up to 10 or 20 weeks. Preferably, the single cell or multicellular aggregates are stored in the hydrogel for up to 1, 2, 3, 4, 5, 6, 7, 8, 9 or 10 weeks before being released from the hydrogels. More preferably, the single cell or multicellular aggregates are stored in the hydrogel for up to 1, 2, 3, 4, 5, 6, 7, 8, 9 or 10 days before being released from the hydrogels.

The single cell or multicellular aggregate may be released from the hydrogel by appropriate cell-compatible conditions, i.e. conditions which are not detrimental or not significantly detrimental to the cells and or the integrity of the cell's membrane. For example, the hydrogel may be dissociated by being chemically disintegrated or dissolves, e.g. using an appropriate alginate dissolving buffer.

Storage and/or transport for multicellular aggregated is described in WO2019142004, the contents of which are herein incorporated by reference in their entirety.

QC (Quality Control) Release Testing Assays

The RA+TGFbeta+AhR agonist treated DCs may be quality tested based on the expression of several different markers and on the capacity to reduce T cell proliferation in a MLR. For example, the RA+TGFbeta+AhR agonist treated DCs may express the markers CD11c, HLA-DR, CD80, CD83, CD86, ILT3, GARP, CD141, LAP, CD103, BTLA, HLA-G and CD49b. The RA+TGFbeta+AhR agonist treated DCs may preferably express at least CD11c, HLA-DR, CD80, CD83, CD86 and ILT3, more preferably at least CD11c, HLA-DR, CD80, CD83, CD86 and ILT3, even more preferably at least CD11c, HLA-DR, CD80, CD83, CD86, ILT3, GARP, CD141 and LAP. T cell proliferation may be evaluated by incorporation of $^3$H-thymidine, CFDA, CD25 expression and KI-67. T cell proliferation may preferably be evaluated by incorporation of $^3$H-thymidine, more preferably with CFDA, CD25 expression and incorporation of $^3$H-thymidine and even more preferably with CFDA, CD25 expression, KI-67 and incorporation of $^3$H-thymidine.

EXAMPLES

Materials and Methods for Examples 1-18 and 20-25

Isolation of Human Monocytes and T Cells

PBMCs were isolated by density centrifugation using Lymphoprep™ (StemCell Technologies, Vancouver, Canada) or using cell preparation tube (BD Bioscience, San Jose, United States). Monocytes were positively selected from PBMCs using anti-CD14 microbeads (Miltenyi Biotec, Bergisch Gladbach, Germany). CD4$^+$ T cells were purified using EasySep human CD4$^+$ T cell isolation kit (StemCell Technologies).

Generation of Dendritic Cells (DCs)

CD14$^+$ monocytes were cultured at $1.25 \times 10^6$ cells/mi for 7 days in GMP DC Medium (CellGenix, Freiburg, Germany) containing HEPES, GlutaMAX and Penicillin-Streptomycin solution (Thermo Fisher, Waltham, MA) in the presence of granulocyte-macrophage colony-stimulating factor (GM-CSF; 100 ng/ml; PeproTech, London, UK) and interleukin-4 (IL-4; 100 ng/ml; PeproTech). Cells were replenished on day 3 with fresh medium and cytokines. Control DCs were differentiated in GM-CSF and IL-4 without addition of any further compounds and optionally further were treated with lipopolysaccharide (LPS; 0.5 ug/ml; Sigma-Aldrich, Saint Louise, MO) or a pro-inflammatory cytokine cocktail consisting of TNFalpha (10 ng/ml; PeproTech), IL-1 beta (10 ng/ml; PeproTech), and prostaglandin E2 (PGE$_2$; 1 ug/ml; Sigma) on day 6 to generate stimulated immunogenic DCs. Tolerogenic DCs (tolDCs) were generated by treatment with various tolerogenic compounds: AhR agonist "C1" (C1; 20 nM; IMA-06201; Immunahr A B, Lund, Sweden) on days 0 and 3, TGFbeta1 (10 or 20 ng/ml; PeproTech) on day 3, and retinoic acid (2 uM; Sigma-Aldrich) on day 6. Control tolDC for comparison were established by treatment with Dexamethasone (Dex; 100 nM; Sigma-Aldrich) and Vitamin D3 (VitD3; 100 nM, StemCell Technologies) on day 3. Phenotypic stability of TolDCs was investigated by addition of LPS (0.5 ug/ml) or a pro-inflammatory cytokine cocktail consisting of TNFalpha (10 ng/ml), IL-1beta (10 ng/ml), PGE$_2$ (1 ug/ml), and for Example 24 also IL-6 (10 ng/ml), for the last 24 hours of culture. On day 7, DCs were harvested and washed extensively before phenotyping and functional assays were performed.

DC Phenotyping

Cell surface expression was investigated using the following fluorescently labeled antibodies: CD11c (B-Ly6), CD83 (HB15e), CD86 (BU63), ILT3 (ZM4.1), CD141 (M80), GARP (7611), CD103 (B-Ly7), MERTK (590H11G1E3), BTLA (J168-540), CD49b (P1E6-05), HLA-G (87G), LAP (FNLAP), from BD Biosciences (Franklin Lakes, NJ), BioLegend (San Diego, CA) and Thermo Fisher. DCs were washed and resuspended in staining buffer (phosphate-buffered saline supplemented with 0.5% BSA and 2 mM EDTA) and incubated with antibody for 20 min followed by washing before acquisition on a MACSQuant 10 flow cytometer (Miltenyi Biotec) and analyzed using FlowJo software (BD Biosciences). Live cells were discriminated from dead cells using Fixable Viability Dye (FVD) from Thermo Fisher.

DC Cytokine Production

IL-23 production was determined in supernatants from the DC cultures, with or without LPS or pro-inflammatory cytokine stimulation, using the Luminex platform (Invitrogen, Carlsbad, USA).

DC/T Cell Cultures: MLR and Treg Induction

In order to analyse the T cell stimulatory capacity of the generated DC populations, allogeneic MLRs were performed. DC/T cell cultures were carried out in complete medium: RPMI-1640 (Thermo Fisher) containing fetal bovine serum (FBS; 10%; Thermo Fisher), HEPES, GlutaMAX and Penicillin-Streptomycin solution. T cells ($10^5$ cells/well) were cultured with DCs at a T cell: DC ratio of 10:1 for 5-7 days. Proliferation was determined by incorporation of $^3$H-thymidine for the last 18 hours of culture. For determination of CD4$^+$CD49b$^+$LAG3$^+$ Tr1 cells, cells were phenotyped as described below. For determination of CD25$^{hi}$Foxp3$^+$ Treg induction, the T cells from the MLR cultures were rested for additionally 7 days in complete medium containing IL-2 (20 IU/ml; PeproTech) and then subjected to phenotyping as described below.

Treg Phenotyping

Cell surface and intracellular marker expression was investigated using the following fluorescently labeled antibodies: CD4 (A161A1), CD25 (M-A251), CD49b (P1E6-C5), LAG3 (11C3C65) and Foxp3 (259D/C7), from BD Biosciences and BioLegend. T cells were washed and resuspended in staining buffer and incubated with antibody for 20 min followed by washing, fixing, permeabilization and intracellular staining of Foxp3 using the Foxp3/Transcription Factor staining buffer set (eBioscience, Thermo Fisher). Live cells were discriminated from dead cells using Fixable Viability Dye (FVD) from Thermo Fisher. The flow cytometry analysis was performed as described above.

Freezing and Thawing of DCs

DCs were washed once and resuspended in cryomedium at a cell concentration of $10\text{-}20 \times 10^6$ cells/ml and transferred into cryo vials. These vials were placed into a freezing container and that was placed in a −80° C. freezer. The freezing container allowed a controlled freezing rate of approximately −1° C./min. After 24 hours in the −80° C. freezer cryo vials were transferred to a −150° C. freezer for long-term storage. Two different cryo media were tested; CryoStor (CS, Biolife solutions) with 10% DMSO (CS10), and conventional freezing medium with 10% DMSO, 50% human serum albumin and 40% cell culture medium. DCs were thawed in the vial in a water bath at 37° C. and the cell suspension were carefully transferred into a 15 ml tube containing cold GMP DC Medium (CellGenix) and washed once. Cells were thereafter stained according to the DC phenotyping method described above.

Example 1—Impact of Various Compounds on DC Expression of CD83

Various compounds were tested for their capacity to induce a tolerogenic phenotype in DCs, represented here, as one out of several factors, by low expression levels of the DC maturation marker CD83 and which in addition should be as resistant as possible to upregulation by immunogenic stimuli. Control DCs were differentiated from CD14$^+$ monocytes by culturing in GM-CSF and IL-4 for 7 days. Control DCs were either unstimulated or stimulated with LPS which was added on day 6 to generate immunogenic DCs. TolDCs, or less optimal variants thereof, were differentiated from CD14$^+$ monocytes by culturing in GM-CSF and IL-4 as above and by treatment with various tolerogenic compounds, as single agents or combinations to demonstrate synergistic effects of the claimed combinations, as depicted in FIGS. 1 (A) and (B): AhR agonist C1 (AhR ag) at 20 nM on days 0 and 3, TGFbeta at 20 ng/ml on day 3, and retinoic acid (abbreviated in this Example section and in the figures as 'RA') at 2 uM on day 6. TolDCs for comparison were established by treatment with Dex at 100 nM and VitD3 at 100 nM on day 3 (abbreviated in this Example section and in the figures as Dex/VitD3'). On day 6, some of the samples were treated with LPS to test for phenotypical stability (FIGS. 1 (A) and (B); black bars). All cells were harvested on day 7 and stained for CD83 cell surface expression using fluorescently labeled anti-CD83 antibodies followed by analysis by flow cytometry.

The mean fluorescence intensity (MFI) values on live cells are shown in FIGS. 1 (A) and (B) as mean±SD.

The results of FIG. 1 (A) show that the RA+TGFbeta and RA+TGFbeta+AhR agonist treated DCs expressed lower levels of CD83, whether or not stimulated with LPS, as compared to the corresponding control DCs and Dex/VitD3 treated comparator tolDCs. Treatment with RA+TGFbeta+AhR agonist was superior to treatment with RA+TGFbeta in reducing CD83 expression in DCs.

The results of FIG. 1 (B) show that the RA+TGFbeta, RA+TGFbeta+AhR agonist and RA+AhR agonist treated DCs expressed lower levels of CD83, when stimulated with LPS, as compared to the corresponding control DCs. Treatment with RA+TGFbeta+AhR agonist or RA+TGFbeta was superior to treatment with RA+AhR agonist, and furthermore was also superior to treatment with RA as a single agent in reducing CD83 expression in DCs.

Example 2—Impact of Various Compounds on DC Expression of CD86

Various compounds were tested for their capacity to induce a tolerogenic phenotype in DCs comprising, as one out of several factors, low expression levels of the costimulatory molecule CD86 and which in addition should be as resistant as possible to upregulation by immunogenic stimuli. Control DCs were differentiated from CD14$^+$ monocytes by culturing in GM-CSF and IL-4 for 7 days. Control DCs were either unstimulated or stimulated with LPS which was added on day 6 to generate immunogenic control DCs. TolDCs, or less optimal variants thereof, were differentiated from CD14$^+$ monocytes by culturing in GM-CSF and IL-4 as above and by treatment with various tolerogenic compounds, as single agents or combinations to demonstrate synergistic effects of the claimed combinations, as depicted in FIGS. 2 (A) and (B): AhR agonist C1 (AhR ag) at 20 nM on days 0 and 3, TGFbeta at 20 ng/ml on day 3, and RA at 2 uM on day 6. TolDCs for comparison were established by treatment with Dex at 100 nM and VitD3 at 100 nM on day 3. On day 6, some of the tolDCs were treated with LPS to test for phenotypical stability (FIGS. 2 (A) and (B); black bars). All cells were harvested on day 7 and stained for CD86 cell surface expression using fluorescently labeled anti-CD86 antibodies followed by analysis by flow cytometry.

The MFI values on live cells are shown in FIGS. 2 (A) and (B) as mean±SD.

The results of FIG. 2 (A) show that the RA+TGFbeta and RA+TGFbeta+AhR agonist treated DCs expressed lower levels of CD86, whether or not stimulated with LPS, as compared to the corresponding control DCs and Dex/VitD3 treated comparator tolDCs. Treatment with RA+TGFbeta+AhR agonist was superior to treatment with RA+TGFbeta in reducing CD86 expression in DCs.

The results of FIG. 2 (B) show that the RA+TGFbeta and RA+TGFbeta+AhR agonist treated DCs expressed lower levels of CD86, whether or not stimulated with LPS, as compared to the corresponding control DCs. RA+AhR agonist treated DCs expressed higher levels of CD86 compared to RA+TGFbeta and RA+TGFbeta+AhR agonist treated DCs when stimulated with LPS. RA treated DCs exhibited no resistance to upregulate CD86 upon LPS stimulation as compared to stimulated control DCs. Treatment with RA+TGFbeta+AhR agonist was superior to treatment with either RA+TGFbeta or RA+AhR agonist, and furthermore treatment with all three combinations was superior to RA as a single agent in reducing CD86 expression in DCs when stimulated with LPS.

Example 3—Impact of Various Compounds on DC Expression of ILT3

Various compounds were tested for their capacity to induce a tolerogenic phenotype in DCs comprising, as one out of several factors, high expression levels of the tolerogenic marker ILT3 and which in addition should be resistant to downregulation by immunogenic stimuli. Control DCs were differentiated from CD14$^+$ monocytes by culturing in GM-CSF and IL-4 for 7 days. Control DCs were either unstimulated or stimulated with LPS which was added on day 6 to generate immunogenic control DCs TolDCs, or less optimal variants thereof, were differentiated from CD14$^+$ monocytes by culturing in GM-CSF and IL-4 as above and by treatment with various tolerogenic compounds, as single agents or combinations to demonstrate synergistic effects of the claimed combinations, as depicted in FIGS. 3 (A) and (B): AhR agonist C1 (AhR ag) at 20 nM on days 0 and 3, TGFbeta at 20 ng/ml on day 3, and RA at 2 uM on day 6. TolDCs for comparison were established by treatment with Dex at 100 nM and VitD3 at 100 nM on day 3. On day 6, some of the tolDCs were treated with LPS to test for phenotypical stability (FIGS. 3 (A) and (B); black bars). All cells were harvested on day 7 and stained for ILT3 cell surface expression using fluorescently labeled anti-ILT3 antibodies followed by analysis by flow cytometry.

The MFI values on live cells are shown in FIGS. 3 (A) and (B) as mean±SD.

The results of FIG. 3 (A) show that the RA+TGFbeta and RA+TGFbeta+AhR agonist treated DCs expressed higher levels of ILT3, whether or not stimulated with LPS, as compared to the corresponding control DCs and Dex/VitD3 treated comparator tolDCs. Treatment with RA+TGFbeta+AhR agonist was superior to treatment with RA+TGFbeta in inducing ILT3 expression in DCs.

The results of FIG. 3 (B) show that the RA+AhR agonist, RA+TGFbeta and RA+TGFbeta+AhR agonist treated DCs expressed higher levels of ILT3, whether or not stimulated with LPS, as compared to the corresponding control DCs. Treatment with RA+TGFbeta+AhR agonist was superior to treatment with RA+TGFbeta or RA+AhR agonist, and furthermore treatment with RA+TGFbeta was superior to treatment with RA+AhR agonist in inducing ILT3 expression in DCs. Treatment with RA+TGFbeta+AhR agonist and RA+TGFbeta was superior to treatment with RA as a single agent in inducing ILT3 expression in DCs whether or not stimulated with LPS. Treatment with RA+AhR agonist was superior to treatment with RA as a single agent in inducing ILT3 expression in DCs when stimulated with LPS.

Example 4—Impact of Various Compounds on DC Tolerogenic Index ILT3/CD86

The optimal tolDCs should express both low levels of co-stimulatory molecules and high levels of tolerogenic molecules. Thus, to take into account the combined effect of this, the ratio between the expression levels of representative tolerogenic and co-stimulatory molecules could be depicted as a proxy for the tolerogenic capacity of a certain subset of tolDCs. FIGS. 4 (A) and (B) show such tolerogenic index, defined as the ILT3/CD86 expression (MFI) ratio, on DCs cultured under various conditions in the absence (FIG. 4 (A); grey bars) or presence of LPS (FIG. 4 (B); black bars).

The MFI values on live cells are shown in FIGS. 4 (A) and (B) as mean±SD.

The results of FIG. 4 (A) show that the RA+TGFbeta and RA+TGFbeta+AhR agonist treated DCs have a higher tolerogenic index than control DCs and Dex/VitD3 treated comparator tolDCs, and furthermore that RA+TGFbeta+AhR agonist treated DCs have a higher tolerogenic index than RA+TGFbeta treated DCs.

The results of FIG. 4 (B) show the same pattern as that of FIG. 4 (A). In particular, FIG. 4 (B) shows that the RA+AhR agonist, RA+TGFbeta and RA+TGFbeta+AhR agonist treated DCs have a higher tolerogenic index than stimulated control DCs. TolDCs treated with RA+TGFbeta+AhR agonist have a higher tolerogenic index than those treated with RA+TGFbeta which have a higher tolerogenic index than those treated with RA+AhR agonist. DCs treated with RA+TGFbeta+AhR agonist, RA+TGFbeta and RA+AhR agonist all have a higher tolerogenic index than DCs treated with RA as a single agent.

Example 5—Impact of Various Compounds on DCs and their Capacity to Induce T Cell Proliferation Various compounds were tested for their capacity to induce a tolerogenic phenotype in DCs which should translate into a reduced capacity to induce T cell proliferation which in addition should be as resistant as possible to be upregulated by immunogenic stimuli. Control DCs were differentiated from CD14+ monocytes by culturing in GM-CSF and IL-4 for 7 days. Control DCs were either unstimulated or stimulated with LPS which was added on day 6 to generate immunogenic control DCs. TolDCs, or less optimal variants thereof, were differentiated from CD14+ monocytes by culturing in GM-CSF and IL-4 as above and by treatment with various tolerogenic compounds, as single agents or combinations to demonstrate synergistic effects of the claimed combinations, as depicted in FIGS. 5 (A) and (B): AhR agonist C1 (AhR ag) at 20 nM on days 0 and 3, TGFbeta at 10 ng/ml (FIG. 5 (B)) or 20 ng/ml (FIG. 5 (A)) on day 3, and RA at 2 uM on day 6. TolDCs for comparison were established by treatment with Dex at 100 nM and VitD3 at 100 nM on day 3. On day 6, some of the DCs were treated with LPS (FIG. 5 (A); black bars) or a pro-inflammatory cytokine cocktail consisting of TNFalpha, IL-1beta and PGE$_2$ (FIG. 5 (B); black bars) to test for phenotypical stability under various conditions. All cells were harvested on day 7 and cocultures with CD4+ T cells were setup in an MLR setting at a T cell:DC ratio of 10:1. At the end of the 7-day cultures, proliferation of T cells was determined by ³H-thymidine incorporation.

The counts per minute (CPM) values from triplicate or more samples are shown in FIGS. 5 (A) and (B) as mean±SD.

The results of FIG. 5 (A) show that the RA+AhR agonist, RA+TGFbeta and RA+TGFbeta+AhR agonist treated DCs exhibited a lower capacity to induce T cell proliferation than the corresponding control DCs, including after LPS challenge. Treatment with RA+TGFbeta+AhR agonist was superior to treatment with RA+AhR agonist or RA+TGFbeta in reducing the capacity to induce T cell proliferation.

The results of FIG. 5 (B) show the same pattern as that of FIG. 5 (A). In particular, FIG. 5 (B) shows that the RA+AhR agonist, RA+TGFbeta and RA+TGFbeta+AhR agonist treated DCs exhibited a lower capacity to induce T cell proliferation than the corresponding control DCs, Dex/VitD3 treated comparator tolDCs and DCs treated with RA, TGFbeta, or AhR agonist as single agents, including after stimulation with the pro-inflammatory cytokine cocktail. Treatment with RA+TGFbeta+AhR agonist was superior to treatment with RA+AhR agonist or RA+TGFbeta in reducing the capacity to induce T cell proliferation.

Example 6—Impact of Various Compounds on DC Frequency of CD141+GARP+

Various compounds were tested for their capacity to induce a tolerogenic phenotype in DCs comprising, as one out of several factors, co-expression of CD141 and GARP. Control DCs were differentiated from CD14+ monocytes by culturing in GM-CSF and IL-4 for 7 days. Control DCs were either unstimulated or stimulated with LPS which was added on day 6 to generate immunogenic control DCs. TolDCs, or less optimal variants thereof, were differentiated from CD14+ monocytes by culturing in GM-CSF and IL-4 as above and by treatment with various tolerogenic compounds, as single agents or combinations to demonstrate synergistic effects of the claimed combinations, as depicted in FIGS. 6 (A) and (B): AhR agonist C1 (AhR ag) at 20 nM on days 0 and 3, TGFbeta at 10 ng/ml (FIG. 6 (A)) or 20 ng/ml (FIG. 6 (B)) on day 3, and RA at 2 uM on day 6. TolDCs for comparison were established by treatment with Dex at 100 nM and VitD3 at 100 nM on day 3. On day 6, some of the tolDCs were treated with LPS to test for phenotypical stability (FIG. 6 (B); black bars). All cells were harvested on day 7 and stained for cell surface expression using fluorescently labeled anti-CD141 and anti-GARP antibodies followed by analysis by flow cytometry.

The frequencies (%) of CD141+GARP+ among live cells are shown in FIGS. 6 (A) and (B) as mean±SD.

The results of FIG. 6 (A) show that the RA+AhR agonist, RA+TGFbeta and RA+TGFbeta+AhR agonist treated DCs comprise a higher frequency of CD141+GARP+ cells than control DCs, Dex/VitD3 treated comparator tolDCs and RA, TGFbeta, AhR agonist and TGFbeta+AhR agonist treated DCs. Treatment with RA+TGFbeta+AhR agonist was superior to treatment with RA+AhR agonist or RA+TGFbeta. RA+AhR agonist, RA+TGFbeta and RA+TGFbeta+AhR agonist treated DCs comprise a higher frequency of CD141+ GARP+ cells than DCs treated with TGFbeta or AhR agonist as a single agent or treated with Dex/VitD3. RA+AhR agonist and RA+TGFbeta+AhR agonist treated DCs comprise a higher frequency of CD141+GARP+ cells than DCs treated with RA.

The results of FIG. 6 (B) show that the RA+TGFbeta and RA+TGFbeta+AhR agonist treated DCs comprise a higher frequency of CD141+GARP+ cells than the corresponding control DCs and Dex/VitD3 treated comparator tolDCs, including after LPS stimulation. Treatment with RA+TGF-beta+AhR agonist was superior to treatment with RA+TGF-beta.

Example 7—Impact of Various Compounds on DC Production of IL23

Various compounds were tested for their capacity to induce a tolerogenic phenotype in DCs comprising, as one out of several factors, low production of the cytokine IL-23 in response to immunogenic stimuli. Control DCs were differentiated from CD14$^+$ monocytes by culturing in GM-CSF and IL-4 for 7 days. Control DCs were either unstimulated or stimulated with LPS which was added on day 6 to generate immunogenic control DCs. TolDCs, or less optimal variants thereof, were differentiated from CD14$^+$ monocytes by culturing in GM-CSF and IL-4 as above and by treatment with various tolerogenic compounds, as single agents or combinations to demonstrate synergistic effects of the claimed combinations, as depicted in FIGS. 7 (A) and (B): AhR agonist C1 (AhR ag) at 20 nM on days 0 and 3, TGFbeta at 10 ng/ml (FIG. 7 (B)) or 20 ng/ml (FIG. 7 (A)) on day 3, and RA at 2 uM on day 6. TolDCs for comparison were established by treatment with Dex at 100 nM and VitD3 at 100 nM on day 3. On day 6, some of the tolDCs were treated with LPS (FIG. 7 (A); black bars) or a pro-inflammatory cytokine cocktail consisting of TNFalpha, IL-1beta and PGE2 (FIG. 7 (B); black bars). Supernatants from the DC cultures were collected on day 7 and IL-23 levels were measured using the Luminex platform.

The IL-23 concentration values are shown in FIGS. 7 (A) and (B) as mean±SD.

The results of FIG. 7 (A) show that RA+AhR agonist, RA+TGFbeta, and RA+TGFbeta+AhR agonist treated DCs produced less IL-23 upon LPS activation as compared to stimulated control DCs. RA+TGFbeta was superior to RA+TGFbeta+AhR agonist and RA+AhR agonist in reducing IL-23 production.

The results of FIG. 7 (B) show a similar pattern as that of FIG. 7 (A). In particular, FIG. 7 (B) shows that the RA+AhR agonist, RA+TGFbeta and RA+TGFbeta+AhR agonist treated DCs produced less IL-23 upon stimulation by the pro-inflammatory cytokine cocktail as compared to the correspondingly stimulated control DCs and DCs treated with TGFbeta or AhR agonist as single agents or treated with TGFbeta+AhR agonist.

Example 8—Impact of Various Compounds on DC Expression of CD103

Various compounds were tested for their capacity to induce a tolerogenic phenotype in DCs comprising, as one out of several factors, high expression of the marker CD103. Control DCs were differentiated from CD14$^+$ monocytes by culturing in GM-CSF and IL-4 for 7 days. Control DCs were either unstimulated or stimulated with LPS which was added on day 6 to generate immunogenic control DCs. TolDCs, or less optimal variants thereof, were differentiated from CD14$^+$ monocytes by culturing in GM-CSF and IL-4 as above and by treatment with various tolerogenic compounds, as single agents or combinations to demonstrate synergistic effects of the claimed combinations, as depicted in FIGS. 8 (A) and (B): AhR agonist C1 (AhR ag) at 20 nM on days 0 and 3, TGFbeta at 10 ng/ml (FIG. 8 (A)) or 20 ng/ml (FIG. 8 (B)) on day 3, and RA at 2 uM on day 6. TolDCs for comparison were established by treatment with Dex at 100 nM and VitD3 at 100 nM on day 3. On day 6, some of the tolDCs were treated with LPS to test for phenotypical stability (FIG. 8 (B); black bars). All cells were harvested on day 7 and stained for cell surface expression using fluorescently labeled anti-CD103 antibodies followed by analysis by flow cytometry.

The MFI values on live cells are shown in FIGS. 8 (A) and (B) as mean±SD.

The results of FIG. 8 (A) show that RA+AhR agonist and RA+TGFbeta+AhR agonist treated DCs expressed higher levels of CD103 than RA, TGFbeta, RA+TGFbeta, control DCs and Dex/VitD3 treated comparator tolDCs. Treatment with RA+TGFbeta+AhR agonist was superior to treatment with RA+AhR agonist in inducing CD103 expression.

The results of FIG. 8 (B) show that the RA+TGFbeta+AhR agonist treated DCs whether or not stimulated with LPS, expressed higher levels of CD103 than control DCs and Dex/VitD3 treated comparator tolDCs. Treatment with RA+TGFbeta+AhR agonist was superior to treatment with RA+TGFbeta in inducing CD103 expression.

Example 9—Impact of Various Compounds on DC Expression of MERTK, BTLA, LAP, HLA-G and CD49b Various compounds were tested for their capacity to induce a tolerogenic phenotype in DCs consisting of expression of various tolerogenic markers. Control DCs were differentiated from CD14$^+$ monocytes by culturing in GM-CSF and IL-4 for 7 days. Control DCs were either unstimulated or stimulated with LPS which was added on day 6 to generate immunogenic control DCs. TolDCs were differentiated from CD14$^+$ monocytes by culturing in GM-CSF and IL-4 as above and by treatment with various tolerogenic compounds as depicted in FIG. 9 (A) to (E): AhR agonist C1 (AhR ag) at 20 nM on days 0 and 3, TGFbeta at 10 ng/ml (for MERTK and LAP, FIGS. 9 (A), (C) and (E)) or 20 ng/ml (for BTLA and HLA-G; FIGS. 9 (B) and (D)) on day 3, and RA at 2 uM on day 6. TolDCs for comparison were established by treatment with Dex at 100 nM and VitD3 at 100 nM on day 3. All cells were harvested on day 7 and stained for cell surface expression using fluorescently labeled anti-MERTK, anti-BTLA, anti-LAP, anti-HLA-G and anti-CD49b antibodies followed by analysis by flow cytometry.

The MFI values on live cells are shown in FIG. 9 (A) to (D) as mean±SD.

The results show that the RA+TGFbeta and RA+TGFbeta+AhR agonist treated DCs expressed higher levels of MERTK (FIG. 9 (A)), BTLA (FIG. 9 (B)) and LAP (FIG. 9 (C)) than control DCs and Dex/VitD3 treated comparator tolDCs. In all instances, treatment with RA+TGFbeta+AhR agonist was superior to treatment with RA+TGFbeta. In addition, RA+TGFbeta+AhR agonist treated DCs expressed higher levels of HLA-G and CD49b compared to control DCs and Dex/VitD3 treated comparator tolDCs as shown in FIGS. 9 (D) and (E), respectively.

Example 10—Impact of Various Compounds on DCs and their Capacity to Induce Tregs Various compounds were tested for their capacity to induce a tolerogenic phenotype in DCs which would translate into an enhanced induction of Treg cells upon T cell/DC co-cultures. Control DCs were differentiated from CD14$^+$ monocytes by culturing in GM-CSF and IL-4 for 7 days. Control DCs were either unstimulated or stimulated with LPS which was added on day 6 to generate immunogenic control DCs. TolDCs, or less optimal variants thereof, were differentiated from CD14+ monocytes by culturing in GM-CSF and IL-4 as above and by treatment with various tolerogenic compounds as depicted in FIGS. 10 (A) and (B): AhR agonist C1 (AhR ag) at 20 nM on days 0 and 3, TGFbeta at 20 ng/ml on day 3, and RA at 2 uM on day 6. TolDCs for comparison were established by treatment with Dex at 100 nM and VitD3 at 100 nM on day 3. On day 6, some of the tolDCs were treated with LPS to test for phenotypical stability (FIG. 10 (A); black bars). All cells were harvested on day 7 and co-cultures with CD4+ T cells were setup in an MLR setting at a T cell/DC ratio of 10:1. At the end of the initial 7-day cultures, T cells were washed and rested for an additional 7 days in medium containing IL-2. All cells were then harvested and stained for cell surface expression using fluorescently labeled anti-CD4 and anti-CD25 antibodies and for intracellular expression of Foxp3 using fluorescently labeled anti-Foxp3 antibodies followed by analysis by flow cytometry.

The frequencies (%) of CD25$^{hi}$Foxp3+ among live CD4+ T cells are shown in FIGS. 10 (A) and (B) as mean±SD.

The results of FIG. 10 (A) show that the RA+TGFbeta+AhR agonist and RA+TGFbeta treated DCs whether or not stimulated with LPS possessed an enhanced capacity to promote Treg induction compared to the corresponding control DCs. Treatment with RA+TGFbeta+AhR agonist was superior to treatment with RA+TGFbeta in inducing Tregs.

The results of FIG. 10 (B) show that the RA+TGFbeta+AhR agonist treated DCs possessed an enhanced capacity to induce Tregs compared to control DCs, Dex/VitD3 treated comparator tolDCs and TGFbeta+AhR agonist treated DCs. Furthermore, RA+AhR agonist treated DCs had an enhanced capacity to induce Tregs compared to control DCs and TGFbeta+AhR agonist treated DCs. Treatment with RA+TGFbeta+AhR agonist was superior to treatment with RA+AhR agonist in inducing Tregs.

Example 11—Impact of RA+TGFbeta+AhR Agonist on DCs Derived from the Blood of a Haemophilia a Patient in Relation to CD83, CD86, ILT3, ILT3/CD86, GARP+CD141+, CD103, LAP, IL-23 and CD49b+LAG3+Tr1 Cells The AhR agonist referred to in the Example is C1. A combination of RA+TGFbeta+AhR agonist was tested for its capacity to induce a tolerogenic phenotype in DCs, represented here, by low expression levels of the DC maturation marker CD83, low expression levels of the costimulatory molecule CD86, high expression levels of the tolerogenic marker ILT3, tolerogenic index, defined as the ILT3/CD86 expression, co-expression of CD141 and GARP, expression of CD103, expression of LAP, low spontaneous production of the cytokine IL-23, a reduced capacity to induce T cell proliferation and enhanced induction of Treg cell production. Control DCs were differentiated from CD14+ monocytes derived from a healthy donor or a subject with haemophilia by culturing in GM-CSF and IL-4 for 7 days. TolDCs, or less optimal variants thereof, were differentiated from CD14+ monocytes by culturing in GM-CSF and IL-4 as above and by treatment with a combination of RA+TGFbeta+AhR agonist, as depicted in FIG. 11 (A) to (J).

The MFI values on live cells are shown in FIG. 11 (A) to (G) as mean±SD.

The IL-23 concentration values are shown in FIG. 11 (H) as mean±SD.

The T cell proliferation assessed as counts per minute (CPM) values from triplicate or more samples are shown in FIG. 11 (I) as mean±SD.

The frequencies (%) of CD4+CD49b+LAG3+ Tr1 cells are shown in FIG. 11 (J) as mean±SD These results demonstrate that RA+TGFbeta+AhR agonist treated DCs generated from CD14+ monocytes isolated from blood from a haemophilia patient obtain a tolerogenic phenotype and function like that obtained with DCs generated from healthy donor blood. The results further demonstrate that RA+TGFbeta+AhR agonist treated DCs generated from CD14+ monocytes isolated from blood from a haemophilia patient shows the same reduced capacity to induce T cell proliferation and increase in regulatory T cell production as DCs generated from cells from healthy blood.

Example 12—Viability Experiment of DCs Treated with RA+TGFbeta+AhR Agonist

The AhR agonist referred to in the Example is C1. RA+TGFbeta+AhR agonist treated DCs were generated and tested for its viability, expression levels of the DC maturation marker CD83, expression levels of the tolerogenic marker ILT3, expression levels of the costimulatory molecule CD86, tolerogenic index, defined as the ILT3/CD86 expression, expression of LAP and expression of CD103 before and freezing/thawing. DCs were frozen in either conventional freezing medium or in CryoStor10 (CS, Biolife solutions). Control DCs were differentiated from CD14+ monocytes by culturing in GM-CSF and IL-4 for 7 days.

The viability before and after freezing are shown in FIG. 12 (A) as mean±SD.

The MFI values on live cells for CD83, ILT3, CD86, LAP and CD103 are shown in FIGS. 12 (B) to (D) and (F) to (G) as mean±SD.

The tolerogenic index, defined as the ILT3/CD86 expression (MFI) ratio are shown in FIG. 12 (E).

Table showing viability and recovery of RA+TGFbeta+AhR agonist treated DCs frozen in CS10 compared to conventional freezing medium (cony).

| Cell identity and freezing medium | Viability (%) | Recovery (%) |
|---|---|---|
| 1. conv | 45 | 37 |
| 1. CS10 | 80 | 61 |
| 2. conv | 49 | 54 |
| 2. CS10 | 75 | 74 |
| 3. conv | 82 | 94 |
| 3. CS10 | 91 | 92 |

The results presented in the Table above demonstrate that the cryopreservation and thawing of the RA+TGFbeta+AhR agonist treated DCs resulted in a useful cell viability and that DCs treated with RA+TGFbeta+AhR agonist have a greater viability compared to the control DCs. These results also demonstrate that the cryopreservation and thawing of the RA+TGFbeta+AhR agonist treated DCs resulted in a similar expression of surface markers as before freezing and that using CS10 results in better recovery and viability of the RA+TGFbeta+AhR agonist treated DCs compared to when cells have been cryo preserved standard freezing medium.

Example 13—Impact of Various Compounds on DCs in Relation to CD83, CD86, ILT3, ILT3/CD86, CD141+GARP+, CD103, T Cell Proliferation and CD25hiFoxp3+ Treg Cells Various compounds were tested for their capacity to induce a tolerogenic phenotype in DCs. TolDCs, or less optimal variants thereof, were differentiated from CD14$^+$ monocytes by culturing in GM-CSF and IL-4 as above and by treatment with various tolerogenic compounds, as single agents or combinations to demonstrate synergistic effects of the claimed combinations, as depicted in FIG. 13. AhR agonist C1 (AhR ag) at 10 nM on days 0 and 3, TGFbeta at 10 ng/ml on day 3, and RA at 2 uM on day 6. Control DCs were differentiated from CD14$^+$ monocytes by culturing in GM-CSF and IL-4 for 7 days. DCs were either unstimulated (grey bars) or stimulated with LPS (black bars) which was added on day 6, 2 hours after RA addition to generate immunogenic control DCs and test for phenotypical stability. All cells were harvested on day 7 and stained for cell surface expression using fluorescently labeled antibodies followed by analysis by flow cytometry.

The MFI values of on live cells for CD83, CD86, ILT3 and CD103 are shown in FIGS. 13 (A) to (C) and (E) as mean±SD.

The tolerogenic index, defined as the ILT3/CD86 expression (MFI) ratio are shown in FIG. 13 (D).

The frequencies (%) of CD141$^+$GARP$^+$ double positive cells are shown in FIG. 13 (F) as mean±SD.

The T cell proliferation assessed as counts per minute (CPM) values from triplicate or more samples are shown in FIG. 13 (G) as mean±SD.

The frequencies (%) of CD4$^+$CD25$^+$Foxp3$^+$ Tregs are shown in FIG. 13 (H) as mean±SD These results demonstrate that RA treated DCs have higher expression of ILT3 and a higher frequency of GARP$^+$ CD141$^+$ cells compared to control DCs, as seen in FIG. 13 C. RA treated DCs induce less T cell proliferation and more Tregs compared to control DCs, FIGS. 13 G and H.

AhR agonist treated DCs have a lower expression of CD83 and CD86 and a higher expression of CD103 compared to control DCs, as seen in FIGS. 13A, B and E, respectively. AhR agonist treated DCs induce slightly more T cell proliferation and slightly more Tregs, when not stimulated with LPS, compared to control DCs, (FIGS. 13 (G) and (H)).

TGFbeta treated DCs have a slightly higher tolerogenic ratio (ILT3/CD86) and CD103 expression compared to control DCs, (FIG. 13 (D-E)). Moreover, TGFbeta treated DCs induce less T cell proliferation and more Tregs compared to control DCs, (FIG. 13 (G) to (H)).

RA+TGFbeta treated DCs have a lower expression of CD83 and CD86 and a higher expression of ILT3 compared to control DCs, FIGS. 13A, B and C, respectively. RA+TGFbeta treated DCs also have a higher frequency of GARP$^+$CD141$^+$ cells compared to control DCs, (FIG. 13 (F)). RA+TGFbeta treated DCs induce less T cell proliferation when used in combination compared to one by one, (FIG. 13 (G)). In summary, TGFbeta strengthens the tolerogenic effect of RA.

RA+AhR agonist treated DCs shows a lower expression of CD83, CD86 and a higher expression of ILT3 and CD103 compared to control DCs, FIGS. 13A, B, C and E, respectively. RA+AhR agonist treated DCs also have a higher frequency of GARP$^+$CD141$^+$ cells compared to control DCs but not as high as RA+TGFbeta or RA+TGFbeta+AhR agonist treated DCs, (FIG. 13 (F)). RA+AhR agonist treated DCs induce less T cell proliferation when used in combination compared to one by one, (FIG. 13 (G)). In summary, the AhR agonist strengthens the tolerogenic effect of RA.

Using the AhR agonist together with RA+TGFbeta for generation of tolerogenic DCs results in a higher tolerogenic ratio and a higher CD103 expression, (FIGS. 13 (D) and (E).

Moreover, the induction of Tregs is slightly higher when using RA+TGFbeta+AhR agonist compared to RA+TGF-beta, (FIG. 13 (H)).

Example 14—Impact of RA+TGFbeta+AhR Agonist on DCs and their Capacity to Suppress Tetanus Toxoid T Cell Proliferation The AhR agonist referred to in the Example is C1.
Additional Materials and Methods
Generation of TT Loaded Dendritic Cells (DCs)

CD14$^+$ monocytes were cultured at $1.25 \times 10^6$ cells/ml for 7 days in GMP DC Medium (CellGenix, Freiburg, Germany) containing HEPES, GlutaMAX and Penicillin-Streptomycin solution (Thermo Fisher, Waltham, MA) in the presence of granulocyte-macrophage colony-stimulating factor (GM-CSF; 100 ng/ml; PeproTech, London, UK) and interleukin-4 (IL-4; 100 ng/ml; PeproTech). Cells were replenished on day 3 with fresh medium and cytokines. Control DCs were differentiated in GM-CSF and IL-4 without addition of any further compounds and for antigen loaded cells, TT (30 nM) was added to the culture 4 hours before with treated with a pro-inflammatory cytokine cocktail consisting of TNFalpha (10 ng/ml; PeproTech), IL-1 beta (10 ng/ml; PeproTech), and prostaglandin E2 (PGE$_2$; 1 ug/ml; Sigma) on day 6 to generate immunogenic DCs. TolDCs) were generated by treatment with the tolerogenic compounds AhR agonist TGFbeta1 and RA as described previously. For antigen loaded cells, TT (30 nM) was added to the culture 2 hours after RA addition on day 6. On day 7, DCs were harvested and washed extensively before phenotyping and functional assays were performed.
Freezing and Thawing of PBMCs PBMCs were resuspended in cryomedium containing 10% DMSO and transferred into cryo vials. These vials were placed into a freezing container and that was placed in a −80° C. freezer. The freezing container allowed a controlled freezing rate of approximately −1° C./min. After 24 hours in the −80° C. freezer cryo vials were transferred to a −150° C. freezer for long-term storage. PBMCs were thawed in the vial in a water bath at 37° C. and the cell suspension were carefully transferred into a 15 ml tube containing cold RPMI with 10% FCS and supplemented with DNase and washed once before use.
Autologous DC/T Cells Cultures In order to analyse the TT specific T cell response, DCs loaded with 30 nM TT and stimulated with TNF-α, IL-1β, PGE2 and IL-6 matured DCs (mDCs) and TT loaded RA+TGFbeta+AhR agonist treated DCs were cultured together with autologous T cells at a T cell:DC ratio of 10:1 for 6 days. mDCs, with or without TT, together with autologous T cells were used as control. DC/T cell cultures were carried out in complete medium: CTS™ OpTmizer™ T Cell Expansion medium with OpTmizer™ T-Cell Expansion Supplement (Thermo Fisher) and Penicillin-Streptomycin solution. Proliferation was determined by incorporation of 3H-thymidine for the last 18 hours of culture.

RA+TGFbeta+AhR agonist treated DCs were loaded with TT and co-cultured with autologous, TT loaded mDCs and T cells to study the TT specific reduction in T cell proliferation induced by the RA+TGFbeta+AhR agonist treated DCs. Unloaded cells, both mDCs and RA+TGFbeta+AhR agonist treated DCs, were used as controls.

The T cell proliferation assessed as counts per minute (CPM) values from triplicate samples are shown in FIG. 14 as mean±SD.

These results demonstrate that TT loaded RA+TGFbeta+AhR agonist treated DCs suppresses mDC induced, TT specific T cell proliferation.

Example 15—Impact of RA+TGFbeta+AhR Agonist on DCs in Relation to CD83, LAP, CD103, ILT3, CD86, ILT3/CD86 and T Cell Proliferation Following CD40L Treatment Additional Materials and Methods Phenotypic Stability and Sustained Tolerogenicity after CD40L Stimulation On day 7 phenotypic stability and sustained tolerogenicity of TolDCs was investigated by addition of CD40L (100 ng/ml) after harvest. Cells were stimulated for 24 hours and DCs were thereafter harvested and washed extensively before phenotyping and functional assays were performed.

These results demonstrate that RA+TGFbeta+AhR agonist treated DCs shows a stable phenotype after stimulation with CD40L, mimicking DC: T cell contact (FIG. 15 (A) to (F)). These results further demonstrate that RA+TGFbeta+AhR agonist treated DCs after stimulation with CD40L have a comparable capacity to induce T cell proliferation as RA+TGFbeta+AhR agonist treated DCs that were unstimulated (FIG. 15 (G)). In conclusion, these results demonstrate that RA+TGFbeta+AhR agonist treated DCs shows a sustained phenotype and tolerogenicity after stimulation with CD40L.

Example 16—Impact of RA+TGFbeta+AhR Agonist on DCs to Take Up Antigens of Various Sizes and to Maintain a Stable Tolerogenic Phenotype The AhR agonist referred to in the Example is C1.

Additional Materials and Methods

Antigen Loading of DCs

At day 3, 6 or 7 of culture, 100 nM FITC labelled Dextran, 1-10 pg/mL AF488 labelled KLH, 100 nM AF488 labelled tetanus toxoid (TT) or 10-100 nM FVIII was added to the culture of RA+TGFbeta+AhR agonist treated DCs for antigen loading. Antigen uptake was detected by flow cytometry. For FVIII detection, cells were stained with a FVIII specific, FITC labelled antibody after fixation and permeabilization. DC phenotypic analysis was performed on DCs loaded with 60 nM FVIII for 2, 4, 8 or 20 hours. Percentage antigen positive cells was compared to RA+TGFbeta+AhR agonist treated DCs cultured without antigen.

Percentages of FITC-Dextran, AF488-KLH or AF488-TT positive, CD11c+RA+TGFbeta+AhR agonist treated DCs at day 7, after culture from day 3 to day 7 with the fluorescently labelled antigens (FIG. 16 (A)). For FVIII uptake, RA+TGFbeta+AhR agonist treated DCs were cultured in the presence of 10, 30 or 100 nM FVIII from day 3 to day 7 (FIG. 16 (B)). On day 7, cells were stained for CD11c and thereafter permeabilized and fixed to allow intracellular staining with a FITC labelled FVIII specific antibody (Sanquin, the Netherlands).

RA+TGFbeta+AhR agonist treated DCs were cultured in the presence of 60 nM FVIII for 2, 4, 8 or 20 hours on day 7 to determine the phenotype of the cells in the presence of FVIII (FIG. 16 (C) to (I)).

These results demonstrate that RA+TGFbeta+AhR agonist treated DCs have the capacity to take up a diverse range of antigens of various sizes and chemical classes. These results also demonstrate that RA+TGFbeta+AhR agonist treated DCs have the capacity to take up antigens at different time points of the culture and have a stable phenotype after loading with FVIII at different time points.

Example 17—Impact of RA+TGFbeta+AhR Agonist on DCs to Affect the Levels of Bregs, B Cells and T Cells, T Cell Proliferation and Activation The AhR agonist referred to in the Example is C1.

Additional Materials and Methods

B Cell/T Cell/DC Cultures: Breg Induction

On day 7, autologous B cells were isolated from PBMCs by negative selection using Human B cell isolation kit (StemCell technologies). 40 000 B cells were cultured together with 40 000 autologous T cells, isolated with EasySep human CD4+ T cell isolation kit (StemCell technologies) as described above, and 10 000 RA+TGFbeta+AhR agonist treated DCs or control DCs generated as described above. Selected cultures were stimulated with 0.25 µM CpG-OGN to enhance the response. Breg induction was assessed by intracellular IL-10 staining, T cell proliferation determined by KI67 staining and T cell activation by CD154 expression. Staining for IL-10, KI67 and CD154 were performed as described above using the following fluorescently labelled antibodies were used: IL-10 (JES3-9D7) from Biolegend and KI67 (B56) and CD154 (TRAP1) from BD.

These data demonstrate that the frequency of Bregs, determined as IL-10$^+$CD19$^+$ cells, after co-culture of autologous DCs, B cells and T cells are increased in the presence of RA+TGFbeta+AhR agonist treated DCs compared to when co-cultured with control DCs as shown in FIG. 17 (A). T cells proliferation and activation was determined by assessing KI67 (FIG. 17 (B)) and CD154 (FIG. 17 (C)), respectively, after co-culture of autologous DCs, B cells and T cells.

Bregs are immune regulatory cells with the ability to suppress other immune cells' activity. Bregs are also antigen presenting cells. By inducing Bregs, another level of immune suppression will be activated and Bregs can work in synergy with Tregs. These results demonstrate that RA+TGFbeta+AhR agonist treated DCs cultured together B cells and T cells induce more IL-10 producing Bregs compared to when cultured together with control DCs. Furthermore, these results demonstrate that RA+TGFbeta+AhR agonist treated DCs cultured together B cells and T cells induce less T cell proliferation and activation compared to control DC. A reduced T cell proliferation and activation indicates induction of regulatory cells, either Bregs, Tregs or both.

Example 18—Impact of RA+TGFbeta+AhR Agonist on DCs Derived from Donor Blood when Cultured with Allogeneic PBMCs DCs generated from monocytes isolated from four healthy donors (named A-D) were treated with RA+TGFbeta+AhR agonist. The RA+TGFbeta+AhR agonist treated DCs showed the same expression profile as described in previous examples with a low expression levels of CD83 and CD86, high expression ILT3, CD103 and LAP and a high tolerogenic index, defined as the ILT3/CD86 expression.

The RA+TGFbeta+AhR agonist treated DCs from donors A-D were cultured together with allogeneic PBMCs. For example, donor A derived DCs were cultured with PBMCs from donor B, C and D in the MLR. The RA+TGFbeta+AhR agonist treated DCs had varying capacity to induce T cell proliferation when co-cultured with allogeneic PBMCs, FIG. 18 (A). Moreover, the RA+TGFbeta+AhR agonist treated DCs had varying capacity to induce Tregs in a MLR with allogeneic PBMCs, FIG. 18 (B).

T cell proliferation was assessed as frequency of KI67+ cells for RA+TGFbeta+AhR agonist treated DCs and control DCs are shown in FIG. 18 (A).

The frequencies (%) of Tregs (CD4$^+$CD25$^+$Foxp3$^+$) for RA+TGFbeta+AhR agonist treated DCs and control DCs are shown in FIG. 18 (B).

These results demonstrate that the majority of donor RA+TGFbeta+AhR agonist treated DCs reduced T cell proliferation and increased Treg induction when co-cultured together with allogeneic PBMCs. Furthermore, these results indicate that the level of mismatch, that can be evaluated by HLA typing, can influence the outcome of the tolerogenic response induced by RA+TGFbeta+AhR agonist treated DCs.

Example 19—Clinical Trial Study

The study will comprise two periods: an initial dose escalation part (part 1) and an extended study part (part 2).
First study part (Group 1): In the first part of the trial, the safety of ascending dosing will be evaluated. There will be four subjects. Additional subjects can be included upon safety review by the Internal Monitoring Board (IMB). Patient 1 will receive three doses of cells at two-week intervals. The IMB will decide whether dose escalation can be done after patient 1 has received the last dose. Patient 2 will receive the first dose of cells at least two weeks after the last dose given to patient 1 and an additional two more doses at two-week intervals. Patient 3 will receive the first dose at least two weeks after the second patient's last dose, and another two doses at two-week intervals. Patient 4 is given the first dose at least two weeks after the third patient's last dose followed by two more doses at two-week intervals. In case the production yield does not reach the predetermined dose, the patient will receive all the harvested cells, and another patient will be included in the study.
Extended second study part (Group 2): There will be eight subjects. After completion of the dose escalation trial part (part 1), the extended part 2 of the study is to be started. The IMB will evaluate Group 1 after the last dose, before proceeding with the extended part 2 of the trial (Group 2). Once the safety of the ascending doses given to the study subjects in Group 1 has been established, eight patients in Group 2 (No. 5, 6, 7, 8, 9, 10, 11, and 12) will be given 3 i.v. injections every second week with the highest tolerated dose determined in Group 1, or the highest obtained production yield but not exceeding the highest tolerated dose determined in Group 1.
Procedure for producing the active substance and transfer to each investigating clinic: Peripheral blood mononuclear cells are to be collected from the patient via aphaeresis. Fresh leukapheresis material is to be sent to a GMP facility (Radboud University Medical Center, Nijmegen, Netherlands), where monocytes are enriched and cultured with a mixture of compounds that differentiate the monocytes into dendritic cells. Idogen's tolerance-inducing cocktail then converts these dendritic cells into tolerogenic dendritic cells which then, as a final step, are loaded with recombinant FVIII (Kovaltry®, Octocog alpha). The cells are then cryopreserved and will be sent back to each investigating site. Route of administration: Intravenous administration of cells. The cryopreserved cell suspension will be thawed and given directly i.v. at the respective clinical site.

When patients develop antibodies to FVIII, the first treatment option is to do an ITI therapy with high doses of FVIII. However, ITI is not always successful. It is an extremely expensive treatment that usually extends over 1 year requiring daily injections and it fails in ⅓ of the patients (Aledort 2019, Carcao 2019, Lacroix-Desmazes 2020, Ljung 2019). It is burdensome, especially to the often very young children developing inhibitors. The increase in morbidity and healthcare costs associated with inhibitors (bleeding into joints and muscles, etc.) (D'Angiolella 2018, CDC (Centers for Disease Control and Prevention) Jun. 3, 2019) stresses the urgency to identify strategies that would prevent inhibitors from developing at all.

Idogen's phase I/11a trial will include HA study subjects with inhibitors to FVIII, having an active immune response towards FVIII, which has not been suppressed by the established treatment protocol for ITI. This patient category has no other standard treatment alternatives left for eradicating their inhibitors towards FVIII. The risk of the trial is unknown, though no severe safety issues have been reported from published clinical trials with autologous tolerogenic dendritic cell therapies (Bell 2017, Benham 2015, Dhodapkar 2001, Dhodapkar and Steinman 2002, Giannoukakis 2011, Harry 2010, Hilkens and Isaacs 2013, Jauregui-Amezaga 2015, Joo 2014, Ten Brinke 2015, Thomas 2011, Willekens and Cools 2018, Willekens 2019, Zubizarreta 2019) and the cells show a tolerogenic phenotype in in vitro experiments (Lee 2016, Gordon 2014, Lutz 2000, Steinbrink 1997, Bartosik-Psujek 2010, Huang 2001, Hussien 2001, Bellinghausen 2012, Boks 2012, Chu 2012, Raich-Regue 2012, Saito 2011). Nonetheless, it cannot be excluded that serious adverse events with a suspected relationship to the treatment can occur. Prophylactic cover with antihistamines will be given to patients in conjunction with the administration of ItolDC-028.

A potential risk in trials involving subjects with bleeding diathesis is the occurrence of bleeds during blood sampling, leukapheresis or cell infusion. However, bleeds after puncture are rare in experienced hands and the subjects will be handled by personnel well-versed in managing patients with bleeding disorders. If venipuncture is traumatic, digital pressure on the puncture site or a pressure dressing may prevent further complications. Subcutaneous, intracutaneous, and small intramuscular injections seldom produce hematomas if firm finger pressure is maintained for at least 5 minutes (Powell and Rodgers 2013).

Example 20—Impact of RA+TGFbeta+AhR Agonist on DCs Derived from the Blood of a Patient with an Autoimmune Disease in Relation to B Cell Production of IL-10 and T Cell Regulatory Function RA+TGFbeta+AhR agonist treated DCs are generated from monocytes from a patient having an autoimmune disease with one or several well characterized antigens. RA+TGFbeta+AhR agonist treated DCs are loaded with the one or several well characterized antigens. DCs may thereafter be co-cultured with autologous T cells. The T cells will be less activated compared to T cells co-cultured with control DCs loaded with the same antigens. Moreover, in the co-culture with RA+TGFbeta+AhR agonist treated DCs and T cells, a higher frequency of regulatory T cells will be induced compared to T cells co-cultured with control DCs under the same conditions.

RA+TGFbeta+AhR agonist treated DCs generated from a patient with an autoimmune disease are co-cultured together with B cells. The B cells will have a higher frequency of regulatory markers such as IL-10.

RA+TGFbeta+AhR agonist treated DCs generated from a patient with an autoimmune disease are co-cultured with B cells and T cells. The T cells will have an increased regulatory function compared to B cells and T cells co-cultured with control DCs.

The induction of a tolerogenic phenotype and function of both T cells and B cells after co-culture with RA+TGFbeta+AhR agonist treated DCs is beneficial in autoimmune diseases as these cells dampen the autoreactive activity of T and B cells.

Example 21—Impact of RA+TGFbeta+AhR Agonist on DCs Derived from the Blood of a Patient with an Autoimmune Disease and Treated with Several Unknown and/or Complex Antigens or Tissue Sample in Relation to B Cell Production of IL-10 and T Cell Regulatory Function RA+TGFbeta+AhR agonist treated DCs are generated from monocytes from a patient having an autoimmune disease with several unknown and/or complex antigens.

RA+TGFbeta+AhR agonist treated DCs are loaded with several unknown and/or complex antigens or a tissue sample extract from the same patient and thereafter are co-cultured together with autologous T cells. The T cells will be less activated compared to T cells co-cultured with control DCs loaded with the same antigens. Moreover, in the co-culture with RA+TGFbeta+AhR agonist treated DCs and T cells, a higher frequency of regulatory T cells is induced compared to T cells co-cultured with control DCs under the same conditions.

RA+TGFbeta+AhR agonist treated DCs generated from a patient with an autoimmune disease are co-cultured together with B cells. The B cells will have a higher frequency of regulatory markers such as IL-10.

RA+TGFbeta+AhR agonist treated DCs are co-cultured with B cells and T cells. The T cells will have an increased regulatory function compared to B cells and T cells co-cultured with control DCs.

The induction of a tolerogenic phenotype and function of both T cells and B cells after co-culture with RA+TGFbeta+AhR agonist treated DCs is beneficial in autoimmune diseases as these cells dampen the autoreactive activity of T and B cells.

Example 22—Impact of RA+TGFbeta+AhR Agonist on DCs Derived from the Blood of a Patient with an Autoimmune Disease and Treated without any Antigen in Relation to Breg Induction Following In Vivo Administration RA+TGFbeta+AhR agonist treated DCs are generated from monocytes from a patient having an autoimmune disease with one or several unknown antigens. The RA+TGFbeta+AhR agonist treated DCs are injected, without prior antigen loading and freezing, in situ where the DCs take up disease related antigens to be presented to T cells thus inducing disease specific regulatory T cells.

RA+TGFbeta+AhR agonist treated DCs from a patient having an autoimmune disease are cultured with one or several unknown antigens. The DCs are administered in situ. RA+TGFbeta+AhR agonist treated DCs will induce Bregs, further promoting tolerance induction towards the transplant and reducing harmful antibody production. This is in contrast to what would happen if the recipient received immunogenic donor derived DCs or no DCs at all.

Example 23—Impact of RA+TGFbeta+AhR Agonist on DCs Derived from the Blood of a Haemophilia a Patient and Loaded with FVIII on T Cell Activation and Treg Induction Haemophilia A patients that are resistant to treatment with exogenous FVIII have been found to upregulate FVIII specific effector T cells with the capacity to activate B cells which thus produce FVIII specific antibodies (inhibitors).

RA+TGFbeta+AhR agonist treated DCs generated from monocytes from a haemophilia A patient are loaded with FVIII according to method previously described above, and the RA+TGFbeta+AhR agonist treated DCs are co-cultured in vitro with T cells from the same haemophilia patient in a recall antigen assay. T cells will be less activated compared to T cells co-cultured with control DCs. Moreover, T cells in the co-culture with RA+TGFbeta+AhR agonist treated DCs will induce a higher frequency of regulatory T cells than T cells co-cultured with control DCs under the same conditions.

Example 24—Impact of RA+TGFbeta+AhR Agonist on DCs Derived from an Allogeneic Donor in Relation to Treg and Breg Induction RA+TGFbeta+AhR agonist treated DCs are generated from monocytes from an allogeneic donor. RA+TGFbeta+AhR agonist treated DCs will, when administered to the transplant recipient, induce autologous regulatory T cells and tolerance towards the transplant. This is in contrast to what would happen if the recipient received immunogenic donor derived DCs or no DCs at all.

The RA+TGFbeta+AhR agonist treated DCs from the donor are administered to the transplant recipient. RA+TGF-beta+AhR agonist treated DCs will induce Bregs further promoting tolerance induction towards the transplant and reducing harmful antibody production. This is in contrast to what would happen if the recipient received immunogenic donor derived DCs or no DCs at all.

Example 25—Impact of RA+TGFbeta+AhR Agonist on DCs Derived from a Recipient of an Allogeneic Graft in Relation to Treg and Breg Induction RA+TGFbeta+AhR agonist treated DCs are generated from monocytes from a recipient of an allogeneic graft. RA+TGFbeta+AhR agonist treated DCs are, before being administered to the transplant recipient, loaded with a mix of donor derived antigens. Such a mix of antigens may be derived from donor blood or a tissue sample from the donor, preferably a sample from the donor cells, tissues, organ or other graft to be transplanted. RA+TGFbeta+AhR agonist treated DCs will, when administered to the transplant recipient, induce autologous regulatory T cells and tolerance towards the transplant. This is in contrast to what would happen if the recipient received RA+TGFbeta+AhR agonist treated DCs without donor antigens or no DCs at all.

The RA+TGFbeta+AhR agonist treated DCs from the recipient, loaded with antigens from the donor, are administered to the transplant recipient. RA+TGFbeta+AhR agonist treated DCs will induce Bregs further promoting tolerance induction towards the transplant and reducing harmful antibody production. This is in contrast to what would happen if the recipient received RA+TGFbeta+AhR agonist treated DCs without donor antigens or no DCs at all.

REFERENCES

Agrawal S, Ganguly S, Tran A, Sundaram P, Agrawal A. 2016. Retinoic acid treated human dendritic cells induce T regulatory cells via the expression of CD141 and GARP which is impaired with age. Aging 8:1223-35.

Bakdash G, Vogelpoel L T, van Capel T M, Kapsenberg M L, de Jong E C. 2015. Retinoic acid primes human dendritic cells to induce gut-homing, IL-10-producing regulatory T cells. Mucosal Immunol. 8:265-78.

Denison and Nagy 2003. Activation of the aryl hydrocarbon receptor by structurally diverse exogenous and endogenous chemicals. Ann. Rev. Pharmacol. Toxicol., 43:309-34.

Esebanmen G E, Langridge W H R. 2017. The role of TGF-beta signaling in dendritic cell tolerance. Immunol Res. 65:987-994.

Jurado-Manzano B B, Zavala-Reyes D, Turrubiartes-Martinez E A, Portales-Perez D P, Gonzalez-Amaro R, Layseca-Espinosa E. 2017. FICZ generates human tDCs that induce CD4⁺ CD25high Foxp3⁺ Treg-like cell differentiation. Immunol Lett. 190:84-92.

Mahiout S, Lindén J, Esteban J, Sánchez-Pérez I, Sankari S, Pettersson L, Håkansson H, Pohjanvirta R. 2017. Toxicological characterisation of two novel selective aryl hydrocarbon receptor modulators in Sprague-Dawley rats. Toxicol Appl Pharmacol. 326:54-65.

Oliveira L M, Teixeira F M E, Sato M N. 2018. Impact of Retinoic Acid on Immune Cells and Inflammatory Diseases. Mediators Inflamm. 2018:3067126.

Scott C L, Aumeunier A M, Mowat A M. 2011. Intestinal CD103+ dendritic cells: master regulators of tolerance? Trends Immunol. 32:412-9.

Vlad G, Chang C C, Colovai A I, Berloco P, Cortesini R, Suciu-Foca N. 2009. Immunoglobulin-like transcript 3: A crucial regulator of dendritic cell function. Hum Immunol. 70:340-4.

Abbreviations

HA haemophilia A
DC dendritic cell
Dex Dexamethasone
tolDC tolerogenic dendritic cell
APC antigen presenting cell
MHC major histocompatibility complex
IFN interferon
PBS phosphate-buffered saline
PBMC peripheral blood mononuclear cell
FVIII Factor VIII
s.c. subcutaneous
TGF transforming growth factor
AhR aryl hydrocarbon receptor
AhR ag AhR agonist
TNF tumour necrosis factor
GM-CSF granulocyte macrophage colony stimulating factor
Ig immunoglobulin
MAb monoclonal antibody
FACS fluorescence activated cell sorting
Treg regulatory T cell
IL interleukin
RNA ribonucleic acid
RA all-trans retinoic acid
MFI mean fluorescence intensity
VitD3 Vitamin D3
FICZ 6-formylindolo(3,2b)carbazole
GARP glycoprotein-A repetitions predominant
ILT3 immunoglobulin like transcript 3
LPS lipopolysaccharide
MERTK MER proto-oncogene tyrosine kinase
BTLA B and T lymphocyte associated protein
LAP latency-associated peptide
HLA-G human leukocyte antigen G
um micromolar
C1 N-ethyl-N-phenyl-5-chloro-1,2-dihydro-4-hydroxy-1-methyl-2-oxo-quinoline-3-carboxamide Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. An ex vivo method of obtaining tolerogenic antigen presenting cells that have the capability to induce tolerance to an antigen, the method comprising:
   (a) isolating monocytes from a sample obtained from a mammal; and
   (b) culturing the isolated monocytes in a cell culture to induce differentiation of the monocytes into antigen presenting cells having a tolerogenic phenotype,
   wherein the cell culture comprises retinoic acid, TGFbeta and an AhR agonist.

2. The method according to claim 1, wherein the AhR agonist is IMA-06201 (C1).

3. The method according to claim 1, wherein the cell culture further comprises GM-CSF and IL-4 to induce differentiation of monocytes into antigen presenting cells.

4. The method according to claim 3, wherein at least one of
   the GM-CSF and IL-4 are added to the cell culture before or at the same time as any one of TGFbeta, AhR agonist and retinoic acid are added to the cell culture,
   the AhR agonist is added to the cell culture in a first dose at the same time as GM-CSF and IL-4 are first added to the cell culture, the TGFbeta and a second dose of AhR agonist are added to the cell culture after the first dose of AhR agonist is added to the cell culture, the retinoic acid is added to the cell culture after the TGFbeta and the second dose of AhR agonist are added to the cell culture, the GM-CSF and IL-4 are added to the cell culture in a second dose,
   the second dose of GM-CSF and IL-4 is added to the cell culture at the same time as the TGFbeta and the second dose of AhR agonist are added to the cell culture,
   the GM-CSF is added to the cell culture before or at the same time as any one of TGFbeta, AhR agonist, or retinoic acid are added to the cell culture and the IL-4 is added to the cell culture after a first dose of the AhR agonist is added to the cell culture, or the GM-CSF is added to the cell culture in a second dose.

5. The method according to claim 4, wherein at least one of the second dose of GM-CSF and IL-4 is added to the cell culture at the same time as the TGFbeta and the second dose of AhR agonist are added to the cell culture, or the second dose of GM-CSF is added to the cell culture at the same time as the TGFbeta and the second dose of AhR agonist are added to the cell culture.

6. The method according to claim 1, wherein at least one of the tolerogenic antigen presenting cells are dendritic cells, or the isolated monocytes are CD14$^+$ monocytes.

7. The method according to claim 1, wherein the mammal is human.

8. The method according to claim 1, wherein the sample is a sample of peripheral blood mononuclear cells.

9. The method according to claim 1, wherein the cell culture comprises the antigen or epitope containing fragment thereof.

10. The method according to claim 9, wherein the antigen or epitope containing fragment thereof is associated with the isolated monocytes.

11. The method according to claim 10, wherein at least one of the antigen or epitope containing fragment is added to the cell culture before, at the same time as or after the retinoic acid is added to the cell culture, or the antigen or epitope containing fragment is at least one of a pool of antigens or a pool of epitope containing fragments thereof.

12. The method according to claim 1, wherein the antigen or an epitope containing fragment thereof is or is derived from a biological drug.

13. The method according to claim 12, wherein the biological drug is at least one of Factor VIII or a derivative or fragment thereof, Factor IX or a derivative or fragment thereof, or an antibody or antibody fragment thereof.

14. The method according to claim 1, wherein the antigen or an epitope containing fragment thereof is associated with an allograft, or is or is derived from a self-antigen.

15. The method according to claim 1, wherein the tolerogenic antigen presenting cells when unstimulated or when stimulated demonstrate one or both of the following properties: (i) a level of expression of ILT3 which is at least 150% of that of control cells, a level of expression of CD83 which is no more than 70% of that of control cells, and a level of expression of CD86 which is no more than 80% of that of control cells; and (ii) T cell proliferation induction capacity which is no more than 70% of that of control cells.

16. The method according to claim 15, wherein the tolerogenic antigen presenting cells express CD103.

17. The method according to claim 1, wherein the tolerogenic antigen presenting cells when cultured with T cells induce regulatory T cells.

18. The method according to claim 17, wherein the regulatory T cells are CD4$^+$, CD25$^{hi}$, Foxp3$^+$, or Tr1 regulatory T cells.

19. A tolerogenic antigen presenting cell or population thereof obtainable or obtained by the method of claim 1.

20. The tolerogenic antigen presenting cell or population thereof according to claim 19, wherein at least one of the antigen presenting cell or population thereof is further characterized by expression of one or more of the following:
  (i) HLA-G;
  (ii) BTLA;
  iii) MERTK;
  (iv) LAP, or
  the antigen presenting cell when unstimulated or when stimulated have a level of production of IL-23 which is no more than 100% of that of control cells.

21. A method of treating a mammalian subject with or at risk of an immune reaction to an antigen, the method comprising administering the tolerogenic antigen presenting cell or population thereof according to claim 19 to the mammalian subject thereby establishing immune tolerance to the antigen.

22. A method of preventing immune rejection of an allograft in a recipient subject wherein the allograft is derived from a donor, comprising administering tolerogenic antigen presenting cells according to claim 19 to the recipient subject thereby establishing tolerance to the allograft, wherein the tolerogenic antigen presenting cells are obtained from monocytes isolated from a sample taken from the donor or the recipient.

23. A method of treating a mammalian subject with or at risk of an immune reaction to an antigen, the method comprising (i) obtaining a tolerogenic antigen presenting cell or population thereof that has the capability to induce tolerance to an antigen according to the method of claim 1, wherein the tolerogenic antigen presenting cell or population thereof is obtained from a sample of isolated monocytes derived from the mammalian subject and (ii) administering the tolerogenic antigen presenting cell or population thereof back to the mammalian subject thereby establishing immune tolerance to the antigen.

* * * * *